United States Patent
Stone et al.

(10) Patent No.: US 9,023,788 B2
(45) Date of Patent: May 5, 2015

(54) METHODS COMPOUNDS AND PHARMACEUTICAL COMPOSITIONS FOR TREATING ANXIETY AND MOOD DISORDERS

(75) Inventors: Eric A. Stone, Chappaqua, NY (US); Yan Lin, Jersey City, NJ (US); David Quartermain, New York, NY (US); Yasmeen Sarfraz, Jackson Heights, NY (US)

(73) Assignee: New York University, New York, NY (US)

(*) Notice: Subject to any disclaimer, the term of this patent is extended or adjusted under 35 U.S.C. 154(b) by 556 days.

(21) Appl. No.: 13/066,620

(22) Filed: Apr. 19, 2011

(65) Prior Publication Data

US 2012/0010125 A1 Jan. 12, 2012

Related U.S. Application Data

(60) Provisional application No. 61/342,821, filed on Apr. 20, 2010.

(51) Int. Cl.
A61K 31/75 (2006.01)
A61K 38/00 (2006.01)
A61K 31/075 (2006.01)

(52) U.S. Cl.
CPC .................... A61K 31/075 (2013.01)

(58) Field of Classification Search
None
See application file for complete search history.

(56) References Cited

U.S. PATENT DOCUMENTS

| | | | |
|---|---|---|---|
| 4,275,074 A * | 6/1981 | Langham | 514/646 |
| 6,825,382 B2 | 11/2004 | Ammann | |
| 7,655,396 B1 | 2/2010 | Kedzie et al. | |
| 2008/0301822 A1* | 12/2008 | Perez | 800/3 |
| 2009/0221656 A1* | 9/2009 | Learmonth et al. | 514/392 |
| 2009/0263463 A1 | 10/2009 | Zanella et al. | |
| 2010/0016251 A1 | 1/2010 | Sofia et al. | |
| 2012/0010125 A1* | 1/2012 | Stone et al. | 514/1.3 |

FOREIGN PATENT DOCUMENTS

| EP | 1 368 305 B1 | 8/2008 |
|---|---|---|
| WO | WO 2007/047351 | 4/2007 |
| WO | WO 2008/004027 | 4/2008 |

OTHER PUBLICATIONS

Arnsten, et al., Biol. Psychiatry, "Neurobiology of Executive Functions: Catecholamine Influences on Prefrontal Cortical Functions," 2005; 57: 1377-1384.
Arnsten, et al., Biol Psychiatry, "alpha-1 Noradrenergic Receptor Stimulation Impairs Prefrontal Cortical Cognitive Function," 1999; 45: 26-31.
Aston-Jones, et al., Annu. Rev. Neurosci., "An integrative theory of Locus Coeruleus-Norepinephrine fuction: Adaptive gain and optimal performance," 2005; 28: 403-450.
Bissette, et al., Neuropsychopharmacology, "Elevated concentrations of CRF in the Locus Coeruleus of depressed subjects," 2003; 28: 1328-1335.
Blair-West, et al., Acta Psychiatr Scand., "Down-rating lifetime suicide risk in major depression," 1997; 95(3): 259-63 (Abstract).
Bouret, et al., Trends Neurosci., "Network reset: a simplified overarching theory of lous coeruleus noradrenaline function," 2005; 28(11): 574-582.
Carr, et al., Neuropsychopharmacology, "Antidepressant-like effects of k-Opioid receptor antagonists in Wistar Kyoto rats," 2010; 35: 752-763.
Coplan, et al., Psychopharmacology Bulletin, "A view on Noradrenergic, hypothalamic-pituitary-adrenal axis and extrahypothalamic corticotrophin-releasing factor function in anxiety and affective disorders: the reduced growth hormone response to clonidine," 1997; 33(2): 193-204.
Cryan, et al., Neurosci. Biobehay. Revs., "The tail suspension test as a model for assessing antidepressant activity: review of pharmacological and genetic studies in mice," 2005; 29: 571-625.
Doze, et al., Brain Res., "alpha1A- and alpha1B-Adrenergic Receptors Differentially Modulate Antidepressant-like Behavior in the Mouse," 2009; 1285: 148-157.
Drevets, European Neuropsychopharmacology, "Function anatomical correlates of antidepressant drug treatment assessed using PET measures of regional glucose metabolism," 2002; 123: 527-544 (Abstract).
Frenois, et al., Psychoneuroendocrinology, "Lipopolysaccharide induces delayed FosB/DeltaFosB immunostaining within the mouse extended amygdala, hippocampus and hypothalamus, that parallel the expression of depressive-like behavior," 2007; 32(5): 516-531.
Friedman, et al., Neuropsychopharmacology, "Programmed acute electrical stimulation of ventral tegmental area alleviates depressive-like behavior," 2009; 34: 1057-1066.
Gupta, et al., Mol Pharmacol., "alpha1-Adrenergic receptors regulate neurogenesis and Gliogenesis," 2009; 76: 314-326.

(Continued)

*Primary Examiner* — Maury Audet
(74) *Attorney, Agent, or Firm* — Klauber & Jackson LLC

(57) ABSTRACT

Compounds and pharmaceutical compositions containing such compounds having formula I are provided:

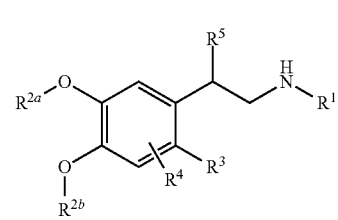

where $R^1$, $R^{2a}$, $R^{2b}$, $R^3$, $R^4$, and $R^5$ are as defined herein. The compounds and pharmaceutical compositions thereof are useful for the prevention and treatment of a variety of conditions in mammals including humans, including anxiety and mood disorders such as depression.

25 Claims, 19 Drawing Sheets

(56) References Cited

OTHER PUBLICATIONS

Haapalinna, et al., Naunyn-Schmiedebergs Arch Pharmacol, "Evaluation of the effects of a specific alpha2- adrenoceptor antagonist, atipamezole, an alpha1- and alpha2-adrenoceptor subtype binding, brain neurochemistry and behaviour in comparison with yohimbine," 1997; 356: 570-582.
Hall, et al., British Journal of Anesthesia, "Sedative, analgesic and cognitive effects of clonidine infusions in humans," 2001; 86(1): 5-11.
Hancock, et al., J Recept Signal Transduct Res., "Actions of terazosinand its enantiomers at subtypes of alpha 1- and alpha 2-adrenoceptors in vitro," 1995; 15(7-8): 863-85 (Abstract).
Harsing, et al., Pharmacology Biochemistry and Behavior, "Possible roles of Alpha-2 and Alpha-1 Adrenoceptors in the Experimentally-Induced Depression of the Central Nervous System," 1989; 32: 927-932.
Inskip, et al., Br J Psychiatry, "Lifetime risk of suicide for affective disorder, alcoholism and schizophrenia," 1998; 172: 35-7 (Abstract).
Introini-Collison, et al., Brain Res., "Memory-enhancing effects of post-training dipivefrin and epinephrine: involvement of peripheral and central adrenergic receptors," 1992; 572: 81-86.
Johnson, et al., European Journal of Pharmacology, "Characterization of alpha1-adrenoceptors which increase cyclic AMP accumulation in rat cerebral cortex," 1986; 129: 293-305.
Johnson, et al., Mol Pharmacology, "Differentiation of alpha1-adrenergic receptors linked to phosphatidylinositol turnover and cyclic AMP accumulation in rat brain," 1987; 31: 239-246.
Kasper, et al., World J Biol Psychiatry, "Beyond the monoaminergic hypothesis: Agomelatine, a new antidepressant with innovative annovative mechanism of action," 2009; 10(2): 117-126.
Kitada; et al., Jpn J Pharmacol, "Further studies on the suppressing effect of isoproterenol on the imobility-reducing action of desipramine in the forced swimming test," 1983; 33: 867-873.
Koo, et al., PNAS USA, "Nuclear factor-kB is a critical mediator of stress-impaired neurogenesis and depressive behavior," 2010; 107(6): 2669-2674.
Koo, et al., Neurosci Lett., "Interleukin-1 receptor null mutant mice show decreased anxiety-like behavior and enhanced fear memory," 2009; 456: 39-43.
Lin, et al., Neurospychopharmacology, "Role of alpha1-adrenoceptors of the locus coeruleus in self-stimulation of the medical forebrain bundle," 2007; 32: 835-841.
Lin, et al., Synapse, "Possible dopaminergic stimulation of Locus Coeruleus alpha1-adrenoceptors involved in behavioral activation," 2008; 62(7): 516-523.
Lucas, et al., Neuron, "Serotonin4 (5-HT4) receptor agonists are putative antidepressants with a rapid onset of action," 2007; 55: 712-725.
Lucki, et al., J Clin Psychiatry, "Distinguishing roles for norepinephrine and serotonin in the behavioral effects of antidepressant drugs," 2004; 65(suppl 4): 11-124.
Ma, et al., Neuroscience, "Chronic intermittent hypoxia sensitizes acute hypothalamic-pituitary-adrenal stress reactivity and Fos induction in the rat locus coeruleus in response to subsequent immobilization stress," 2008; 154: 1639-1647.
Machado-Vieira, et al., Pharmacol Ther., "Ketamine and the next generation of antidepressants with a rapid onset of action," 2009; 123(2): 143-150.
Malkesman, et al., Biological Psychiatry, "The female urine sniffing test: A novel approach for assessing reward-seeking behavior in rodents," 2010; 67(9): 864-871.
Marchetti, et al., Biological Psychiatry, "Synaptic adaptations of CA1 pyramidal neurons induced by a highly effective combinational antidepressant therapy," 2010: 67: 146-154.
Mayberg, Biological Psychiatry, "Defining the neural circuitry of depression: Toward a new nosology with therapeutic implications," 2007; 61: 729-730.
Mayberg, et al., Neuron, "Deep brain stimulation for treatment-resistant depression," 2005; 45: 651-660.
Muigg, et al., Biol Psychiatry, "Altered brain activation pattern associates with drug-induced attenuation of enhanced depression-like behavior in rats bred for high anxiety," 2007; 61: 782-706.
Nestler, et al., Biological Psychiatry, "Molecular control of locus coeruleus neurotransmission," 1999; 46: 1131-1139.
Ordway, et al., Biol Psychiatry, "Elevated agonist binding Alpha2-adrenoceptors in the locus coeruleus in major depression," 2003; 53: 315-323.
Pertovaara, Progress in Neurobiology, "Noradrenergic pain modulation," 2006; 80: 53-83.
Price, et al., Neuropsychopharmacology, "Neurocircuity of mood disorders," 2010; 35: 192-216.
Richelson, Mayo Clinic Proceedings, "Pharmacology of Antidepressants," 2001; 76: 511-527.
Sartorius, et al., Int J Neurophychopharmacol, "Antidepressant medications and other treatments of depressive disorders: a CINP Task Force report based on a review of evidence," 2007; 10(Suppl 1): 81-207) (Abstract).
Schmidt, et al., Behavioral Pharmacology, "The role of neurotrophic factors in adult hippocampal neurogenesis, antidepressant treatments and animal models of depressive-like behavior," 2007; 18: 391-418.
Smadja, et al., Psychopharmacology, "CCK-B receptors in the limbic system modulate the antidepressant-like effects induced by endogenous enkephalins," 1997; 132: 227-236.
Stone, et al., Brain Research, "Decrease in stress-induced c-Fos-like immunoreactivity in the lateral septal nucleus of learned helpless rats," 1999; 822: 256-259.
Stone, et al., Neuroscience, "Brain alpha 1-adrenergic neurotransmission is necessary for behavioral activation to environmental change in mice," 1999; 94(4): 1245-1252.
Stone, et al., Neuropharmacology, "Pharmacological evidence for the role of central alpha 1B-adrenoceptors in the motor activity and spontaneous movement of mice," 2001; 40: 254-261.
Stone, et al., Behavioural Brain Research, "Gross mapping of alpha1-adrenoceptors that regulate behavioral activation in the mouse brain," 2004; 152: 167-175.
Stone, et al., Synapse, "Role of locus coeruleus alpha1-adrenoceptors in motor activity in rats," 2004; 54: 164-172.
Ma et al., British medical Bulletin 2005; 71:77-92.
Stone, et al., European Journal of Pharmacology, "Pharmacological blockade of brain alpha1-adrenoceptors as measured by ex vivo [3H]prazosin binding is correlated with behavioral immobility," 2001; 420: 97-102.
Stone, et al., Psychopharmacology, "alpha1-adrenergic and alpha2-adrenergic balance in the dorsal pons and gross behavioral activity in mice in a novel environment," 2005; 183: 127-132.
Stone, et al., Progress in Neuro-Psychopharmacology & Biological Psychiatry, Reduced evoked fos expression in activity-related brain regions in animal models of behavioral depression, 2007; 31: 1196-1207.
Stone, et al., Current Protocols in Neuroscience, "Open-space forced swim model of depression for mice," 2011; 54: 9.36.1-9.36.8.
Stone, et al., Brain Res., "Marked behavioral activation from inhibitory stimulation of locus coeruleus alpha1- adrenoceptors by a full agonist," 2009; 1291: 21-31.
Stone, et al., Pharmacol Biochem Behav., "Evaluation of the repeated open-space swim model of depression in the mouse," 2008; 91(1): 190-195.
Stone, et al., Neurosci Biobehav Rev., "A final common pathway for depression? Progress toward a general conceptual framework," 2008; 32(3): 508-524.
Stone, et al., Int. Journal of Neuropsychopharmacology, "Antidepressant-like action of intracerebral 6-fluoronorepinephrine, a selective full alpha-adrenoceptor agonist," 2011; 14(319-331).
Sun, et al., Neuroscience, "Induced depressive behavior impairs learning and memory in rats," 2004; 129: 129-139.
Sun, et al., Journal of Neuroscience Methods, "Open space swimming test to index antidepressant activity," 2003; 126: 35-40.
Sun, et al., Behavioral Pharmacology, "Effects of age on susceptibility to the induction of depressive behavior and imipramine pramine in rats," 2008; 19: 334-338.

(56) References Cited

OTHER PUBLICATIONS

Sun, et al., Journal of Pharmacology & Experimental Therapeutics, "Differential gender-related vulnerability to depression induction and converging antidepressant responses in rats," 2006; 316(2): 926-932.

Talalaenko, et al., Neuroscience and Behavioral Physiology, "Neurochemical characteristics of the ventromedial hypothalamus in Mediating the antiaversive effects of anxiolytics in different models of anxiety," 2003; 33(3): 255-261.

Thonberg, et al., Biochem J., "A novel pathway for adrenergic stimulation of cAMP-response-element-binding protein (CREB) phosphorylation: mediation via alpha1-adrenoceptors and protein kinase C activation," 2002; 364: 73-79.

Valentino, et al., Eur. J Pharmacol., "Convergent regulation of locus coeruleus activity as an adaptive response to stress," 2008; 583(2-3): 194-203.

Weiss, et al., Neuropeptides, "Testing the hypothesis that locus coeruleus hyperactivity produces depression-related changes via galanin," 2005; 39: 281-287.

West; et al., Int J Neuropsychopharmacol, "Antidepressant drugs with differing pharmacological actions decrease activity of locus coeruleus neurons," 2009; 12(5): 627-641.

Wong, et al., PNAS USA, "Pronounced and sustained central hypernoradrenergic function in major depression with melancholic features: Relation to hypercortisolism and corticotropin-releasing hormone," 2000; 97(1): 325-330.

Yang, et al., J Pharmacol Exp Ther., "The involvement of Central Noradrenergic Systems and Corticotropin-releasing factor in defensive-withdrawal behavior in rats," 1990; 255(3): 1064-1070.

Yirmiya, Brain Research, "Endotoxin produces a depressive-like episode in rats," 1996; 711: 163-174.

Zarate, et al., Arch Gen Psychiatry, "A randomized trial of an N-methyl-D-aspartate antagonist in treatment-resistant major depression," 2006; 63: 856-864.

Zarrindast, et al., Eur J of Pharmacology, "Involvement of adrenergic and cholinergic systems in nicotine-induced anxiogenesis in mice," 2000, 407: 145-158.

\* cited by examiner

Effect of ivt. 6FNE on locomotor activity in open field

Effect of ivt. 6FNE on locomotor activity in open field

IP dp6FNE (acute)
Repeated Open Space

IP dp6FNE (acute)
Tail suspension test

IP dp6FNE (acute)
Chronic Mild Stress

IP DMI (acute)
Repeated Open Space

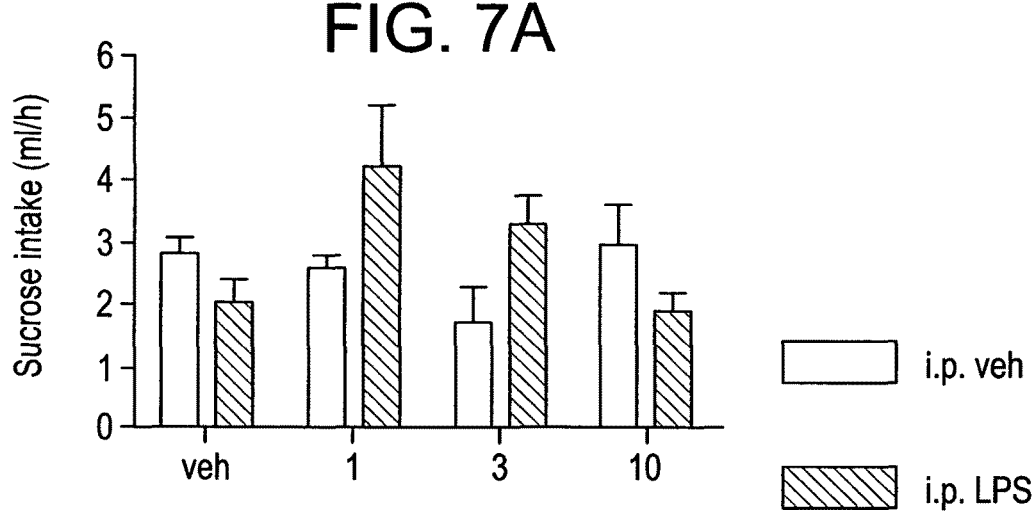
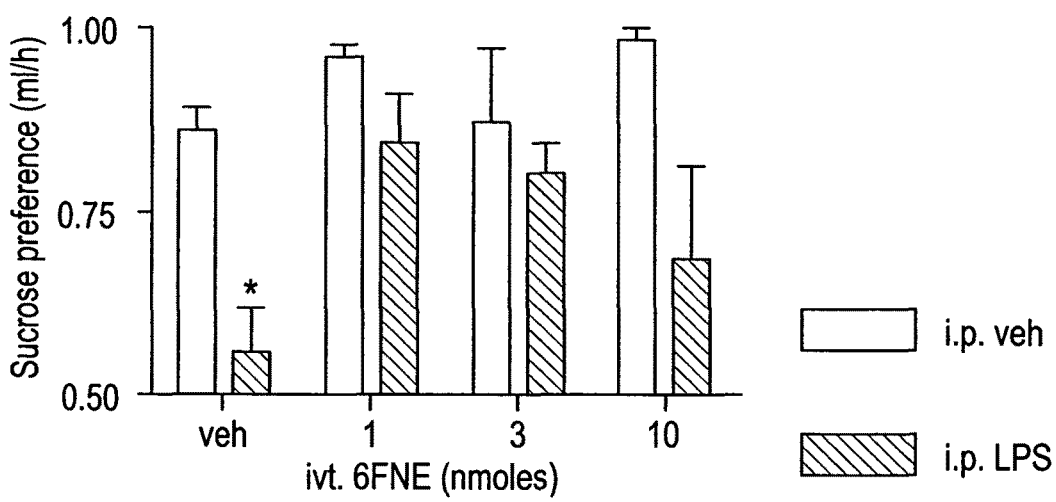
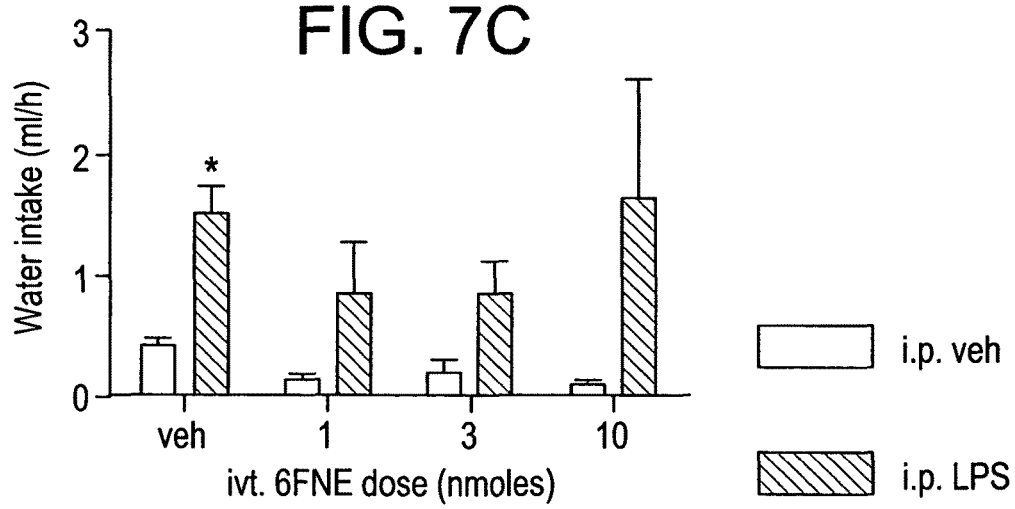

Tail suspension test

Repeated open-space forced swim

Acute Forced Swim

Tail suspension test

METHODS COMPOUNDS AND PHARMACEUTICAL COMPOSITIONS FOR TREATING ANXIETY AND MOOD DISORDERS

CROSS REFERENCE TO RELATED APPLICATIONS

This application claims priority from and the benefit of U.S. provisional application Ser. No. 61/342,821, filed on Apr. 20, 2010, the disclosure of which is herein incorporated by reference.

FIELD OF THE INVENTION

This invention relates to novel pharmaceutical compositions comprising a compound or a prodrug of a compound capable of modulating both $\alpha 1$- and $\alpha 2$-adrenergic receptor, an a-adrenergic agonist, and a carrier. Specifically, the invention relates to novel pharmaceutical composition comprising a prodrug of a full agonist of $\alpha 1$- and $\alpha 2$-adrenergic receptor, an additional adrenergic agonist, and a carrier. The invention further relates to novel compounds or prodrugs and preparation of such compounds. This invention also relates to methods for the prevention, prophylaxis and/or treatment of conditions that are causally related to depression, stress or other disorders.

BACKGROUND OF THE INVENTION

Major depressive illness represents one of the leading causes of disability with an estimated lifetime prevalence of 16.2% and an eventual suicide rate of from 6-15% (Blair-West, et al., *Acta Psychiatr.Scand.* (1997) 95:259-263; Inskip, et al., *Br.J.Psychiatry* (1998) 172:35-37) While numerous antidepressant drugs are currently available and are partially effective, most are slow acting and fail to produce remission in a significant fraction of patients. This lack of adequate timely and efficacious antidepressants may be due to an inadequate understanding of the underlying pathophysiology and neurobiology of major depression.

A number of new candidate drugs and procedures have been developed to overcome some of these difficulties. These include ketamine (Zarate, et al., *Arch Gen Psychiatry* 2006; 63: 856-864), 5HT4 receptor agonists (Lucas, et al., *Neuron*, 2007; 55: 712-725), deep brain stimulation (Mayberg, et al., *Neuron* 2005; 45: 651-660, 2005), agomelatin (Kasper, et al., *World J Biol Psychiatry* 2009; 10: 117-126), and antagonists of CRF (Zoumakis, et al., *Ann N Y Acad Sci* 2006; 1083: 239-251), NK1 (Ebner, et al., *Curr Pharm Des* 2009; 15: 1647-1674), kappa opioid (Carr, et al., *Neuropsychopharmacology* 2010; 35: 752-763), and cholecystokinin (Smadja, et al., *Psychopharmacology* 1997; 132: 227-236) receptors. While some of these agents appear to have an increased speed of action and reduced side effect profile, they may not possess greater efficacy than existing drugs and may have further limitations themselves in terms of degree of invasiveness, losses of efficacy with chronic administration, and dissociative side effects. Moreover, while some of the newer agents can rapidly reverse the motoric (i.e., immobility) aspects of depression, most continue to have delayed actions on depressive anhedonia, one of the core symptoms of the illness (Friedman, et al., *Neuropsychopharmacology* 2009; 34: 1057-1066, Machado-Vieira, et al., *Pharmacol Ther* 2009; 123: 143-150).

Recently, however, the picture has begun to improve with significant advances in the elucidation of the basic neural circuitry of this disorder. In global terms, it now appears that depression arises from a shift of neural activity away from brain regions involved in motivation and behavioral performance towards regions involved in stress responses. (Mayberg, *Biological Psychiatry* 2007, 61: 729-730; Steciuk et al., *Brain Research*, 1999; 822: 256-259; Price et al., *Neuropsychopharmacology*, 2010, 35; 192-216 and Drevets, *European Neuropsychopharmacology*, 2009; 12:527-544; Stone et al., *Neuroscience and Biobehavioral Reviews*, 2008; 32:508-524). Thus, in both depressed patients and animal models of the disorder, brain structures controlling executive functions and behavioral performance such as the dorsolateral prefrontal motor and piriform cortex, lateral septal nucleus and nucleus accumbens tend to be deactivated or unresponsive to stimulation whereas areas controlling emotional and autonomic responses to stress including ventral limbic forebrain structures, amygdala, insula, bed nucleus of the stria terminalis, paraventricular nucleus of the hypothalamus and locus coeruleus tend to be overly activated or hyperresponsive.

The shift of activity between the motivational and stress regions has suggested that the heightened activity of the stress areas is the cause of the inhibition of the motivational regions. This view leads to the prediction that it should be possible to treat depression rapidly and effectively by selectively inhibiting central stress circuits. Such a strategy was first employed by Weiss and colleagues (Simson, et al., *Neuropharmacology* (1986) 25:385-389) and was directed at the locus coeruleus (LC), the main noradrenergic stress nucleus of the brain, which had been implicated in human depression (Bissette, et al., *Neuropsychopharmacology* (2003) 28:1328-1335; Ordway, et al., *Biol.Psychiatry* (2003) 53:315-323). Weiss et al. studied rats who showed increased depressive-like immobility in a forced swim test as a result of previous exposure to traumatic electric shock stress. They found that infusion of the $\alpha_2$-adrenergic agonist, clonidine, in the LC to inhibit the latter's electrical activity, produced an immediate reduction of the depressive behavior consistent with the hypothesized role of the nucleus. Subsequently further confirmatory evidence was provided on the basis of experiments with another $\alpha$-agonist, 6-fluoronorepinephrine, (6FNE), which produces an even more profound inhibition of the LC activity than clonidine as a result of the combined stimulation of inhibitory $\alpha_1$- and $\alpha_2$-receptors (Stone, et al., *International Journal of Neuropsychopharmacology* (2011) 14: 319-331; Stone, et al., *Brain Res.* (2009) 1291:21-31). This compound produced a more marked and rapid antidepressant response than clonidine when infused in the LC prior to several different behavioral tests.

The mechanism by which excessive LC activity might lead to depression is not presently established although it has been hypothesized that it may involve the release of the inhibitory peptide galanin from noradrenergic fibers in the ventral tegmental area (Weiss, et al., *Neuropeptides* (2005) 39:281-287), thus inhibiting a key dopaminergic motivational behavioral system. Alternatively, it may involve excessive activation of postsynaptic $\alpha_1$-adrenoceptors by NE itself in certain forebrain regions, such as the prefrontal cortex, causing the neural activity in the latter structure to be markedly inhibited (Arnsten, et al., *Biol. Psychiatry* (2005) 57:1377-1384).

Central $\alpha 1$-adrenoceptors have long been known to play an essential role in behavioral activation under a variety of experimental conditions. Blockade of these receptors in a number of brain regions produces immobility in novel surroundings whereas stimulation may lead to behavioral activation in familiar environments (Stone et al., *Neuroscience* 1999; 94:1245-1252; Stone et al., *Neuropharmacology* 2001:

401:354-261; Stone et al., *Behav. Brain Res.* 2004; 152:167-175). The LC appears to be a key region in this system in that it contains a dense concentration of α1-receptor binding sites (Jones et al., *J. Comp. Neurol.*, 1985; 231:190-208; Stone et al., *Synapse*, 2004, 54; 164-172) having the above behavioral properties (Stone et al., *Behav. Brain Res.* 2004; 152:167-175; Stone et al., *Synapse*, 2004; 54:164-172; Lin et al., *Neuropsychopharmacology*, 2007; 32:835-841). Moreover this nucleus is a site of convergence for systems regulating arousal (Cedarbaum, et al., *J. Comp. Neurol.* 1978; 178:1-16; Berridge et al., *Psychol. Med.* 1993; 23:557-564), motivated behavior (Aston-Jones; et al., *Annu. Rev. Neurosci.* 2005; 28:403-450; Bouret, et al., *Trends Neurosci.* 2005; 28:574-582), stress (Valentino, et al., *Eur. J. Pharmacol.* 2008; 583: 194-203; Ma et al., *Neuroscience* 2008; 154:1639-1647; Korf et al., *Neuropharmacology* 1973, 12:933-938) and pain (Pertovaara, *Prog. Neurobiol.* 2006; 80:53-83) and can affect a wide range of behavioral and physiological functions.

How α1-adrenoreceptors of the LC achieve behavioral activation is not presently well understood. However, while α1-adrenoceptors have traditionally been thought to mediate postsynaptic excitation (Hermann et al., *J. Physiol.* 2005; 562:553-568), several recent studies have shown that they can also depress excitatory synaptic or increase GABAergic neurotransmission in a number brain regions (McElligott, et al., *Neuropsychopharmacology* 2008; 33:2313-2323; Lei et al., *J. Neurophysiol.* 2007; 98:2868-2877). These findings were of interest because a reduced functional activity of the LC is known to lead to the activation of task-specific behaviors (Aston-Jones, et al., *Annu. Rev. Neurosci.* 2005; 28:403-450; Weiss et al., *Neuropharmacology* 1986; 25:367-384; Grant, et al., *Biol. Psychiatry* 2001; 49:117-129), while excessive LC activity has been shown to cause aversion and the abandonment of rewarding behaviors (Smith et al., *Brain Struct. Funct.* 2008, 213; 43-61; Taylor et al., *Psychopharmacology* 1988, 96; 121-134), and possibly depression (Grant et al., *Biol. Psychiatry* 2001, 49; 117-129; Simson et al., *Neuropharmacology* 1986; 25:385-389; Stone, *Behavior and Brain Sciences* 1982; 5:122). It was therefore be of interest to determine how the functional activity of this nucleus is affected by α1-adrenergic stimulation that produces behavioral activation. Previous work on this problem had utilized local infusion of the selective α1-agonist, phenylephrine (PE), which produces a weak stimulation of exploratory behavior in rats (Stone et al., *Synapse*, 2004; 54:164-172). PE, however, is known to be only a partial agonist at brain α1-adrenoceptors (Johnson, et al., *Eur. J. Pharmacol.* 1986; 129:293-305; Law-Tho et al., *Eur. J. Neurosci* 1993; 5:1494-1500). In contrast, 6-fluoronorepinephrine (6FNE), which is the only known selective full agonist at all central α-adrenoceptors (Johnson et al., *Eur. J. Pharmacol.* 1986; 129; Brasili et al., *Eur. J. Pharmacol.* 1987; 144:141-146), produces marked behavioral activation in the home cage when infused in the mouse LC.

A study was therefore undertaken to determine the effect of stimulation of the $\alpha_1$-receptors of the locus coeruleus on the neural activity of this nucleus as well as on other stress-related and motivational-related brain regions. Stimulation of these receptors with the full agonist, 6FNE, produced a virtually complete cessation of the neural activity of this nucleus whereas blockade of these receptors with the $\alpha_1$-antagonist, terazosin, produced an excitation of virtually every neuron of the nucleus, as measured from the expression of c-Fos its cells (Stone, et al., *International Journal of Neuropsychopharmacology* (2011) 14: 319-331). The activity of the LC was therefore shown to be reciprocally or inversely related to the level of ongoing motivated behavioral activity. Since depression is accompanied by an inhibition of many of these motivated behaviors and by a hyperactivity of the LC, it was reasoned that inhibition of the nucleus by the full agonist, 6FNE, would produce a potent antidepressant action. As discussed above, this was confirmed by tests of the effect of the effects of local infusion of 6FNE near the LC on 4 different tests of antidepressant activity: the acute forced swim, acute tail suspension, chronic open space forced swim and lipopolysaccharide induced anhedonia (Stone, et al., *Brain Res.* (2009) 1291: 21-31). From tests of anxiety in the open field and of the activity of stress-related brain regions after local infusion of 6FNE, these experiments also revealed that stimulation of these α-adrenergic receptors of the LC may act by inhibition of the organism's state of stress.

SUMMARY OF THE INVENTION

In a first aspect, the present invention provides compounds, and pharmaceutical compositions thereof, having potency, specificity and selectivity in the prevention, prophylaxis, and treatment of depression, including for instance, major depression and dysthymia, and other related conditions described herein.

Accordingly, the invention provides pharmaceutical compositions comprising:
 a) a full agonist of α1- and α2-adrenoceptor; and
 b) a carrier or adjuvant.

Specifically, the invention provides pharmaceutical compositions comprising:
 a) a prodrug of a full agonist of α1- and α2-adrenoceptor; and
 b) a carrier or adjuvant.

More specifically, the invention provides pharmaceutical compositions comprising:
 a) a full agonist or a prodrug of a full agonist of α1- and α2-adrenoceptor;
 b) an additional α-adrenergic modulator; and
 c) a carrier or adjuvant.

In another aspect the invention provides a pharmaceutical composition comprising:
 a) a prodrug according to formula I:

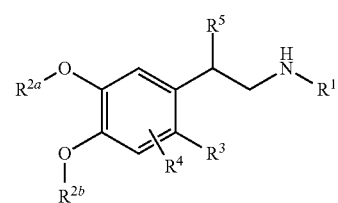

wherein
 $R^1$ is selected from H, and substituted or unsubstituted $C_1$-$C_6$ alkyl;
 each $R^{2a}$, and $R^{2b}$ is independently selected from H, and an enzymatically cleavable group; provided that at least one of $R^{2a}$, and $R^{2b}$ is other than H;
 each $R^3$ and $R^4$ is independently selected from H, halo, substituted or unsubstituted $C_1$-$C_6$ alkyl, substituted or unsubstituted halo $C_1$-$C_6$ alkyl, hydroxy, substituted or unsubstituted amino, and substituted or unsubstituted $C_1$-$C_6$ alkoxy;
 and $R^5$ is H, or OH;

or a pharmaceutically acceptable salt, or solvate thereof; and stereoisomers, isotopic variants and tautomers thereof;
b) an additional α-adrenergic modulator; and
c) a carrier or adjuvant.

In one embodiment, with respect to the pharmaceutical composition of the invention, the composition comprises:
a) a prodrug according to formula IIa or IIb or IIc:

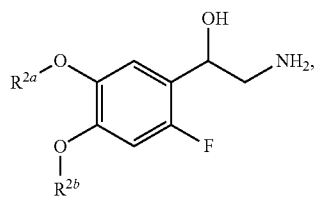

IIa

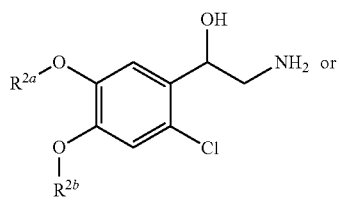

IIb

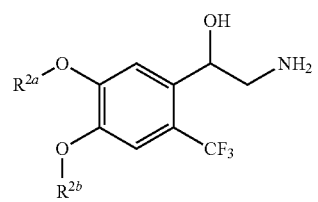

IIc wherein
each $R^{2a}$, and $R^{2b}$ is independently selected from H, and an enzymatically cleavable group;
or a pharmaceutically acceptable salt, or solvate thereof; and
stereoisomers, isotopic variants and tautomers thereof;
provided that at least one of $R^{2a}$, and $R^{2b}$ is other than H;
b) an additional α-adrenergic modulator; and
c) a carrier or adjuvant.

In yet another aspect, the invention provides a compound according to formula IIa or IIb or IIc:

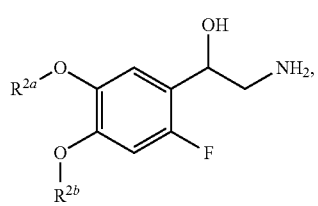

IIa

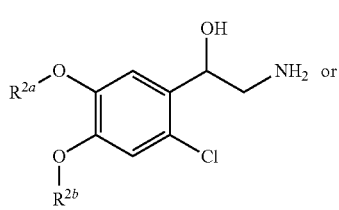

IIb

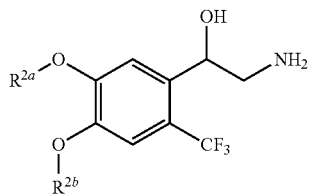

IIc wherein
each $R^{2a}$, and $R^{2b}$ is independently selected from H, and an enzymatically cleavable group; provided that at least one of $R^{2a}$, and $R^{2b}$ is other than H;
or a pharmaceutically acceptable salt, or solvate thereof; and stereoisomers, isotopic variants and tautomers thereof.

In another aspect, pharmaceutical compositions are provided comprising a compound of the invention, and a pharmaceutical carrier, excipient or diluent. The pharmaceutical composition can comprise one or more of the compounds described herein. In a further embodiment, the pharmaceutical compositions of the invention can comprise a compound in combination with one or more other compounds and/or compositions having a like therapeutic effect.

It will be understood that compounds of the present invention useful in the pharmaceutical compositions and treatment methods disclosed herein, can be pharmaceutically acceptable as prepared and used.

In a second aspect, the present invention provides methods for preventing, treating or ameliorating an anxiety disorder or a mood disorder such as depression, including for instance major depression or dysthymia, by administering to a mammal in need thereof a therapeutically effective amount of one or more of the compounds provided herein or a pharmaceutical composition containing one or more of the compounds provided herein. The methods may be effective to prevent, treat or ameliorate the anxiety or mood disorder or reduce symptoms of anxiety or depression. The methods may also be useful for reducing the likelihood of, deterring, or preventing suicide.

In some instances, the methods are effective to reduce the neural response in a stress response, particularly in regions of the brain active in a stress response such as, for instance the nucleus locus coeruleus or the paraventricular hypothalamus. Also, in some instances, the methods are effective to increase neural activity in areas of the brain involved in motivated behavior, such as, for instance, the nucleus accumbens or lateral septal nucleus. The methods may be effective to reduce the suppressing effects of stress on motivated behavior. In many instances, the compounds and compositions of the present invention are effective as agonists to α adrenoceptors, such as, for instance either or both of α1 and α2 adrenoceptors, preferably α1 receptor agonists. Likewise, the compounds and compositions of the present invention may be effective as agonists to either or both of α1A and α1B adrenoceptors, preferably α1B receptor agonists.

The methods may feature providing the compounds and compositions of the present invention by any effective means of delivery, such as, for instance orally or intravenously. The methods may provide an observable reduction in symptoms associated with an anxiety or mood disorder, such as depression or dysthymia, within a shorter time than an observable reduction in symptoms associated with an anxiety or mood disorder, such as depression or dysthymia provided by other therapies. A reduction in one or more symptoms associated with an anxiety or mood disorder, such as depression or dysthymia, may be observable within 1 minute, 2 minutes, 5 minutes, 10 minutes, 15 minutes, 30 minutes, 45 minutes, 1 hours, 2 hours, 3 hours, 4 hours, 6 hours, 12 hours, 1 day, 2 days, 3 days, 5 days, one week, 10 days, 2 weeks, 3 weeks, 1 month, 6 weeks, 2 months or 3 months. A reduction in one or more symptoms associated with an anxiety or mood disorder, such as depression or dysthymia, may be observable within at time period that is 10%, 20%, 25%, 30%, 40, 50%, 60%, 70%, 75%, 90%, 95% or more shorter than the time required for an observable reduction in one or more symptoms associated with an anxiety or mood disorder, such as depression or dysthymia provided by other therapies. The compounds and compositions of the present invention may be provided alone or in combination with one or more therapies, including one or more standard therapies for depression, such as, for instance, one or more tricyclic antidepressants, one or more serotonin reuptake inhibitors, or one or more monoamine oxidase inhibitors.

In addition to the methods of treatment, the present invention extends to the use of any of the compounds or compositions described herein for the preparation of medicaments that may be administered for such treatments, as well as to such compounds for the treatments disclosed and specified. In additional aspects, methods are provided for synthesizing the compounds described herein, with representative synthetic protocols and pathways described herein.

Accordingly, it is a principal object of the invention to provide compounds and compositions effective to treat certain anxiety or mood disorders including, for instance, depression and dysthymia. A still further object of the invention is to provide a method for reducing symptoms associated with an anxiety or mood disorder such as depression or dysthymia. Other objects and advantages will become apparent to those skilled in the art from a consideration of the ensuing detailed description.

BRIEF DESCRIPTION OF THE FIGURES

FIG. 7 demonstrates the effect of acute ivt. 6FNE on 1 h sucrose consumption (upper), sucrose preference (middle), and water consumption (lower panel) in 12 h water deprived mice at 48 h after LPS or vehicle administration. N=8-11/gp. *$p<0.001$, Bonferroni test.

This high prazosin dose is known to penetrate brain unlike the low (0.2 mg/kg) dose. *p<0.05 versus vehicle.

Figure 17A:
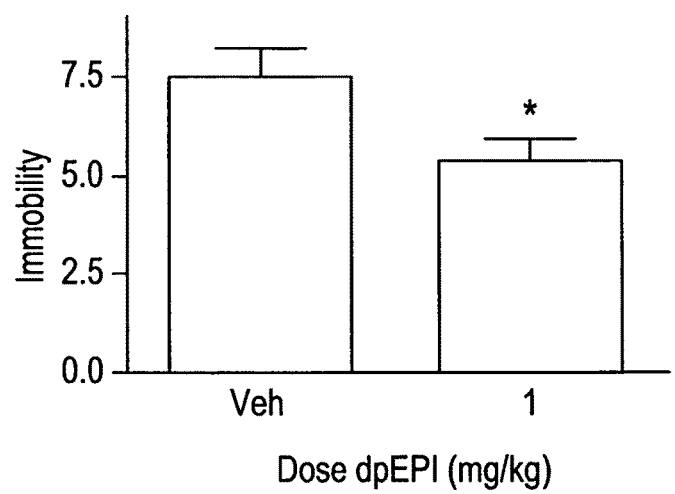
Figure 17B:
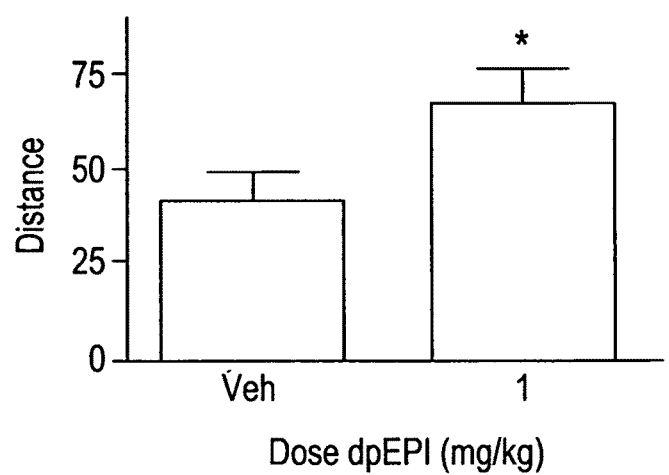

FIG. 17 demonstrates the positive antidepressant effect of i.p, injection of the related catecholamine pro-drug, dp-epinephrine (dpEPI, 1 mg/kg)/prazosin (0.2 mg/kg)+propranolol (0.5 mg/kg), 15 min prior to the RFS test. This result establishes that an immediate antidepressant effect in chronic depression is a unique property of this class of drugs. *p<0.05 versus Vehicle, t-test. N=9. *p<0.05 versus vehicle FIG. 18 demonstrates the effect of dp6FNE/prazosin (1 mg/kg) on endotoxin(LPS)-induced anhedonia of female urine sniffing test (FUST). N=6-8. *p<0.05 versus Control group.

Figure 19A:
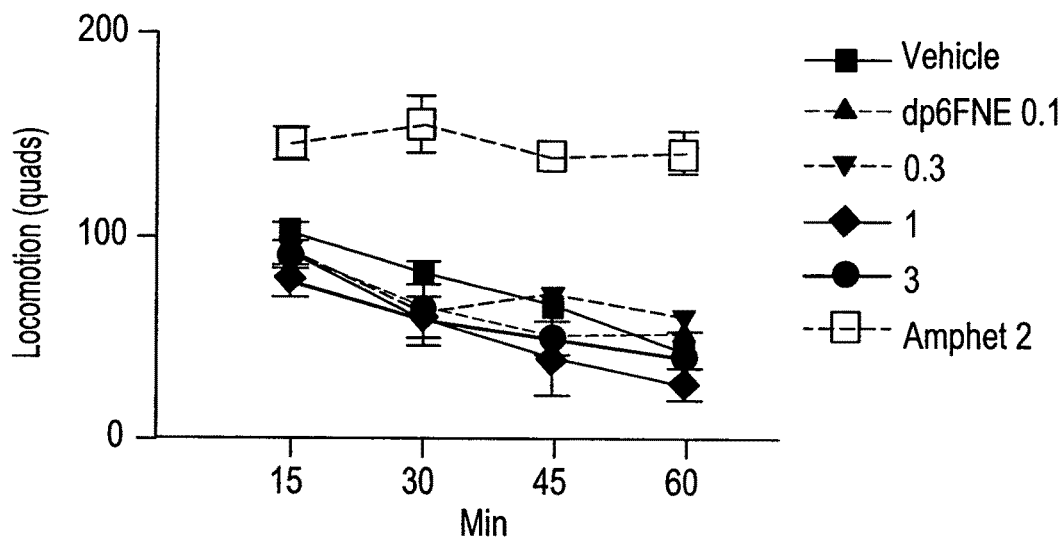
Figure 19B:
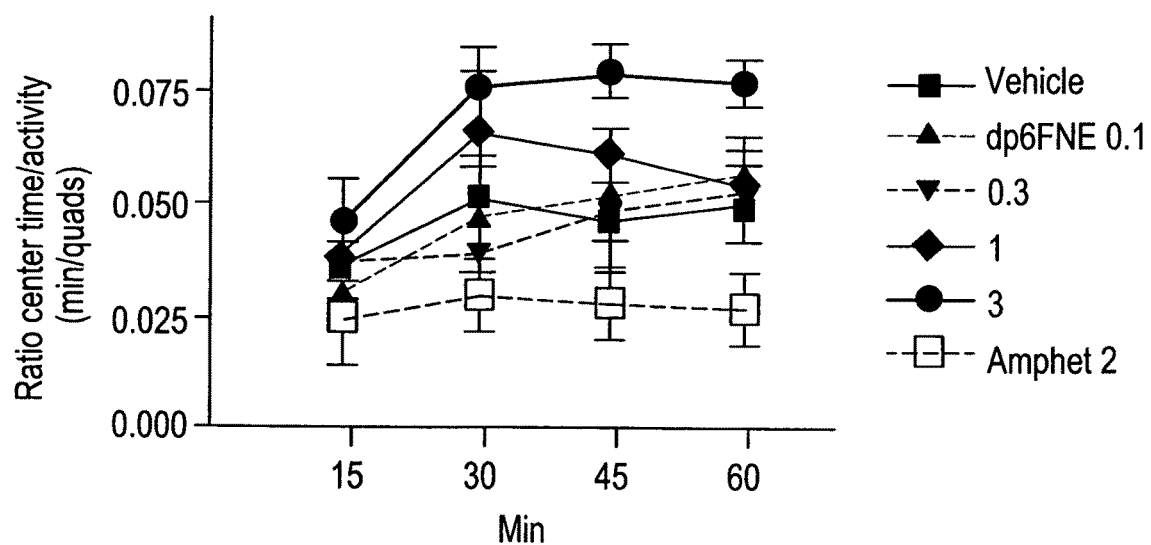

FIG. 19 demonstrates the effect of dp6FNE/prazosin on locomotor activity and anxiety, the latter measured by relative time in the center of the field, in an open field. Amphetamine was included for purposes of comparison. N=6-7/gp. dp6FNE had little or no effect on locomotor activity but increased time in the center of the field consistent with an anxiolytic effect. For statistics, see Results.

DETAILED DESCRIPTION OF THE INVENTION

Definitions

The following terms are intended to have the meanings presented therewith below and are useful in understanding the description and intended scope of the present invention.

When describing the invention, which may include compounds, pharmaceutical compositions containing such compounds and methods of using such compounds and compositions, the following terms, if present, have the following meanings unless otherwise indicated. It should also be understood that when described herein any of the moieties defined below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein.

The articles 'a' and 'an' may be used herein to refer to one or to more than one (i.e. at least one) of the grammatical objects of the article. By way of example 'an analogue' means one analogue or more than one analogue.

'Acyl' or 'Alkanoyl' refers to a radical —C(O)$R^{20}$, where $R^{20}$ is hydrogen, $C_1$-$C_8$ alkyl, $C_3$-$C_{10}$ cycloalkyl, $C_3$-$C_{10}$ cycloalkylmethyl, 4-10 membered heterocycloalkyl, aryl, arylalkyl, 5-10 membered heteroaryl or heteroarylalkyl as defined herein. Representative examples include, but are not limited to, formyl, acetyl, cyclohexylcarbonyl, cyclohexylmethylcarbonyl, benzoyl and benzylcarbonyl. Exemplary 'acyl' groups are —C(O)H, —C(O)—$C_1$-$C_8$ alkyl, —C(O)—$(CH_2)_t(C_6$-$C_{10}$ aryl), —C(O)—$(CH_2)_t$(5-10 membered heteroaryl), —C(O)—$(CH_2)_t(C_3$-$C_{10}$ cycloalkyl), and —C(O)—$(CH_2)_t$(4-10 membered heterocycloalkyl), wherein t is an integer from 0 to 4.

'Substituted Acyl' or 'Substituted Alkanoyl' refers to a radical —C(O)$R^{21}$, wherein $R^{21}$ is independently $C_1$-$C_8$ alkyl, substituted with halo or hydroxy; or $C_3$-$C_{10}$ cycloalkyl, 4-10 membered heterocycloalkyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Acylamino' refers to a radical —$NR^{22}$C(O)$R^{23}$, where $R^{22}$ is hydrogen, $C_1$-$C_8$ alkyl, $C_3$-$C_{10}$ cycloalkyl, 4-10 membered heterocycloalkyl, $C_6$-$C_{10}$ aryl, arylalkyl, 5-10 memberd heteroaryl or heteroarylalkyl and $R^{23}$ is hydrogen, $C_1$-$C_8$ alkyl, $C_3$-$C_{10}$ cycloalkyl, 4-10 membered heterocycloalkyl, $C_6$-$C_{10}$ aryl, arylalkyl, 5-10 membered heteroaryl or heteroarylalkyl, as defined herein. Exemplary 'acylamino' include, but are not limited to, formylamino, acetylamino, cyclohexylcarbonylamino, cyclohexylmethyl-carbonylamino, benzoylamino and benzylcarbonylamino. Particular exemplary 'acylamino' groups are —$NR^{24}$C(O)—$C_1$-$C_8$ alkyl, —$NR^{24}$C(O)—$(CH_2)_t(C_6$-$C_{10}$ aryl), —$NR^{24}$C(O)—$(CH_2)_t$(5-10 membered heteroaryl), —$NR^{24}$C(O)—$(CH_2)_t$($C_3$-$C_{10}$ cycloalkyl), and —$NR^{24}$C(O)—$(CH_2)_t$(4-10 membered heterocycloalkyl), wherein t is an integer from 0 to 4, and each $R^{24}$ independently represents H or $C_1$-$C_8$ alkyl.

'Substituted Acylamino' refers to a radical —$NR^{25}$C(O)$R^{26}$, wherein:

$R^{25}$ is independently

H, $C_1$-$C_8$ alkyl, substituted with halo or hydroxy; or $C_3$-$C_{10}$ cycloalkyl, 4-10 membered heterocycloalkyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; and $R^{26}$ is independently H, $C_1$-$C_8$ alkyl, substituted with halo or hydroxy; or $C_3$-$C_{10}$ cycloalkyl, 4-10 membered heterocycloalkyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxyl;

provided at least one of $R^{25}$ and $R^{26}$ is other than H.

'Acyloxy' refers to a radical —OC(O)$R^{27}$, where $R^{27}$ is hydrogen, $C_1$-$C_8$ alkyl, $C_3$-$C_{10}$ cycloalkyl, $C_3$-$C_{10}$ cycloalkylmethyl, 4-10 membered heterocycloalkyl, aryl, arylalkyl, 5-10 membered heteroaryl or heteroarylalkyl as defined herein. Representative examples include, but are not limited to, formyl, acetyl, cyclohexylcarbonyl, cyclohexylmethylcarbonyl, benzoyl and benzylcarbonyl. Exemplary 'acyl' groups are —C(O)H, —C(O)—$C_1$-$C_8$ alkyl, —C(O)—$(CH_2)_t(C_6$-$C_{10}$ aryl), —C(O)—$(CH_2)_t$(5-10 membered heteroaryl), —C(O)—$(CH_2)_t(C_3$-$C_{10}$ cycloalkyl), and —C(O)—$(CH_2)_t$(4-10 membered heterocycloalkyl), wherein t is an integer from 0 to 4.

'Substituted Acyloxy' refers to a radical —OC(O)$R^{28}$, wherein $R^{28}$ is independently $C_1$-$C_8$ alkyl, substituted with halo or hydroxy; or $C_3$-$C_{10}$ cycloalkyl, 4-10 membered heterocycloalkyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Alkoxy' refers to the group —O$R^{29}$ where $R^{29}$ is $C_1$-$C_8$ alkyl. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

'Substituted alkoxy' refers to an alkoxy group substituted with one or more of those groups recited in the definition of "substituted" herein, and particularly refers to an alkoxy group having 1 or more substituents, for instance from 1 to 5 substituents, and particularly from 1 to 3 substituents, in particular 1 substituent, selected from the group consisting of amino, substituted amino, $C_6$-$C_{10}$ aryl, aryloxy, carboxyl, cyano, $C_3$-$C_{10}$ cycloalkyl, 4-10 membered heterocycloalkyl, halogen, 5-10 membered heteroaryl, hydroxyl, nitro, thioalkoxy, thioaryloxy, thiol, alkyl-S(O)—, aryl-S(O)—, alkyl-S(O)$_2$— and aryl-S(O)$_2$—. Exemplary 'substituted alkoxy' groups are —O—(CH$_2$)$_t$(C$_6$-C$_{10}$ aryl), —O—(CH$_2$)$_t$(5-10 membered heteroaryl), —O—(CH$_2$)$_t$(C$_3$-C$_{10}$ cycloalkyl), and —O—(CH$_2$)$_t$(4-10 membered heterocycloalkyl), wherein t is an integer from 0 to 4 and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. Particular exemplary 'substituted alkoxy' groups are OCF$_3$, OCH$_2$CF$_3$, OCH$_2$Ph, OCH$_2$-cyclopropyl, OCH$_2$CH$_2$OH, and OCH$_2$CH$_2$NMe$_2$.

'Alkoxycarbonyl' refers to a radical —C(O)—OR$^{30}$ where R$^{30}$ represents an $C_1$-$C_8$ alkyl, $C_3$-$C_{10}$ cycloalkyl, $C_3$-$C_{10}$ cycloalkylalkyl, 4-10 membered heterocycloalkylalkyl, aralkyl, or 5-10 membered heteroarylalkyl as defined herein. Exemplary "alkoxycarbonyl" groups are C(O)O—$C_1$-$C_8$ alkyl, —C(O)O—(CH$_2$)$_t$(C$_6$-C$_{10}$ aryl), —C(O)O—(CH$_2$)$_t$(5-10 membered heteroaryl), —C(O)O—(CH$_2$)$_t$(C$_3$-C$_{10}$ cycloalkyl), and —C(O)—(CH$_2$)$_t$(4-10 membered heterocycloalkyl), wherein t is an integer from 1 to 4.

'Substituted Alkoxycarbonyl' refers to a radical —C(O)—OR$^{31}$ where R$^{31}$ represents:
$C_1$-$C_8$ alkyl, $C_3$-$C_{10}$ cycloalkyl, $C_3$-$C_{10}$ cycloalkylalkyl, or 4-10 membered heterocycloalkylalkyl, each of which is substituted with halo, substituted or unsubstituted amino, or hydroxy; or
$C_6$-$C_{10}$ aralkyl, or 5-10 membered heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxyl.

'Aryloxycarbonyl' refers to a radical —C(O)—OR$^{32}$ where R$^{32}$ represents an $C_6$-$C_{10}$ aryl, as defined herein. Exemplary "aryloxycarbonyl" groups is —C(O)O—(C$_6$-C$_{10}$ aryl).

'Substituted Aryloxycarbonyl' refers to a radical —C(O)—OR$^{33}$ where R$^{33}$ represents
$C_6$-$C_{10}$ aryl, substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxyl.

'Heteroaryloxycarbonyl' refers to a radical —C(O)—OR$^{34}$ where R$^{34}$ represents a 5-10 membered heteroaryl, as defined herein. An exemplary "aryloxycarbonyl" group is —C(O)O-(5-10 membered heteroaryl).

'Substituted Heteroaryloxycarbonyl' refers to a radical —C(O)—OR$^{35}$ where R$^{35}$ represents:
5-10 membered heteroaryl, substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxyl.

'Alkoxycarbonylamino' refers to the group —NR$^{36}$C(O)OR$^{37}$, where R$^{36}$ is hydrogen, $C_1$-$C_8$ alkyl, $C_3$-$C_{10}$ cycloalkyl, $C_3$-$C_{10}$ cycloalkylmethyl, 4-10 membered heterocycloalkyl, aryl, arylalkyl, 5-10 membered heteroaryl or heteroarylalkyl as defined herein, and R$^{37}$ is $C_1$-$C_8$ alkyl, $C_3$-$C_{10}$ cycloalkyl, $C_3$-$C_{10}$ cycloalkylmethyl, 4-10 membered heterocycloalkyl, aryl, arylalkyl, 5-10 membered heteroaryl or heteroarylalkyl as defined herein.

'Alkyl' means straight or branched aliphatic hydrocarbon having 1 to 20 carbon atoms. Particular alkyl has 1 to 12 carbon atoms. More particular is lower alkyl which has 1 to 6 carbon atoms. A further particular group has 1 to 4 carbon atoms. Exemplary straight chained groups include methyl, ethyl n-propyl, and n-butyl. Branched means that one or more lower alkyl groups such as methyl, ethyl, propyl or butyl is attached to a linear alkyl chain, exemplary branched chain groups include isopropyl, iso-butyl, t-butyl and isoamyl.

'Substituted alkyl' refers to an alkyl group as defined above substituted with one or more of those groups recited in the definition of "substituted" herein, and particularly refers to an alkyl group having 1 or more substituents, for instance from 1 to 5 substituents, and particularly from 1 to 3 substituents, in particular 1 substituent, selected from the group consisting of acyl, acylamino, acyloxy (—O-acyl or —OC(O)R$^{20}$), alkoxy, alkoxycarbonyl, alkoxycarbonylamino (—NR"-alkoxycarbonyl or —NH—C(O)—OR$^{27}$), amino, substituted amino, aminocarbonyl (carbamoyl or amido or —C(O)—NR"$_2$), aminocarbonylamino (—NR"-C(O)—NR"$_2$), aminocarbonyloxy (—O—C(O)—NR"$_2$), aminosulfonyl, sulfonylamino, aryl, aryloxy, azido, carboxyl, cyano, cycloalkyl, halogen, hydroxy, heteroaryl, nitro, thiol, —S-alkyl, —S-aryl, —S(O)-alkyl, —S(O)-aryl, —S(O)$_2$-alkyl, and —S(O)$_2$-aryl. In a particular embodiment 'substituted alkyl' refers to a $C_1$-$C_8$ alkyl group substituted with halo, cyano, nitro, trifluoromethyl, trifluoromethoxy, azido, —NR'''SO$_2$R'', —SO$_2$NR''R'''; —C(O)R'', —C(O)OR', —OC(O)R', —NR'''C(O)R'', —C(O)NR''R'''; —NR'''R''''; or —(CR'''R'''')$_m$ OR'''; wherein each R'' is independently selected from H, $C_1$-$C_8$ alkyl, —(CH$_2$)$_t$(C$_6$-C$_{10}$ aryl), —(CH$_2$)$_t$(5-10 membered heteroaryl), —(CH$_2$)$_t$(C$_3$-C$_{10}$ cycloalkyl), and —(CH$_2$)$_t$(4-10 membered heterocycloalkyl), wherein t is an integer from 0 to 4 and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted haloalkoxy or hydroxy. Each of R''' and R'''' independently represents H or $C_1$-$C_8$ alkyl.

'Alkylene' refers to divalent saturated alkene radical groups having 1 to 11 carbon atoms and more particularly 1 to 6 carbon atoms which can be straight-chained or branched. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

'Substituted alkylene' refers to those groups recited in the definition of "substituted" herein, and particularly refers to an alkylene group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

'Alkenyl' refers to monovalent olefinically unsaturated hydrocarbyl groups preferably having 2 to 11 carbon atoms, particularly, from 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH=CH$_2$), n-propenyl (—CH$_2$CH=CH$_2$), isopropenyl (—C(CH$_3$)=CH$_2$), vinyl and substituted vinyl, and the like.

'Substituted alkenyl' refers to those groups recited in the definition of 'substituted' herein, and particularly refers to an alkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano; cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

'Alkenylene' refers to divalent olefinically unsaturated hydrocarbyl groups particularly having up to about 11 carbon atoms and more particularly 2 to 6 carbon atoms which can be straight-chained or branched and having at least 1 and particularly from 1 to 2 sites of olefinic unsaturation. This term is exemplified by groups such as ethenylene (—CH=CH—), the propenylene isomers (e.g., —CH=CHCH$_2$— and —C(CH$_3$)=CH— and —CH=C(CH$_3$)—) and the like.

'Alkynyl' refers to acetylenically or alkynically unsaturated hydrocarbyl groups particularly having 2 to 11 carbon atoms, and more particularly 2 to 6 carbon atoms which can be straight-chained or branched and having at least 1 and particularly from 1 to 2 sites of alkynyl unsaturation. Particular non-limiting examples of alkynyl groups include acetylenic, ethynyl (—C≡CH), propargyl (—CH$_2$C≡CH), and the like.

'Substituted alkynyl' refers to those groups recited in the definition of "substituted" herein, and particularly refers to an alkynyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

'Amino' refers to the radical —NH$_2$.

'Substituted amino' refers to an amino group substituted with one or more of those groups recited in the definition of 'substituted' herein, and particularly refers to the group —N(R$^{38}$)$_2$ where each R$^{38}$ is independently selected from:
hydrogen, C$_1$-C$_8$ alkyl, C$_6$-C$_{10}$ aryl, 5-10 membered heteroaryl, 4-10 membered heterocycloalkyl, or C$_3$-C$_{10}$ cycloalkyl; or
C$_1$-C$_8$ alkyl, substituted with halo or hydroxy; or
—(CH$_2$)$_t$(C$_6$-C$_{10}$ aryl), —(CH$_2$)$_t$(5-10 membered heteroaryl), —(CH$_2$)$_t$(C$_3$-C$_{10}$ cycloalkyl) or —(CH$_2$)$_t$(4-10 membered heterocycloalkyl) wherein t is an integer between 0 and 8, each of which is substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy; or
both R$^{38}$ groups are joined to form an alkylene group.

When both R$^{38}$ groups are hydrogen, —N(R$^{38}$)$_2$ is an amino group. Exemplary 'substituted amino' groups are —NR$^{39}$—C$_1$-C$_8$ alkyl, —NR$^{39}$—(CH$_2$)$_t$(C$_6$-C$_{10}$ aryl), —NR$^{39}$—(CH$_2$)$_t$(5-10 membered heteroaryl), —NR$^{39}$—(CH$_2$)$_t$(C$_3$-C$_{10}$ cycloalkyl), and —NR$^{39}$—(CH$_2$)$_t$(4-10 membered heterocycloalkyl), wherein t is an integer from 0 to 4, each R$^{39}$ independently represents H or C$_1$-C$_8$ alkyl; and any alkyl groups present, may themselves be substituted by halo, substituted or unsubstituted amino, or hydroxy; and any aryl, heteroaryl, cycloalkyl or heterocycloalkyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy. For the avoidance of doubt the term "substituted amino" includes the groups alkylamino, substituted alkylamino, alkylarylamino, substituted alkylarylamino, arylamino, substituted arylamino, dialkylamino and substituted dialkylamino as defined below.

'Alkylamino' refers to the group —NHR$^{40}$, wherein R$^{40}$ is C$_1$-C$_8$ alkyl;

'Substituted Alkylamino' refers to the group —NHR$^{41}$, wherein R$^{41}$ is C$_1$-C$_8$ alkyl; and the alkyl group is substituted with halo, substituted or unsubstituted amino, hydroxy, C$_3$-C$_{10}$ cycloalkyl, 4-10 membered heterocycloalkyl, C$_6$-C$_{10}$ aryl, 5-10 membered heteroaryl, aralkyl or heteroaralkyl; and any aryl, heteroaryl, cycloalkyl or heterocycloalkyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

'Alkylarylamino' refers to the group —NR$^{42}$R$^{43}$, wherein R$^{42}$ is aryl and R$^{43}$ is C$_1$-C$_8$ alkyl.

'Substituted Alkylarylamino' refers to the group —NR$^{44}$R$^{45}$, wherein R$^{44}$ is aryl and R$^{45}$ is C$_1$-C$_8$ alkyl; and the alkyl group is substituted with halo, substituted or unsubstituted amino, hydroxy, C$_3$-C$_{10}$ cycloalkyl, 4-10 membered heterocycloalkyl, C$_6$-C$_{10}$ aryl, 5-10 membered heteroaryl, aralkyl or heteroaralkyl; and any aryl, heteroaryl, cycloalkyl or heterocycloalkyl groups present, may themselves be substituted by unsubstituted C$_1$-C$_4$ alkyl, halo, cyano, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

'Arylamino' means a radical —NHR$^{46}$ where R$^{46}$ is selected from C$_6$-C$_{10}$ aryl and 5-10 membered heteroaryl as defined herein.

'Substituted Arylamino' refers to the group —NHR$^{47}$, wherein R$^{47}$ is independently selected from C$_6$-C$_{10}$ aryl and 5-10 membered heteroaryl; and any aryl or heteroaryl groups present, may themselves be substituted by unsubstituted C$_1$-C$_4$ alkyl, halo, cyano, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

'Dialkylamino' refers to the group —NR$^{48}$R$^{49}$, wherein each of R$^{48}$ and R$^{49}$ are independently selected from C$_1$-C$_8$ alkyl.

'Substituted Dialkylamino' refers to the group —NR$^{50}$R$^{51}$, wherein each of R$^{59}$ and R$^{51}$ are independently selected from C$_1$-C$_8$ alkyl; and at least one of the alkyl groups is independently substituted with halo, hydroxy, C$_3$-C$_{10}$ cycloalkyl, 4-10 membered heterocycloalkyl, C$_6$-C$_{10}$ aryl, 5-10 membered heteroaryl, aralkyl or heteroaralkyl; and any aryl, heteroaryl, cycloalkyl or heterocycloalkyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

'Diarylamino' refers to the group —NR$^{52}$R$^{53}$, wherein each of R$^{52}$ and R$^{53}$ are independently selected from C$_6$-C$_{10}$ aryl.

'Aminosulfonyl' or 'Sulfonamide' refers to the radical —S(O)$_2$NH$_2$.

'Substituted aminosulfonyl' or 'substituted sulfonamide' refers to a radical such as —S(O$_2$)N(R$^{54}$)$_2$ wherein each R$^{548}$ is independently selected from:

H, C$_1$-C$_8$ alkyl, C$_3$-C$_{10}$ cycloalkyl, 4-10 membered heterocycloalkyl, C$_6$-C$_{10}$ aryl, aralkyl, 5-10 membered heteroaryl, and heteroaralkyl; or C$_1$-C$_8$ alkyl substituted with halo or hydroxy; or C$_3$-C$_{10}$ cycloalkyl, 4-10 membered heterocycloalkyl, C$_6$-C$_{10}$ aryl, aralkyl, 5-10 membered heteroaryl, or heteroaralkyl, each of which is substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy;

provided that at least one R$^{54}$ is other than H.

Exemplary 'substituted aminosulfonyl' or 'substituted sulfonamide' groups are —S(O$_2$)N(R$^{55}$)—C$_1$-C$_8$ alkyl, —S(O$_2$)N(R$^{55}$)—(CH$_2$)$_t$(C$_6$-C$_{10}$ aryl), —S(O$_2$)N(R$^{55}$)—(CH$_2$)$_t$(5-10 membered heteroaryl), —S(O$_2$)N(R$^{55}$)—(CH$_2$)$_t$(C$_3$-C$_{10}$ cycloalkyl), and —S(O$_2$)N(R$^{55}$)—(CH$_2$)$_t$(4-10 membered heterocycloalkyl), wherein t is an integer from 0 to 4; each R$^{55}$ independently represents H or C$_1$-C$_8$ alkyl; and any aryl, heteroaryl, cycloalkyl or heterocycloalkyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

'Aralkyl' or 'arylalkyl' refers to an alkyl group, as defined above, substituted with one or more aryl groups, as defined above. Particular aralkyl or arylalkyl groups are alkyl groups substituted with one aryl group.

'Substituted Aralkyl' or 'substituted arylalkyl' refers to an alkyl group, as defined above, substituted with one or more aryl groups; and at least one of the aryl groups present, may themselves be substituted by unsubstituted C$_1$-C$_4$ alkyl, halo, cyano, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

'Aryl' refers to a monovalent aromatic hydrocarbon group derived by the removal of one hydrogen atom from a single carbon atom of a parent aromatic ring system. In particular aryl refers to an aromatic ring structure, mono-cyclic or polycyclic that includes from 5 to 12 ring members, more usually 6 to 10. Where the aryl group is a monocyclic ring system it preferentially contains 6 carbon atoms. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene and trinaphthalene. Particularly aryl groups include phenyl, naphthyl, indenyl, and tetrahydronaphthyl.

'Substituted Aryl' refers to an aryl group substituted with one or more of those groups recited in the definition of 'substituted' herein, and particularly refers to an aryl group that may optionally be substituted with 1 or more substituents, for instance from 1 to 5 substituents, particularly 1 to 3 substituents, in particular 1 substituent. Particularly, 'Substituted Aryl' refers to an aryl group substituted with one or more of groups selected from halo, C$_1$-C$_8$ alkyl, C$_1$-C$_8$ haloalkyl, cyano, hydroxy, C$_1$-C$_8$ alkoxy, and amino.

Examples of representative substituted aryls include the following

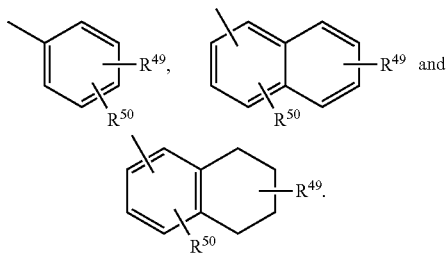

In these formulae one of R$^{56}$ and R$^{57}$ may be hydrogen and at least one of R$^{56}$ and R$^{57}$ is each independently selected from C$_1$-C$_8$ alkyl, C$_1$-C$_8$ haloalkyl, 4-10 membered heterocycloalkyl, alkanoyl, C$_1$-C$_8$ alkoxy, heteroaryloxy, alkylamino, arylamino, heteroarylamino, NR$^{58}$COR$^{59}$, NR$^{58}$SOR$^{59}$, NR$^{58}$SO$_2$R$^{59}$, COOalkyl, COOaryl, CONR$^{58}$R$^{59}$, CONR$^{58}$OR$^{59}$, NR$^{58}$R$^{59}$, SO$_2$NR$^{58}$R$^{59}$, S-alkyl, SOalkyl, SO$_2$alkyl, Saryl, SOaryl, SO$_2$aryl; or R$^{56}$ and R$^{57}$ may be joined to form a cyclic ring (saturated or unsaturated) from 5 to 8 atoms, optionally containing one or more heteroatoms selected from the group N, O or S. R$^{60}$, and R$^{61}$ are independently hydrogen, C$_1$-C$_8$ alkyl, C$_1$-C$_4$ haloalkyl, C$_3$-C$_{10}$ cycloalkyl, 4-10 membered heterocycloalkyl, C$_6$-C$_{10}$ aryl, substituted aryl, 5-10 membered heteroaryl.

'Fused Aryl' refers to an aryl having two of its ring carbon in common with a second aryl ring or with an aliphatic ring.

'Arylalkyloxy' refers to an —O-alkylaryl radical where alkylaryl is as defined herein.

'Substituted Arylalkyloxy' refers to an —O-alkylaryl radical where alkylaryl is as defined herein; and any aryl groups present, may themselves be substituted by unsubstituted C$_1$-C$_4$ alkyl, halo, cyano, unsubstituted C$_1$-C$_4$ alkoxy, unsubstituted C$_1$-C$_4$ haloalkyl, unsubstituted C$_1$-C$_4$ hydroxyalkyl, or unsubstituted haloalkoxy or hydroxy.

'Azido' refers to the radical —N$_3$.

'Carbamoyl or amido' refers to the radical —C(O)NH$_2$.

'Substituted Carbamoyl' or 'substituted amido' refers to the radical —C(O)N(R$^{62}$)$_2$ wherein each R$^{62}$ is independently H, C$_1$-C$_8$ alkyl, C$_3$-C$_{10}$ cycloalkyl, 4-10 membered heterocycloalkyl, C$_6$-C$_{10}$ aryl, aralkyl, 5-10 membered heteroaryl, and heteroaralkyl; or C$_1$-C$_8$ alkyl substituted with halo or hydroxy; or C$_3$-C$_{10}$ cycloalkyl, 4-10 membered heterocycloalkyl, C$_6$-C$_{10}$ aryl, aralkyl, 5-10 membered heteroaryl, or heteroaralkyl, each of which is substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy;

provided that at least one R$^{62}$ is other than H.

Exemplary 'Substituted Carbamoyl' groups are —C(O)NR$^{64}$—C$_1$-C$_8$ alkyl, —C(O)NR$^{64}$—(CH$_2$)$_t$(C$_6$-C$_{10}$ aryl), —C(O)N$^{64}$—(CH$_2$)$_t$(5-10 membered heteroaryl), —C(O)NR$^{64}$—(CH$_2$)$_t$(C$_3$-C$_{10}$ cycloalkyl), and —C(O)NR$^{64}$—(CH$_2$)$_t$(4-10 membered heterocycloalkyl), wherein t is an integer from 0 to 4, each R$^{64}$ independently represents H or C$_1$-C$_8$ alkyl and any aryl, heteroaryl, cycloalkyl or heterocycloalkyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy. 'Carboxy' refers to the radical —C(O)OH.

'Cycloalkyl' refers to cyclic non-aromatic hydrocarbyl groups having from 3 to 10 carbon atoms. Such cycloalkyl groups include, by way of example, single ring structures such as cyclopropyl, cyclobutyl, cyclopentyl, and cyclooctyl.

'Substituted cycloalkyl' refers to a cycloalkyl group as defined above substituted with one or more of those groups recited in the definition of 'substituted' herein, and particularly refers to a cycloalkyl group having 1 or more substituents, for instance from 1 to 5 substituents, and particularly from 1 to 3 substituents, in particular 1 substituent.

'Cyano' refers to the radical —CN.

'Halo' or 'halogen' refers to fluoro (F), chloro (Cl), bromo (Br) and iodo (I). Particular halo groups are either fluoro or chloro.

'Hetero' when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. heterocycloalkyl, aryl, e.g. heteroaryl, cycloalkenyl, e.g. cycloheteroalkenyl, and the like having from 1 to 5, and particularly from 1 to 3 heteroatoms.

'Heteroaryl' means an aromatic ring structure, mono-cyclic or polycyclic, that includes one or more heteroatoms and 5 to 12 ring members, more usually 5 to 10 ring members. The heteroaryl group can be, for example, a five membered or six membered monocyclic ring or a bicyclic structure formed from fused five and six membered rings or two fused six membered rings or, by way of a further example, two fused five membered rings. Each ring may contain up to four heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five. Examples of five membered monocyclic heteroaryl groups include but are not limited to pyrrole, furan, thiophene, imidazole, furazan, oxazole, oxadiazole, oxatriazole, isoxazole, thiazole, isothiazole, pyrazole, triazole and tetrazole groups. Examples of six membered monocyclic heteroaryl groups include but are not limited to pyridine, pyrazine, pyridazine, pyrimidine and triazine. Particular examples of bicyclic heteroaryl groups containing a five membered ring fused to another five membered ring include but are not limited to imidazothiazole and imidazoimidazole. Particular examples of bicyclic heteroaryl groups containing a six membered ring fused to a five membered ring include but are not limited to benzfuran, benzthiophene, benzimidazole, benzoxazole, isobenzoxazole, benzisoxazole, benzthiazole, benzisothiazole, isobenzofuran, indole, isoindole, isoindolone, indolizine, indoline, isoindoline, purine (e.g., adenine, guanine), indazole, pyrazolopyrimidine, triazolopyrimidine, benzodioxole and pyrazolopyridine groups. Particular examples of bicyclic heteroaryl groups containing two fused six membered rings include but are not limited to quinoline, isoquinoline, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups. Particular heteroaryl groups are those derived from thiophene, pyrrole, benzothiophene, benzofuran, indole, pyridine, quinoline, imidazole, oxazole and pyrazine.

Examples of representative heteroaryls include the following:

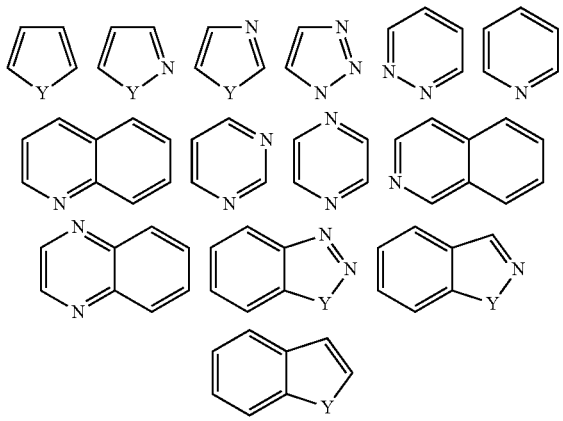

wherein each Y is selected from carbonyl, N, NR$^{65}$, O and S; and R$^{65}$ is independently hydrogen, C$_1$-C$_8$ alkyl, C$_3$-C$_{10}$ cycloalkyl, 4-10 membered heterocycloalkyl, C$_6$-C$_{10}$ aryl, and 5-10 membered heteroaryl.

Examples of representative aryl having hetero atoms containing substitution include the following:

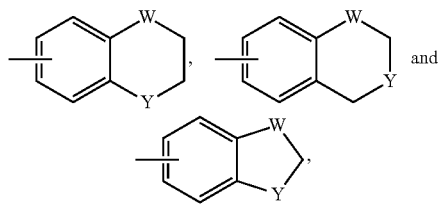

wherein each W is selected from C(R$^{66}$)$_2$, NR$^{66}$, O and S; and each Y is selected from carbonyl, NR$^{66}$, O and S; and R$^{66}$ is independently hydrogen, C$_1$-C$_8$ alkyl, C$_3$-C$_{10}$ cycloalkyl, 4-10 membered heterocycloalkyl, C$_6$-C$_{10}$ aryl, and 5-10 membered heteroaryl.

As used herein, the term 'heterocycloalkyl' refers to a 4-10 membered, stable heterocyclic non-aromatic ring and/or including rings containing one or more heteroatoms independently selected from N, O and S, fused thereto. A fused heterocyclic ring system may include carbocyclic rings and need only include one heterocyclic ring. Examples of heterocyclic rings include, but are not limited to, morpholine, piperidine (e.g. 1-piperidinyl, 2-piperidinyl, 3-piperidinyl and 4-piperidinyl), pyrrolidine (e.g. 1-pyrrolidinyl, 2-pyrrolidinyl and 3-pyrrolidinyl), pyrrolidone, pyran (2H-pyran or 4H-pyran), dihydrothiophene, dihydropyran, dihydrofuran, dihydrothiazole, tetrahydrofuran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazine, and N-alkyl piperazines such as N-methyl piperazine. Further examples include thiomorpholine and its S-oxide and S,S-dioxide (particularly thiomorpholine). Still further examples include azetidine, piperidone, piperazone, and N-alkyl piperidines such as N-methyl piperidine. Particular examples of heterocycloalkyl groups are shown in the following illustrative examples:

wherein each W is selected from CR$^{67}$, C(R$^{67}$)$_2$, NR$^{67}$, O and S; and each Y is selected from NR$^{67}$, O and S; and R$^{67}$ is independently hydrogen, C$_1$-C$_8$ alkyl, C$_3$-C$_{10}$ cycloalkyl, 4-10 membered heterocycloalkyl, C$_6$-C$_{10}$ aryl, 5-10 membered heteroaryl, These heterocycloalkyl rings may be optionally substituted with one or more groups selected from the group consisting of acyl, acylamino, acyloxy, alkoxy, alkoxycarbonyl, alkoxycarbonylamino, amino, substituted amino, aminocarbonyl (carbamoyl or amido), aminocarbonylamino, aminosulfonyl, sulfonylamino, aryl, aryloxy, azido, carboxyl, cyano, cycloalkyl, halogen, hydroxy, keto, nitro, thiol, —S-alkyl, —S-aryl, —S(O)-alkyl, —S(O)-aryl, —S(O)$_2$-alkyl, and —S(O)$_2$-aryl. Substituting groups include carbonyl or thiocarbonyl which provide, for example, lactam and urea derivatives.

'Hydroxy' refers to the radical —OH.

'Nitro' refers to the radical —NO$_2$.

'Substituted' refers to a group in which one or more hydrogen atoms are each independently replaced with the same or different substituent(s). Typical substituents may be selected from the group consisting of:

halogen, —R$^{68}$, —O$^-$, =O, —OR$^{68}$, —SR$^{68}$, —S$^-$, =S, —NR$^{68}$R$^{69}$, =NR$^{68}$, —CCl$_3$, —CF$_3$, —CN, —OCN, —SCN, —NO, —NO$_2$, =N$_2$, —N$_3$, —S(O)$_2$O$^-$, —S(O)$_2$OH, —S(O)$_2$R$^{68}$, —OS(O)$_2$O$^-$, —OS(O)$_2$R$^{68}$, —P(O)(O$^-$)$_2$, —P(O)(OR$^{68}$)(O$^-$), —OP(O)(OR$^{68}$)(OR$^{69}$), —C(O)R$^{68}$, —C(S)R$^{68}$, —C(O)OR$^{68}$, —C(O)NR$^{68}$R$^{69}$, —C(O)O$^-$, —C(S)OR$^{68}$, —NR$^{70}$C(O)NR$^{68}$R$^{69}$, —NR$^{70}$C(S)NR$^{68}$R$^{69}$, —NR$^{71}$C(NR$^{70}$)NR$^{68}$R$^{69}$ and —C(NR$^{70}$)NR$^{68}$R$^{69}$;

wherein each R$^{68}$, R$^{69}$, R$^{70}$ and R$^{71}$ are independently:
hydrogen, C$_1$-C$_8$ alkyl, C$_6$-C$_{10}$ aryl, arylalkyl, C$_3$-C$_{10}$ cycloalkyl, 4-10 membered heterocycloalkyl, 5-10 membered heteroaryl, heteroarylalkyl; or C$_1$-C$_8$ alkyl substituted with halo or hydroxy; or C$_6$-C$_{10}$ aryl, 5-10 membered heteroaryl, C$_6$-C$_{10}$ cycloalkyl or 4-10 membered heterocycloalkyl each of which is substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

In a particular embodiment, substituted groups are substituted with one or more substituents, particularly with 1 to 3 substituents, in particular with one substituent group.

In a further particular embodiment the substituent group or groups are selected from halo, cyano, nitro, trifluoromethyl, trifluoromethoxy, azido, —NR$^{72}$SO$_2$R$^{73}$, —SO$_2$NR$^{73}$R$^{72}$, —C(O)R$^{73}$, —C(O)OR$^{73}$, —OC(O)R$^{73}$, —NR$^{72}$C(O)R$^{73}$, —C(O)NR$^{73}$R$^{72}$, —NR$^{73}$R$^{72}$, —(CR$^{72}$R$^{72}$)$_m$OR$^{72}$, wherein, each R$^{73}$ is independently selected from H, C$_1$-C$_8$ alkyl, —(CH$_2$)$_t$(C$_6$-C$_{10}$ aryl), —(CH$_2$)$_t$(5-10 membered heteroaryl), —(CH$_2$)$_t$(C$_3$-C$_{10}$ cycloalkyl), and —(CH$_2$)$_t$(4-10 membered heterocycloalkyl), wherein t is an integer from 0 to 4; and any alkyl groups present, may themselves be substituted by halo or hydroxy; and any aryl, heteroaryl, cycloalkyl or heterocycloalkyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

Each R" independently represents H or C$_1$-C$_6$alkyl.

'Substituted sulfanyl' refers to the group —SR$^{74}$, wherein R$^{74}$ is selected from:

C$_1$-C$_8$ alkyl, C$_3$-C$_{10}$ cycloalkyl, 4-10 membered heterocycloalkyl, C$_6$-C$_{10}$ aryl, aralkyl, 5-10 membered heteroaryl, and heteroaralkyl; or C$_1$-C$_8$ alkyl substituted with halo, substituted or unsubstituted amino, or hydroxy; or C$_3$-C$_{10}$ cycloalkyl, 4-10 membered heterocycloalkyl, C$_6$-C$_{10}$ aryl, aralkyl, 5-10 membered heteroaryl, or heteroaralkyl, each of which is substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy.

Exemplary 'substituted sulfanyl' groups are —S—(C$_1$-C$_8$ alkyl) and —S—(C$_3$-C$_{10}$ cycloalkyl), —S—(CH$_2$)$_t$(C$_6$-C$_{10}$ aryl), —S—(CH$_2$)$_t$(5-10 membered heteroaryl), —S—(CH$_2$)$_t$(C$_3$-C$_{10}$ cycloalkyl), and —S—(CH$_2$)$_t$(4-10 membered heterocycloalkyl), wherein t is an integer from 0 to 4 and any aryl, heteroaryl, cycloalkyl or heterocycloalkyl groups present, may themselves be substituted by unsubstituted C$_1$-C$_4$ alkyl, halo, unsubstituted C$_1$-C$_4$ alkoxy, unsubstituted C$_1$-C$_4$ haloalkyl, unsubstituted C$_1$-C$_4$ hydroxyalkyl, or unsubstituted C$_1$-C$_4$ haloalkoxy or hydroxy. The term 'substituted sulfanyl' includes the groups 'alkylsulfanyl' or 'alkylthio', 'substituted alkylthio' or 'substituted alkylsulfanyl', 'cycloalkylsulfanyl' or 'cycloalkylthio', 'substituted cycloalkylsulfanyl' or 'substituted cycloalkylthio', 'arylsulfanyl' or 'arylthio' and 'heteroarylsulfanyl' or 'heteroarylthio' as defined below.

'Alkylthio' or 'Alkylsulfanyl' refers to a radical —SR$^{75}$ where R$^{75}$ is a C$_1$-C$_8$ alkyl or group as defined herein. Representative examples include, but are not limited to, methylthio, ethylthio, propylthio and butylthio.

'Substituted Alkylthio' or 'substituted alkylsulfanyl' refers to the group —SR$^{76}$ where R$^{76}$ is a C$_1$-C$_8$ alkyl, substituted with halo, substituted or unsubstituted amino, or hydroxy.

'Cycloalkylthio' or 'Cycloalkylsulfanyl' refers to a radical —SR$^{77}$ where R$^{77}$ is a C$_3$-C$_{10}$ cycloalkyl or group as defined herein. Representative examples include, but are not limited to, cyclopropylthio, cyclohexylthio, and cyclopentylthio.

'Substituted cycloalkylthio' or 'substituted cycloalkylsulfanyl' refers to the group —SR$^{78}$ where R$^{78}$ is a C$_3$-C$_{10}$ cycloalkyl, substituted with halo, substituted or unsubstituted amino, or hydroxy.

'Arylthio' or 'Arylsulfanyl' refers to a radical —SR$^{79}$ where R$^{79}$ is a C$_6$-C$_{10}$ aryl group as defined herein.

'Heteroarylthio' or 'Heteroarylsulfanyl' refers to a radical —SR$^{80}$ where R$^{80}$ is a 5-10 membered heteroaryl group as defined herein.

'Substituted sulfinyl' refers to the group —S(O)R$^{81}$, wherein R$^{81}$ is selected from:

C$_1$-C$_8$ alkyl, C$_3$-C$_{10}$ cycloalkyl, 4-10 membered heterocycloalkyl, C$_6$-C$_{10}$ aryl, aralkyl, 5-10 membered heteroaryl, and heteroaralkyl; or $C_1$-$C_8$ alkyl substituted with halo, substituted or unsubstituted amino, or hydroxy; or $C_3$-$C_{10}$ cycloalkyl, 4-10 membered heterocycloalkyl, $C_6$-$C_{10}$ aryl, aralkyl, 5-10 membered heteroaryl, or heteroaralkyl, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

Exemplary 'substituted sulfinyl' groups are —S(O)—($C_1$-$C_8$ alkyl) and —S(O)—($C_3$-$C_{10}$ cycloalkyl), —S(O)—$(CH_2)_t$($C_6$-$C_{10}$ aryl), —S(O)—$(CH_2)_t$(5-10 membered heteroaryl), —S(O)—$(CH_2)_t$($C_3$-$C_{10}$ cycloalkyl), and —S(O)—$(CH_2)_t$(4-10 membered heterocycloalkyl), wherein t is an integer from 0 to 4 and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. The term substituted sulfinyl includes the groups 'alkylsulfinyl', 'substituted alkylsulfinyl', 'cycloalkylsulfinyl', 'substituted cycloalkylsulfinyl', 'arylsulfinyl' and 'heteroarylsulfinyl' as defined herein.

'Alkylsulfinyl' refers to a radical —S(O)$R^{82}$ where $R^{82}$ is a $C_1$-$C_8$ alkyl group as defined herein. Representative examples include, but are not limited to, methylsulfinyl, ethylsulfinyl, propylsulfinyl and butylsulfinyl.

'Substituted Alkylsulfinyl' refers to a radical —S(O)$R^{83}$ where $R^{83}$ is a $C_1$-$C_8$ alkyl group as defined herein, substituted with halo, substituted or unsubstituted amino, or hydroxy.

'Cycloalkylsulfinyl' refers to a radical —S(O)$R^{84}$ where $R^{84}$ is a $C_3$-$C_{10}$ cycloalkyl or group as defined herein. Representative examples include, but are not limited to, cyclopropylsulfinyl, cyclohexylsulfinyl, and cyclopentylsulfinyl. Exemplary 'cycloalkylsulfinyl' groups are S(O)—$C_3$-$C_{10}$ cycloalkyl.

'Substituted cycloalkylsulfinyl' refers to the group —S(O)$R^{85}$ where $R^{85}$ is a $C_3$-$C_{10}$ cycloalkyl, substituted with halo, substituted or unsubstituted amino, or hydroxy.

'Arylsulfinyl' refers to a radical —S(O)$R^{86}$ where $R^{86}$ is a $C_6$-$C_{10}$ aryl group as defined herein.

'Heteroarylsulfinyl' refers to a radical —S(O)$R^{87}$ where $R^{87}$ is a 5-10 membered heteroaryl group as defined herein.

'Substituted sulfonyl' refers to the group —S(O)$_2$$R^{88}$, wherein $R^{88}$ is selected from:

$C_1$-$C_8$ alkyl, $C_3$-$C_{10}$ cycloalkyl, 4-10 membered heterocycloalkyl, $C_6$-$C_{10}$ aryl, aralkyl, 5-10 membered heteroaryl, and heteroaralkyl; or $C_1$-$C_8$ alkyl substituted with halo, substituted or unsubstituted amino, or hydroxy; or $C_3$-$C_{10}$ cycloalkyl, 4-10 membered heterocycloalkyl, $C_6$-$C_{10}$ aryl, aralkyl, 5-10 membered heteroaryl, or heteroaralkyl, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

Exemplary 'substituted sulfonyl' groups are —S(O)$_2$—($C_1$-$C_8$ alkyl) and —S(O)$_2$—($C_3$-$C_{10}$ cycloalkyl), —S(O)$_2$—$(CH_2)_t$($C_6$-$C_{10}$ aryl), —S(O)$_2$—$(CH_2)_t$(5-10 membered heteroaryl), —S(O)$_2$—$(CH_2)_t$($C_3$-$C_{10}$ cycloalkyl), and —S(O)$_2$—$(CH_2)_t$(4-10 membered heterocycloalkyl), wherein t is an integer from 0 to 4 and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. The term substituted sulfonyl includes the groups alkylsulfonyl, substituted alkylsulfonyl, cycloalkylsulfonyl, substituted cycloalkylsulfonyl, arylsulfonyl and heteroarylsulfonyl.

'Alkylsulfonyl' refers to a radical —S(O)$_2$$R^{89}$ where $R^{89}$ is an $C_1$-$C_8$ alkyl group as defined herein. Representative examples include, but are not limited to, methylsulfonyl, ethylsulfonyl, propylsulfonyl and butylsulfonyl.

'Substituted Alkylsulfonyl' refers to a radical —S(O)$_2$$R^{90}$ where $R^{90}$ is an $C_1$-$C_8$ alkyl group as defined herein, substituted with halo, substituted or unsubstituted amino, or hydroxy.

'Cycloalkylsulfonyl' refers to a radical —S(O)$_2$$R^{91}$ where $R^{91}$ is a $C_3$-$C_{10}$ cycloalkyl or group as defined herein. Representative examples include, but are not limited to, cyclopropylsulfonyl, cyclohexylsulfonyl, and cyclopentylsulfonyl.

'Substituted cycloalkylsulfonyl' refers to the group —S(O)$_2$ $R^{92}$ where $R^{92}$ is a $C_3$-$C_{10}$ cycloalkyl, substituted with halo, substituted or unsubstituted amino, or hydroxy.

'Arylsulfonyl' refers to a radical —S(O)$_2$$R^{93}$ where $R^{93}$ is an $C_6$-$C_{10}$ aryl group as defined herein.

'Heteroarylsulfonyl' refers to a radical —S(O)$_2$$R^{94}$ where $R^{94}$ is an 5-10 membered heteroaryl group as defined herein.

'Sulfo' or 'sulfonic acid' refers to a radical such as —SO$_3$H.

'Substituted sulfo' or 'sulfonic acid ester' refers to the group —S(O)$_2$O$R^{95}$, wherein $R^{95}$ is selected from:

$C_1$-$C_8$ alkyl, $C_3$-$C_{10}$ cycloalkyl, 4-10 membered heterocycloalkyl, $C_6$-$C_{10}$ aryl, aralkyl, 5-10 membered heteroaryl, and heteroaralkyl; or $C_1$-$C_8$ alkyl substituted with halo, substituted or unsubstituted amino, or hydroxy; or $C_3$-$C_{10}$ cycloalkyl, 4-10 membered heterocycloalkyl, $C_6$-$C_{10}$ aryl, aralkyl, 5-10 membered heteroaryl, or heteroaralkyl, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

Exemplary 'Substituted sulfo' or 'sulfonic acid ester' groups are —S(O)$_2$—O—($C_1$-$C_8$ alkyl) and —S(O)$_2$—O—($C_3$-$C_{10}$ cycloalkyl), —S(O)$_2$—O—$(CH_2)_t$($C_6$-$C_{10}$ aryl), —S(O)$_2$—O—$(CH_2)_t$(5-10 membered heteroaryl), —S(O)$_2$—O—$(CH_2)_t$($C_3$-$C_{10}$ cycloalkyl), and —S(O)$_2$—O—$(CH_2)_t$(4-10 membered heterocycloalkyl), wherein t is an integer from 0 to 4 and any aryl, heteroaryl, cycloalkyl or heterocycloalkyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

'Thiol' refers to the group —SH.

'Aminocarbonylamino' refers to the group —N$R^{96}$C(O)N$R^{96}$$R^{96}$ where each $R^{96}$ is independently hydrogen $C_1$-$C_8$ alkyl, $C_3$-$C_{10}$ cycloalkyl, 4-10 membered heterocycloalkyl, $C_6$-$C_{10}$ aryl, aralkyl, 5-10 membered heteroaryl, and heteroaralkyl, as defined herein; or where two $R^{96}$ groups, when attached to the same N, are joined to form an alkylene group.

'Bicycloaryl' refers to a monovalent aromatic hydrocarbon group derived by the removal of one hydrogen atom from a single carbon atom of a parent bicycloaromatic ring system. Typical bicycloaryl groups include, but are not limited to, groups derived from indane, indene, naphthalene, tetrahydronaphthalene, and the like. Particularly, an aryl group comprises from 8 to 11 carbon atoms.

'Bicycloheteroaryl' refers to a monovalent bicycloheteroaromatic group derived by the removal of one hydrogen atom from a single atom of a parent bicycloheteroaromatic ring system. Typical bicycloheteroaryl groups include, but are not limited to, groups derived from benzofuran, benzimidazole, benzindazole, benzdioxane, chromene, chromane, cinnoline, phthalazine, indole, indoline, indolizine, isobenzofuran, isochromene, isoindole, isoindoline, isoquinoline, benzothiazole, benzoxazole, naphthyridine, benzoxadiazole, pteridine, purine, benzopyran, benzpyrazine, pyridopyrimidine, quinazoline, quinoline, quinolizine, quinoxaline, benzomorphan, tetrahydroisoquinoline, tetrahydroquinoline, and the like. Preferably, the bicycloheteroaryl group is between 9-11 membered bicycloheteroaryl, with 5-10 membered heteroaryl being particularly preferred. Particular bicycloheteroaryl groups are those derived from benzothiophene, benzofuran, benzothiazole, indole, quinoline, isoquinoline, benzimidazole, benzoxazole and benzdioxane.

'Compounds of the present invention', and equivalent expressions, are meant to embrace the compounds as herein described, in particular compounds according to any of the formulae herein described, which expression includes the prodrugs, the pharmaceutically acceptable salts, and the solvates, e.g., hydrates, where the context so permits. Similarly, reference to intermediates, whether or not they themselves are claimed, is meant to embrace their salts, and solvates, where the context so permits.

'Cycloalkylalkyl' refers to a radical in which a cycloalkyl group is substituted for a hydrogen atom of an alkyl group. Typical cycloalkylalkyl groups include, but are not limited to, cyclopropylmethyl, cyclobutylmethyl, cyclopentylmethyl, cyclohexylmethyl, cycloheptylmethyl, cyclooctylmethyl, cyclopropylethyl, cyclobutylethyl, cyclopentylethyl, cyclohexylethyl, cycloheptylethyl, and cyclooctylethyl, and the like.

'Heterocycloalkylalkyl' refers to a radical in which a heterocycloalkyl group is substituted for a hydrogen atom of an alkyl group. Typical heterocycloalkylalkyl groups include, but are not limited to, pyrrolidinylmethyl, piperidinylmethyl, piperazinylmethyl, morpholinylmethyl, pyrrolidinylethyl, piperidinylethyl, piperazinylethyl, morpholinylethyl, and the like.

'Cycloalkenyl' refers to cyclic hydrocarbyl groups having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

'Substituted cycloalkenyl' refers to those groups recited in the definition of "substituted" herein, and particularly refers to a cycloalkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$, 'Fused Cycloalkenyl' refers to a cycloalkenyl having two of its ring carbon atoms in common with a second aliphatic or aromatic ring and having its olefinic unsaturation located to impart aromaticity to the cycloalkenyl ring.

'Ethenyl' refers to substituted or unsubstituted —(C=C)—.

'Ethylene' refers to substituted or unsubstituted —(C—C)—.

'Ethynyl' refers to —(C≡C)—.

'Hydrogen bond donor' group refers to a group containg O—H, or N—H functionality. Examples of 'hydrogen bond donor' groups include —OH, —NH$_2$, and —NH—R$^{97}$ and wherein R$^{97}$ is alkyl, acyl, cycloalkyl, aryl, or heteroaryl.

'Dihydroxyphosphoryl' refers to the radical —PO(OH)$_2$.

'Substituted dihydroxyphosphoryl' refers to those groups recited in the definition of "substituted" herein, and particularly refers to a dihydroxyphosphoryl radical wherein one or both of the hydroxyl groups are substituted. Suitable substituents are described in detail below.

'Aminohydroxyphosphoryl' refers to the radical —PO (OH)NH$_2$.

'Substituted aminohydroxyphosphoryl' refers to those groups recited in the definition of "substituted" herein, and particularly refers to an aminohydroxyphosphoryl wherein the amino group is substituted with one or two substituents. Suitable substituents are described in detail below. In certain embodiments, the hydroxyl group can also be substituted.

'Nitrogen-Containing Heterocycloalkyl' group means a 4 to 7 membered non-aromatic cyclic group containing at least one nitrogen atom, for example, but without limitation, morpholine, piperidine (e.g. 2-piperidinyl, 3-piperidinyl and 4-piperidinyl), pyrrolidine (e.g. 2-pyrrolidinyl and 3-pyrrolidinyl), azetidine, pyrrolidone, imidazoline, imidazolidinone, 2-pyrazoline, pyrazolidine, piperazine, and N-alkyl piperazines such as N-methyl piperazine. Particular examples include azetidine, piperidone and piperazone.

'Thioketo' refers to the group =S.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

'Pharmaceutically acceptable' means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

'Pharmaceutically acceptable salt' refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term "pharmaceutically acceptable cation" refers to an acceptable cationic counter-ion of an acidic functional group. Such cations are exemplified by sodium, potassium, calcium, magnesium, ammonium, tetraalkylammonium cations, and the like.

'Pharmaceutically acceptable vehicle' refers to a diluent, adjuvant, excipient or carrier with which a compound of the invention is administered.

'Prodrugs' refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

'Solvate' refers to forms of the compound that are associated with a solvent, usually by a solvolysis reaction. This physical association includes hydrogen bonding. Conventional solvents include water, ethanol, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. 'Solvate' encompasses both solution-phase and isolable solvates. Representative solvates include hydrates, ethanolates and methanolates.

'Subject' includes humans. The terms 'human', 'patient' and 'subject' are used interchangeably herein.

'Therapeutically effective amount' means the amount of a compound that, when administered to a subject for treating a disease, is sufficient to effect such treatment for the disease. The 'therapeutically effective amount' can vary depending on the compound, the disease and its severity, and the age, weight, etc., of the subject to be treated.

'Preventing' or 'prevention' refers to a reduction in risk of acquiring or developing a disease or disorder (i.e., causing at least one of the clinical symptoms of the disease not to develop in a subject that may be exposed to a disease-causing agent, or predisposed to the disease in advance of disease onset.

The term 'prophylaxis' is related to 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

'Treating' or 'treatment' of any disease or disorder refers, in one embodiment, to ameliorating the disease or disorder (i.e., arresting the disease or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or disorder, either physically, (e.g., stabilization of a discernible symptom), physiologically, (e.g., stabilization of a physical parameter), or both. In a further embodiment, "treating" or "treatment" relates to slowing the progression of the disease.

'Compounds of the present invention', and equivalent expressions, are meant to embrace compounds of the Formula (e) as hereinbefore described, which expression includes the prodrugs, the pharmaceutically acceptable salts, and the solvates, e.g., hydrates, where the context so permits. Similarly, reference to intermediates, whether or not they themselves are claimed, is meant to embrace their salts, and solvates, where the context so permits.

When ranges are referred to herein, for example but without limitation, $C_1$-$C_8$ alkyl, the citation of a range should be considered a representation of each member of said range.

Other derivatives of the compounds of this invention have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are particular prodrugs. In some cases it is desirable to prepare double ester type prodrugs such as (acyloxy)alkyl esters or ((alkoxycarbonyl)oxy)alkylesters. Particularly the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

As used herein, the term 'isotopic variant' refers to a compound that contains unnatural proportions of isotopes at one or more of the atoms that constitute such compound. For example, an 'isotopic variant' of a compound can contain one or more non-radioactive isotopes, such as for example, deuterium ($^2$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Further, compounds may be prepared that are substituted with positron emitting isotopes, such as $^{11}$C, $^{18}$F, $^{15}$O and $^{13}$N, and would be useful in Positron Emission Topography (PET) studies for examining substrate receptor occupancy.

All isotopic variants of the compounds provided herein, radioactive or not, are intended to be encompassed within the scope of the invention.

It is also to be understood that compounds that have the same molecular formula but differ in the nature or sequence of bonding of their atoms or the arrangement of their atoms in space are termed 'isomers'. Isomers that differ in the arrangement of their atoms in space are termed 'stereoisomers'.

Stereoisomers that are not mirror images of one another are termed 'diastereomers' and those that are non-superimposable mirror images of each other are termed 'enantiomers'. When a compound has an asymmetric center, for example, it is bonded to four different groups, a pair of enantiomers is possible. An enantiomer can be characterized by the absolute configuration of its asymmetric center and is described by the R- and S-sequencing rules of Calm and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a 'racemic mixture'.

'Tautomers' refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

As used herein a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer. In certain embodiments, the weights are based upon total weight of all enantiomers or stereoisomers of the compound.

As used herein and unless otherwise indicated, the term "enantiomerically pure R-compound" refers to at least about 80% by weight R-compound and at most about 20% by weight S-compound, at least about 90% by weight R-compound and at most about 10% by weight S-compound, at least about 95% by weight R-compound and at most about 5% by weight S-compound, at least about 99% by weight R-compound and at most about 1% by weight S-compound, at least about 99.9% by weight R-compound or at most about 0.1% by weight S-compound. In certain embodiments, the weights are based upon total weight of compound.

As used herein and unless otherwise indicated, the term "enantiomerically pure S-compound" or "S-compound" refers to at least about 80% by weight S-compound and at most about 20% by weight R-compound, at least about 90% by weight S-compound and at most about 10% by weight R-compound, at least about 95% by weight S-compound and at most about 5% by weight R-compound, at least about 99% by weight S-compound and at most about 1% by weight R-compound or at least about 99.9% by weight S-compound and at most about 0.1% by weight R-compound. In certain embodiments, the weights are based upon total weight of compound.

In the compositions provided herein, an enantiomerically pure compound or a pharmaceutically acceptable salt, solvate, hydrate or prodrug thereof can be present with other active or inactive ingredients. For example, a pharmaceutical composition comprising enantiomerically pure R-compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

The compounds of this invention may possess one or more asymmetric centers; such compounds can therefore be produced as individual (R)- or (S)-stereoisomers or as mixtures thereof.

"Full Agonist" refers to a compound that binds (has affinity for) and activates a receptor, displaying substantially full efficacy at that receptor. One example of a drug that acts as a full agonist is isoproterenol, which mimics the action of adrenaline at β adrenoreceptors. Another example is morphine, which mimics the actions of endorphins at μ-opioid receptors throughout the central nervous system. A "full agonist" may be distinguished from a "partial agonist" (such as buspirone, aripiprazole, buprenorphine, or norclozapine) that also binds and activates a given receptor, but has only partial efficacy at the receptor relative to a full agonist. One study of benzodiazepine active sedative hypnotics found that partial agonists may have just under half the strength of full agonists.

"An additional α-adrenergic modulator" refers to a compound that binds or has affinity for an α-adrenergeric receptor or adrenoceptor and serves to modulate the activity of that receptor either as a full agonist, a partial agonist, a full antagonist or a partial antagonist.

"Enzymatically cleavable group" refers to a functional group that, in the presence of one or more enzymes, may be removed or separated from the remaining part of a molecule. Representative examples include esters with carboxylic acids. Particular examples include esters with amino acids. Further representative examples include acyl, alkoxycarbonyl, aryloxycarbonyl, heteroaryloxycarbonyl, aroyl, or heteroaroyl. Some particular enzylmatically cleavable groups include —CO-alkyl, CO-(substituted or unsubstituted alkyl), —CO-(substituted or unsubstituted aryl), or CO-(substituted or unsubstituted heteroaryl). Further particular enzylmatically cleavable groups include CO-Me, COEt, CO-t-Bu, CO-benzyl, or COPh.

Mood disorder is the term given for a group of diagnoses in the Diagnostic and Statistical Manual of Mental Disorders (DSM IV TR) classification system where a disturbance in the person's mood is hypothesized to be the main underlying feature. The classification is known as mood (affective) disorders in ICD 10. Two groups of mood disorders are broadly recognized; the division is based on whether the person has ever had a manic or hypomanic episode. Thus, there are depressive disorders, of which the best known and most researched is major depressive disorder (MDD) commonly called clinical depression or major depression, and bipolar disorder (BD), formerly known as "manic depression" and described by intermittent periods of manic and depressed episodes.

Depressive disorders include "Major depressive disorder (MDD)" commonly called major depression, unipolar depression, or clinical depression, where a person has two or more major depressive episodes. Depression without periods of mania is sometimes referred to as unipolar depression because the mood remains at one emotional state or "pole". Diagnosticians recognize several subtypes or course specifiers: Atypical depression (AD) is characterized by mood reactivity (paradoxical anhedonia) and positivity, significant weight gain or increased appetite ("comfort eating"), excessive sleep or somnolence (hypersomnia), a sensation of heaviness in limbs known as leaden paralysis, and significant social impairment as a consequence of hypersensitivity to perceived interpersonal rejection. Difficulties in measuring this subtype have led to questions of its validity and prevalence. Melancholic depression is characterized by a loss of pleasure (anhedonia) in most or all activities, a failure of reactivity to pleasurable stimuli, a quality of depressed mood more pronounced than that of grief or loss, a worsening of symptoms in the morning hours, early morning waking, psychomotor retardation, excessive weight loss (not to be confused with anorexia nervosa), or excessive guilt. Psychotic major depression (PMD), or simply psychotic depression, is the term for a major depressive episode, particularly of melancholic nature, where the patient experiences psychotic symptoms such as delusions or, less commonly, hallucinations. These are most commonly mood-congruent (content coincident with depressive themes). Catatonic depression is a rare and severe form of major depression involving disturbances of motor behavior and other symptoms. Here the person is mute and almost stuporose, and either immobile or exhibits purposeless or even bizarre movements. Catatonic symptoms also occur in schizophrenia, a manic episode, or be due to neuroleptic malignant syndrome. Postpartum depression (PPD) is listed as a course specifier in DSM-IV-TR; it refers to the intense, sustained and sometimes disabling depression experienced by women after giving birth. Postpartum depression, which has incidence rate of 10-15%, typically sets in within three months of labor, and lasts as long as three months. Seasonal affective disorder (SAD), also known as "winter depression" or "winter blues", is a specifier. Some people have a seasonal pattern, with depressive episodes coming on in the autumn or winter, and resolving in spring. The diagnosis is made if at least two episodes have occurred in colder months with none at other times over a two-year period or longer.

Dysthymia, which is a chronic, different mood disturbance where a person reports a low mood almost daily over a span of at least two years. The symptoms are not as severe as those for major depression, although people with dysthymia are vulnerable to secondary episodes of major depression (sometimes referred to as double depression). Depressive Disorder Not Otherwise Specified (DD-NOS) is designated by the code 311 for depressive disorders that are impairing but do not fit any of the officially specified diagnoses. According to the DSM-IV, DD-NOS encompasses "any depressive disorder that does not meet the criteria for a specific disorder." It includes the research diagnoses of recurrent brief depression, and minor depressive disorder listed below. Recurrent brief depression (RBD), distinguished from major depressive disorder primarily by differences in duration. People with RBD have depressive episodes about once per month, with individual episodes lasting less than two weeks and typically less than 2-3 days. Diagnosis of RBD requires that the episodes occur over the span of at least one year and, in female patients, independently of the menstrual cycle.[ People with clinical depression can develop RBD, and vice versa, and both illnesses have similar risks. Minor depressive disorder, or simply minor depression, which refers to a depression that does not meet full criteria for major depression but in which at least two symptoms are present for two weeks.

Bipolar disorder (BD), a mood disorder formerly known as "manic depression" and described by alternating periods of mania and depression (and in some cases rapid cycling, mixed states, and psychotic symptoms). Subtypes include: Bipolar I is distinguished by the presence or history of one or more manic episodes or mixed episodes with or without major depressive episodes. A depressive episode is not required for the diagnosis of Bipolar I disorder, but depressive episodes are often part of the course of the illness. Cyclothymia is a different form of bipolar disorder, consisting of recurrent hypomanic and dysthymic episodes, but no full manic episodes or full major depressive episodes. Bipolar Disorder Not Otherwise Specified (BD-NOS), sometimes called "sub-threshold" bipolar, indicates that the patient suffers from some symptoms in the bipolar spectrum (e.g. manic and depressive symptoms) but does not fully qualify for any of the three formal bipolar DSM-IV diagnoses mentioned above. It is estimated that roughly one percent of the adult population suffers from bipolar I, roughly one percent of the adult population suffers from bipolar II or cyclothymia, and somewhere between two and five percent suffer from "sub-threshold" forms of bipolar disorder.

Substance-induced mood disorders refers to a mood disorder that can be classified as substance-induced if its etiology can be traced to the direct physiologic effects of a psychoactive drug or other chemical substance, or if the development of the mood disorder occurred contemporaneously with substance intoxication or withdrawal. Alternately, an individual may have a mood disorder coexisting with a substance abuse disorder. Substance-induced mood disorders can have features of a manic, hypomanic, mixed, or depressive episode. Most substances can induce a variety of mood disorders. For example, stimulants such as amphetamine (Adderall, Dexedrine; "Speed"), methamphetamine (Desoxyn; "Meth", "Crank", "Crystal", etc), and cocaine ("Coke", "Crack", etc) can cause manic, hypomanic, mixed, and depressive episodes. Alcohol-induced mood disorders includes major depressive disorder occurring in heavy drinkers and those with alcoholism. Controversy has previously surrounded whether those who abused alcohol and developed depression were self-medicating their pre-existing depression, but recent research has concluded that, while this may be true in some cases, alcohol misuse directly causes the development of depression in a significant number of heavy drinkers. High rates of suicide also occur in those who have alcohol-related problems. It is usually possible to differentiate between alcohol-related depression and depression which is not related to alcohol intake by taking a careful history of the patient. Depression and other mental health problems associated with alcohol misuse may be due to distortion of brain chemistry, as they tend to improve on their own after a period of abstinence.

Benzodiazepine-induced mood disorders may be associated with long term use of benzodiazepines which have a similar effect on the brain as alcohol and are also associated with depression. Major depressive disorder can also develop as a result of chronic use of benzodiazepines or as part of a protracted withdrawal syndrome. Benzodiazepines are a class of medication which are commonly used to treat insomnia, anxiety and muscular spasms. As with alcohol, the effects of benzodiazepine on neurochemistry, such as decreased levels of serotonin and norepinephrine, are believed to be responsible for the increased depression. Major depressive disorder may also occur as part of the benzodiazepine withdrawal syndrome. In a long-term follow-up study of patients dependent on benzodiazepines, 10 people (20%) had taken drug overdoses while on chronic benzodiazepine medication despite only two people ever having had any pre-existing depressive disorder. A year after a gradual withdrawal program, no patients had taken any further overdoses. Depression resulting from withdrawal from benzodiazepines usually subsides after a few months but in some cases may persist for 6-12 months.

Anxiety disorder is a blanket term covering several different forms of abnormal and pathological fear and anxiety which only came under the aegis of psychiatry at the very end of the 19th century. Current psychiatric diagnostic criteria recognize a wide variety of anxiety disorders. Recent surveys have found that as many as 18% of Americans may be affected by one or more of them.

Anxiety disorders are often debilitating chronic conditions, which can be present from an early age or begin suddenly after a triggering event. They are prone to flare up at times of high stress and are frequently accompanied by physiological symptoms such as headache, sweating, muscle spasms, palpitations, and hypertension, which in some cases lead to fatigue or even exhaustion.

Although in casual discourse the words anxiety and fear are often used interchangeably, in clinical usage, they have distinct meanings; anxiety is defined as an unpleasant emotional state for which the cause is either not readily identified or perceived to be uncontrollable or unavoidable, whereas fear is an emotional and physiological response to a recognized external threat. The term anxiety disorder, however, includes fears (phobias) as well as anxieties. Anxiety disorders are often comorbid with other mental disorders, particularly clinical depression, which may occur in as many as 60% of people with anxiety disorders. The fact that there is considerable overlap between symptoms of anxiety and depression, and that the same environmental triggers can provoke symptoms in either condition, may help to explain this high rate of comorbidity.

Types of anxiety disorders include generalized anxiety disorder, panic disorder, phobias, agoraphobia, social anxiety disorder, obsessive-compulsive disorder, post-traumatic stress disorder, and separation anxiety disorder.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

The Compositions

Compounds, and pharmaceutical compositions thereof, having potency, specificity and selectivity in the diagnosis, prophylaxis, prevention, treatment and prognosis of conditions such depression, including for instance, major depression and dysthymia, and other related conditions described herein.

Accordingly, the invention provides pharmaceutical compositions comprising:
a) a full agonist of α1- and α2-adrenoceptor; and
b) a carrier or adjuvant.

Specifically, the invention provides pharmaceutical compositions comprising:

c) a prodrug of a full agonist of α1- and α2-adrenoceptor; and
d) a carrier or adjuvant.

More specifically, the invention provides pharmaceutical compositions comprising:
a) a full agonist or a prodrug of a full agonist of α1- and α2-adrenoceptor;
b) an additional α-adrenergic modulator; and
c) a carrier or adjuvant.

In one embodiment, with respect to the pharmaceutical composition, the modulator of α1- and α2-adrenoceptor is a full agonist of both α1- and α2-adrenoceptor.

In one particular embodiment, with respect to the pharmaceutical composition, the modulator of α1- and α2-adrenoceptor is an epinephrine derivative. Another particular embodiment, modulator of α1- and α2-adrenoceptor is a norepinephrine derivative.

In a more particular embodiment, with respect to the pharmaceutical composition, the modulator of α1- and α2-adrenoceptor is 6-fluoronorepinephrine.

In another embodiment, the invention provides pharmaceutical compositions comprising:
a) a prodrug of a full agonist of α1- and α2-adrenoceptor;
b) an additional α-adrenergic modulator; and
c) a carrier or adjuvant.

In a further embodiment, the invention provides pharmaceutical compositions comprising:
a) a prodrug of a 6-fluoronorepinephrine;
b) an additional α-adrenergic modulator; and
c) a carrier or adjuvant.

In another aspect the invention provides a pharmaceutical composition comprising:
a) a prodrug according to formula I:

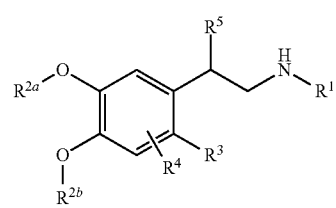

wherein
R$^1$ is selected from H, and substituted or unsubstituted C$_1$-C$_6$ alkyl;
each R$^{2a}$, and R$^{2b}$ is independently selected from H, and an enzymatically cleavable group; provided that at least one of R$^{2a}$, and R$^{2b}$ is other than H;
each R$^3$ and R$^4$ is independently selected from H, halo, substituted or unsubstituted C$_1$-C$_6$ alkyl, substituted or unsubstituted halo C$_1$-C$_6$ alkyl, hydroxy, substituted or unsubstituted amino, and substituted or unsubstituted C$_1$-C$_6$ alkoxy;
and R$^5$ is H, or OH;
or a pharmaceutically acceptable salt, or solvate thereof; and stereoisomers, isotopic variants and tautomers thereof;
b) an additional α-adrenergic modulator; and
c) a carrier or adjuvant.

In one embodiment, with respect to the pharmaceutical composition of the invention, R$^1$ is H, Me, Et, n-Pr, i-Pr, n-Bu, t-Bu, or CF$_3$. In another embodiment, R$^1$ is Me, Et, n-Pr, i-Pr, n-Bu, or t-Bu. In another embodiment, R$^1$ is Me. In a particular embodiment, R$^1$ is H.

In one embodiment, with respect to the pharmaceutical composition of the invention, R⁴ is H.

In one embodiment, with respect to the pharmaceutical composition of the invention, R³ is H, F, Br, Cl, or CF₃. In another embodiment, R³ is H, F, Cl, or CF₃. In another embodiment, R³ is Me or NMe₂. In a particular embodiment, R³ is F.

In one embodiment, with respect to the pharmaceutical composition of the invention, R⁵ is H.

In one embodiment, with respect to the pharmaceutical composition of the invention, R⁵ is OH.

In one embodiment, with respect to the pharmaceutical composition of the invention, the composition comprises:

a) a prodrug according to formula IIa or IIb or IIc:

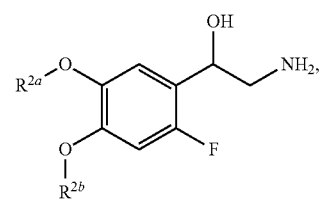

IIa

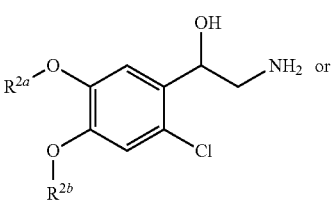

IIb

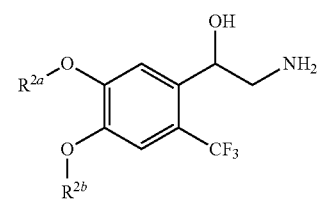

IIc wherein each $R^{2a}$, and $R^{2b}$ is independently selected from H, and an enzymatically cleavable group;

or a pharmaceutically acceptable salt, or solvate thereof; and stereoisomers, isotopic variants and tautomers thereof;

provided that at least one of $R^{2a}$, and $R^{2b}$ is other than H;

b) an additional α-adrenergic modulator; and c) a carrier or adjuvant.

In yet another aspect, the invention provides a compound according to formula IIa or IIb or IIc:

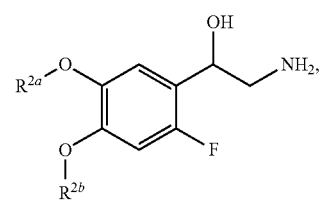

IIa

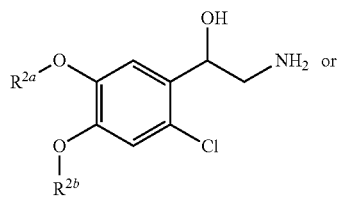

IIb

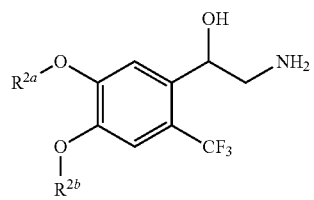

IIc wherein each $R^{2a}$, and $R^{2b}$ is independently selected from H, and an enzymatically cleavable group; provided that at least one of $R^{2a}$, and $R^{2b}$ is other than H;

or a pharmaceutically acceptable salt, or solvate thereof; and stereoisomers, isotopic variants and tautomers thereof.

In yet another aspect, the invention provides a compound according to formula IId:

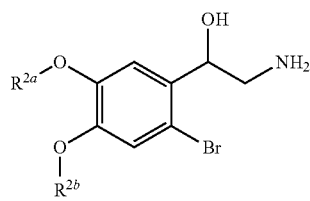

IId wherein each $R^{2a}$, and $R^{2b}$ is independently selected from H, and an enzymatically cleavable group; provided that at least one of $R^{2a}$, and $R^{2b}$ is other than H;

or a pharmaceutically acceptable salt, or solvate thereof; and stereoisomers, isotopic variants and tautomers thereof.

In one embodiment, with respect to the pharmaceutical composition or the compound of the invention, $R^{2a}$ is H; and $R^{2b}$ is an enzymatically cleavable group.

In another embodiment, with respect to the pharmaceutical composition or the compound of the invention, $R^{2b}$ is H; and $R^{2a}$ is an enzymatically cleavable group.

In one embodiment, with respect to the pharmaceutical composition or the compound of the invention, each $R^{2a}$ and $R^{2b}$ is independently an enzymatically cleavable group.

In one embodiment, with respect to the pharmaceutical composition or the compound of the invention, each $R^{2a}$ and $R^{2b}$ is independently H, or an enzymatically cleavable group; and the enzymatically cleavable group is selected from substituted or unsubstituted acyl, an amino acid residue, a dipeptide residue, a tripeptide residue, and a group

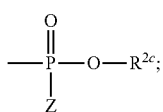

$R^{2c}$ is alkyl, aryl, or heteroaryl; Z is an amino acid residue, a dipeptide residue, or a tripeptide residue.

In one embodiment, with respect to the pharmaceutical composition or the compound of the invention, each $R^{2a}$ and $R^{2b}$ is independently H or an enzymatically cleavable group; and the enzymatically cleavable group is an amino acid residue.

In one embodiment, with respect to the pharmaceutical composition or the compound of the invention, each $R^{2a}$ and $R^{2b}$ is independently H, or an enzymatically cleavable group; and the enzymatically cleavable group is selected from -D-isoleucyl; -L-isoleucyl; -D-valy; -L-valyl; -glycyl; -D-phenylalanyl; -L-phenylalanyl; -D-leucyl; -L-leucyl; -L-aspartyl; -D-alpha-aspartyl; -L-alpha-aspartyl; -D-beta-aspartyl; -L-beta-aspartyl; and -L-prolyl.

In another embodiment, with respect to the pharmaceutical composition or the compound of the invention, each $R^{2a}$ and $R^{2b}$ is independently H, or an enzymatically cleavable group; and the enzymatically cleavable group is a dipeptide residue.

In a yet another embodiment, with respect to the pharmaceutical composition or the compound of the invention, each $R^{2a}$ and $R^{2b}$ is independently H, or an enzymatically cleavable group; and the enzymatically cleavable group is a tripeptide residue.

In one embodiment, with respect to the pharmaceutical composition or the compound of the invention, each $R^{2a}$ and $R^{2b}$ is independently H, or an enzymatically cleavable group; and the enzymatically cleavable group is

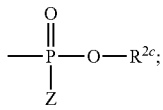

and wherein Z and $R^2$ are as in claim 2.

In one embodiment, with respect to the pharmaceutical composition or the compound of the invention, each $R^{2a}$ and $R^{2b}$ is independently H, an enzymatically cleavable group, the enzymatically cleavable group is as described above; and Z is an amino acid residue.

In one embodiment, with respect to the pharmaceutical composition or the compound of the invention, each $R^{2a}$ and $R^{2b}$ is independently H, an enzymatically cleavable group, the enzymatically cleavable group is as described above; and $R^{2c}$ is benzyl.

In one embodiment, with respect to the pharmaceutical composition or the compound of the invention, each $R^{2a}$ and $R^{2b}$ is independently H, an enzymatically cleavable group; and the enzymatically cleavable group is the enzymatically cleavable group is selected from -D-isoleucyl phosphoramidate; -L-isoleucyl phosphoramidate; -D-valyl phosphoramidate; -L-valyl phosphoramidate; -glycyl phosphoramidate; -D-phenylalanyl phosphoramidate; -L-phenylalanyl phosphoramidate; 5'-0-L-leucyl phosphoramidate; 5'-0-L-aspartyl phosphoramidate; -D-alpha-aspartyl phosphoramidate; -L-alpha-aspartyl phosphoramidate; D-beta-aspartyl phosphoramidate; -L-beta-aspartyl phosphoramidate; and -L-prolyl phosphoramidate.

In one particular embodiment, with respect to the pharmaceutical composition or the compound of the invention, each $R^{2a}$ and $R^{2b}$ is independently H, an enzymatically cleavable group; and the enzymatically cleavable group is substituted or unsubstituted $C_1$-$C_6$ acyl.

In another particular embodiment, with respect to the pharmaceutical composition or the compound of the invention, each $R^{2a}$ and $R^{2b}$ is independently H, an enzymatically cleavable group; and the enzymatically cleavable group is COMe, COEt, CO-n-Pr, CO-i-Pr, or CO-t-Bu.

In another particular embodiment, with respect to the pharmaceutical composition or the compound of the invention, each $R^{2a}$ and $R^{2b}$ is independently H, an enzymatically cleavable group; and the enzymatically cleavable group is benzoyl or CO-Aryl.

In a more particular embodiment, with respect to the pharmaceutical composition or the compound of the invention, each $R^{2a}$ and $R^{2b}$ is independently H, an enzymatically cleavable group; and the enzymatically cleavable group is CO-t-Bu.

In one particular embodiment, with respect to the pharmaceutical composition or the compound of the invention, each $R^{2a}$ and $R^{2b}$ is independently H, an enzymatically cleavable group; and the enzymatically cleavable group is substituted or unsubstituted alkoxycarbonyl. In one embodiment the enzymatically cleavable group is CO—O-alkyl. In another embodiment the enzymatically cleavable group is CO—O-Me, or CO—O-t-Bu.

In a further aspect, the invention provides a pharmaceutical composition wherein the composition comprises:

a) a prodrug according to formula IIIa, IIIb, or IIIc:

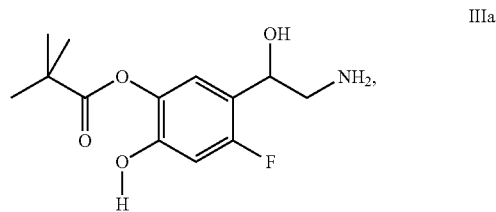

IIIa

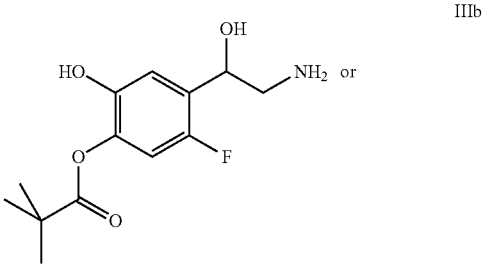

IIIb

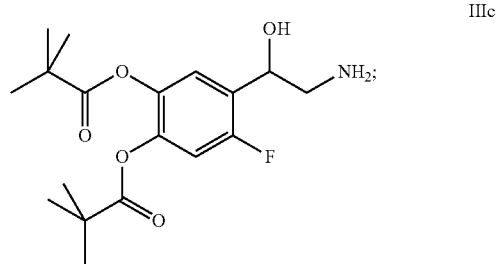 [SMILES: CC(C)(C)C(=O)Oc1cc(F)c(C(O)CN)cc1OC(=O)C(C)(C)C]

IIIc or a pharmaceutically acceptable salt, or solvate thereof; and stereoisomers, isotopic variants and tautomers thereof;

b) an additional α-adrenergic modulator; and c) a carrier or adjuvant.

In yet another aspect, the invention provides a compound according to formula IIIa, IIIb, or IIIc:

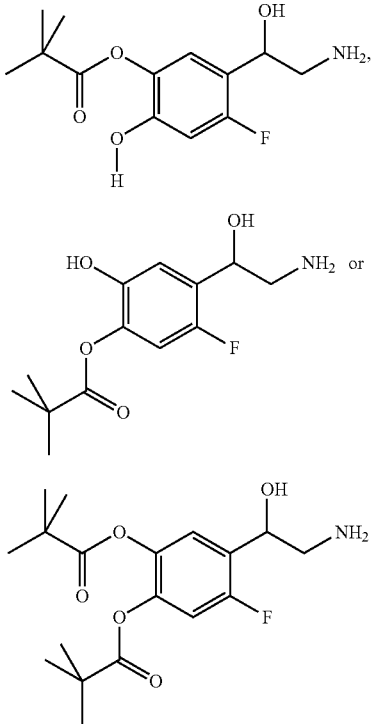

or a pharmaceutically acceptable salt, or solvate thereof; and stereoisomers, isotopic variants and tautomers thereof.

In one embodiment, with respect to the pharmaceutical composition of the invention, the adrenoceptor agonist or the inhibitor of the adrenergic receptor is a prodrug, and the prodrug is according to formula IIIc.

In one embodiment, with respect to the pharmaceutical composition of the invention, the adrenoceptor agonist or the inhibitor of the adrenergic receptor is dp6FNE (compound of formula IIIc).

In one embodiment, with respect to the pharmaceutical composition of the invention, the adrenoceptor agonist or the inhibitor of the adrenergic receptor is dpEPI (compound of formula IV).

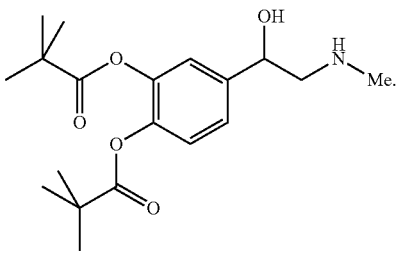

In a particular embodiment, with respect to the pharmaceutical composition, the modulator of α1- and α2-adrenoceptor is a compound according to formula I, IIa-IId, IIIa-IIIc, or IV.

In a particular embodiment, with respect to the pharmaceutical composition, the modulator of α1- and α2-adrenoceptor is 6FNE.

In one embodiment, with respect to the pharmaceutical composition of the invention, the prodrug does pass the blood-brain barrier. In one particular embodiment, with respect to the pharmaceutical composition of the invention, the prodrug does pass the blood-brain barrier and is enzymatically cleaved within the brain tho yield the active parent catecholamine. In one embodiment, with respect to the pharmaceutical composition of the invention, the additional α-adrenergic modulator is an α-adrenergic antagonist. In one embodiment, with respect to the pharmaceutical composition of the invention, the additional α-adrenergic modulator is selected from doxazosin, terazosin, labetalol, indoramin, phenoxybenzamine, tolazoline, dihydroergotamine and cardevilol. In one particular embodiment, with respect to the pharmaceutical composition of the invention, the additional α-adrenergic modulator is a modulator incapable of crossing the blood-brain barrier. In another particular embodiment, with respect to the pharmaceutical composition of the invention, the additional α-adrenergic modulator is a modulator which does not enter the brain. In a more particular embodiment, with respect to the pharmaceutical composition of the invention, the additional α-adrenergic modulator is prazosin. In a particular embodiment, with respect to the pharmaceutical composition of the invention, the additional α-adrenergic modulator is phentolamine; In a further particular embodiment, with respect to the pharmaceutical composition of the invention, the additional α-adrenergic modulator is cardevilol.

In one particular embodiment, with respect to the pharmaceutical composition of the invention, when the modulator of α1- and α2-adrenoceptor is a compound according to formula IV; the pharmaceutical composition further comprises an inhibitor of β-adrenoceptors. In one embodiment, the inhibitor of β-adrenoceptors is propranolol.

In one embodiment, with respect to the pharmaceutical composition of the invention, the additional α-adrenergic modulator is present at dosage levels equivalent to 0.1 to 100% of the dosage normally administered in a monotherapy regimen. In one embodiment, with respect to the pharmaceutical composition of the invention, the additional α-adrenergic modulator is present at dosage levels equivalent to about 0.5 to about 2 mg of the dose. In one embodiment, with respect to the pharmaceutical composition of the invention, the additional α-adrenergic modulator is present at dosage levels equivalent to about 0.5 to about 2 mg of the dose and is administered twice daily.

In one embodiment, with respect to the pharmaceutical composition of the invention, the additional α-adrenergic modulator is a compound capable of blocking activation of cardiovascular □1-adrenoceptor. In another embodiment, the additional α-adrenergic modulator is a compound capable of blocking activation of cardiovascular □1-adrenoceptor. In another embodiment, the additional α-adrenergic modulator is an antagonist of □1-adrenergic receptor. In another embodiment, the additional α-adrenergic modulator is an antagonist of □-adrenergic receptor. In another embodiment, the additional α-adrenergic modulator is an antagonist of both □1- and □-adrenergic receptors.

In one embodiment, with respect to the pharmaceutical composition of the invention, the carrier is a parenteral carrier. In one embodiment, with respect to the pharmaceutical composition of the invention, the carrier is an oral carrier. In one embodiment, with respect to the pharmaceutical composition of the invention, the carrier is a topical carrier. In a particular aspect, the invention provides a composition of any one of the prodrugs described herein. In a particular aspect, the invention provides a composition of the prodrug or compound according to formulae I-IV.

In another aspect, the invention provides a method for treating α-adrenergic mediated disease or condition in a mammal comprising the step of administering to the mammal a composition or compound of the invention. In one embodiment, the disease or condition is depression. In a particular aspect, the invention provides a use of the composition of the invention in anti-depressant, anti-stress, or anxiolytic therapies. In a particular aspect, the invention provides a use of the composition of the invention in the rapid treatment of depression and in reducing the likelihood, deterring or preventing suicide. In a particular aspect, the invention provides a use of the composition comprising dp6FNE in the rapid treatment of depression and in reducing the likelihood, deterring or preventing suicide. In a further particular aspect, the invention provides a use of the composition comprising dp6FNE in preventing imminent suicide.

In another aspect, the invention provides a method for treating a disease selected from the group consisting of an anxiety disorder or a mood disorder in a mammal comprising the step of administering to said mammal a compounds or a pharmaceutical composition according to the invention. The method may be used to reduce the likelihood, deter or prevent suicide.

In one embodiment, with respect to the method, the disease is an anxiety disorder.

In one embodiment, with respect to the method, the disease is a mood disorder.

In one embodiment, with respect to the method, the mood disorder is selected from the group consisting of dysthymia and major depression.

In one embodiment, with respect to the method, the administering results in a reduction in at least one clinical symptom of depression within one day.

In one embodiment, with respect to the method, the administering results in a reduction in at least one clinical symptom of depression within one week.

In one embodiment, with respect to the method, the administering results in a reduction in at least one clinical symptom of depression within one month.

In one embodiment, with respect to the method, the administering results in reducing a neural response in a stress response.

In one embodiment, with respect to the method, the administering results in increasing neural activity in one or more areas of the brain involved in motivated behavior.

Additional embodiments within the scope of the present invention are set forth in non-limiting fashion elsewhere herein and in the examples. It should be understood that these examples are for illustrative purposes only and are not to be construed as limiting this invention in any manner.

In certain aspects, the present invention provides prodrugs according to the formulae I-IV. Prodrugs are derivatives of the compounds of the invention, which have metabolically cleavable groups and become by solvolysis or under physiological conditions the compounds of the invention, which are pharmaceutically active, in vivo. Such examples include, but are not limited to, choline ester derivatives and the like, N-alkylmorpholinyl esters and the like.

Certain compounds of this invention have activity in both their acid and acid derivative forms, but the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy)alkyl esters or ((alkoxycarbonyl)oxy) alkylesters. Preferred are the $C_1$ to $C_8$ or $C_1$-$C_6$alkyl, $C_2$-$C_8$ alkenyl, aryl, substituted aryl, and arylalkyl esters of the compounds of the invention.

Pharmaceutical Compositions

When employed as pharmaceuticals, the compounds of this invention are typically administered in the form of a pharmaceutical composition. Such compositions can be prepared in a manner well known in the pharmaceutical art and comprise at least one active compound. In certain embodiments, the pharmaceutical composition may comprise a compound of the invention in combination with one or more compounds or compositions of like therapeutic utility and effect.

Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of this invention can be administered by a variety of routes including oral, rectal, transdermal, subcutaneous, intravenous, intramuscular, and intranasal. Depending on the intended route of delivery, the compounds of this invention are preferably formulated as either injectable, oral or intranasal compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the furansulfonic acid compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Intranasal compositions are typically mucoadhesive temperature-mediated in situ gel formulations using chitosan and hydroxyl propyl methylcellulose which enhance intranasal fixation and absorption producing transport into the central nervous system Khan, S., Patil, K., Bobade, N., Yeole, P., Gaikwad, R. 2010. Formulation of intranasal mucoadhesive temperature-mediated in situ gel containing ropinirole and evaluation of brain targeting efficiency in rats. *J Drug Target* 18, 223-234.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention:

The compounds of this invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of Remington's *The Science and Practice of Pharmacy*, 21$^{st}$ edition, 2005, Publisher: Lippincott Williams & Wilkins, which is incorporated herein by reference.

The compounds of this invention can also be administered in sustained release forms or from sustained release drug delivery systems. A description of representative sustained release materials can be found in *Remington's Pharmaceutical Sciences*.

The following formulation examples illustrate representative pharmaceutical compositions that may be prepared in accordance with this invention. The present invention, however, is not limited to the following pharmaceutical compositions.

Formulation 1—Tablets

The components of the pharmaceutical composition of the invention may be admixed as a dry powder with a dry gelatin binder in an approximate 1:2 weight ratio. A minor amount of magnesium stearate is added as a lubricant. The mixture is formed into 240-270 mg tablets (80-90 mg of active compound per tablet) in a tablet press.

Formulation 2—Capsules

The components of the pharmaceutical composition of the invention may be admixed as a dry powder with a starch diluent in an approximate 1:1 weight ratio. The mixture is filled into 250 mg capsules (125 mg of active compound per capsule).

Formulation 3—Liquid

The components of the pharmaceutical composition of the invention (125 mg) may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water may then be added to produce a total volume of 5 mL.

Formulation 4—Tablets

The components of the pharmaceutical composition of the invention may be admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Formulation 5—Injection

The components of the pharmaceutical composition of the invention may be dissolved or suspended in a buffered sterile saline injectable aqueous medium to a concentration of approximately 5 mg/mL.

Formulation 6—Topical

Stearyl alcohol (250 g) and a white petrolatum (250 g) may be melted at about 75° C. and then a mixture of a the components of the pharmaceutical composition of the invention (50 g, in proper ratio) methylparaben (0.25 g), propylparaben (0.15 g), sodium lauryl sulfate (10 g), and propylene glycol (120 g) dissolved in water (about 370 g) is added and the resulting mixture is stirred until it congeals.

Formulation 7—Intranasal

Temperature-mediated in situ gelling systems are prepared by dissolving The components of the pharmaceutical composition of the invention, chitosan HCl (1% w/v) and HPMC (varying grades and concentrations) in 0.5% sodium chloride maintained at temperature ~4° C. To the resulting solution 1 mL 0.282 M sodium β-glycerophosphate solution (ultimate concentration 8.8 wt %) is added drop by drop with continuous stirring while maintaining the temperature below 10° C. using the ice bath. Benzalkonium chloride (0.05% w/v) is added and pH adjusted to 7.0 using 1 M NaOH. A final volume of 10 mL is achieved with 0.5% sodium chloride. The formulations are stored below 10° C.

Methods of Treatment

The present compounds and the pharmaceutical compositions thereon are used as therapeutic agents for the treatment of conditions in mammals. Accordingly, the compounds and pharmaceutical compositions of this invention find use as therapeutics for preventing and/or treating illnesses, diseases, ailments, etc. such as, but not limited to, anxiety and mood disorders, such as, for instance depression and dysthymia.

In a method of treatment aspect, this invention provides a method of treating a mammal susceptible to or afflicted with a condition as recited above, which method comprises administering an effective amount of one or more of the pharmaceutical compositions described herein. In additional method of treatment aspects, this invention provides methods of treating a mammal susceptible to or afflicted with an anxiety or mood disorder, the method comprises administering an effective condition-treating or condition-preventing amount of one or more of the pharmaceutical compositions just described.

As a further aspect of the invention there is provided the present compounds for use as a pharmaceutical especially in the treatment or prevention of the aforementioned conditions and diseases. We also provide the use of the present compounds in the manufacture of a medicament for the treatment or prevention of one of the aforementioned conditions and diseases.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions, such as CNS conditions, the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 0.01 to about 20 mg/kg of the compound of the invention, with preferred doses each providing from about 0.1 to about 10 mg/kg and especially about 1 to about 5 mg/kg. Transdermal doses are generally selected to provide similar or lower blood levels than are achieved using injection doses.

The compounds and the pharmaceutical compositions of this invention can be administered as the sole active agent or they can be administered in combination with other agents, including other active amines and derivatives.

General Synthetic Procedures

The compounds of this invention can be prepared from readily available starting materials using the following general methods and procedures. See, e.g., Synthetic Scheme, below. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compounds of this invention, for example, may be prepared by the reaction of a chloro derivative with an appropriately substituted amine and the product isolated and purified by known standard procedures. Such procedures include (but are not limited to) recrystallization, column chromatography or HPLC. The following schemes are presented with details as to the preparation of representative fused heterocyclics that have been listed hereinabove. The compounds of the invention may be prepared from known or commercially available starting materials and reagents by one skilled in the art of organic synthesis.

The compounds of the present invention may be prepared by a variety of processes well known for the preparation of compounds of this type, for example reaction schemes. and general procedures as described below.

The syntheses of representative compounds of this invention are carried out in accordance with the methods set forth herein and using the appropriate reagents, starting materials, and purification methods known to those skilled in the art. All starting materials in the following general syntheses may be commercially available or obtained by conventional methods known to those skilled in the art.

In this specification, especially in "Representative Synthetic Methods", the following abbreviations can be used:

BEP 2-bromo-1-ethylpyridinium tetrafluoroborate

BOP benzotriazol-1-yloxy-tris(dimethylamino)phosphonium hexafluorophosphate

CDI 2-chloro-1,3-dimethylimidazolinium chloride

DCC dicyclohexylcarbodiimide

DCM dichloromethane

DME 1,2-dimethoxyethane, dimethoxyethane

DMF N,N-dimethylformamide

DMSO dimethyl sulfoxide

EDC 1-ethyl-3-(3'-dimethylaminopropyl)carbodiimide hydrogen chloride

EtOAc ethyl acetate

EtOH ethanol

HOBt 1-hydroxybenzotriazole

MeOH methanol

NMP N-methyl-2-pyrroliidone

THF tetrahydrofuran

TFA trifluoroacetic acid uM □M uL □L

Synthesis of Representative Compounds of the Invention

Compounds or starting materials for the compounds of the invention may be prepared following the various methods described in U.S. Pat. No. 3,904,671, U.S. Pat. No. 4,338,455, and WO8203327. These publications are incorporated by reference in their entirety, including all figures and tables, to the extent they are not inconsistent with the explicit teachings of this specification.

General Synthetic Methods for Preparing Compounds of the Invention

The compounds of the invention may be prepared following the representative synthetic schemes shown below:

Scheme 1
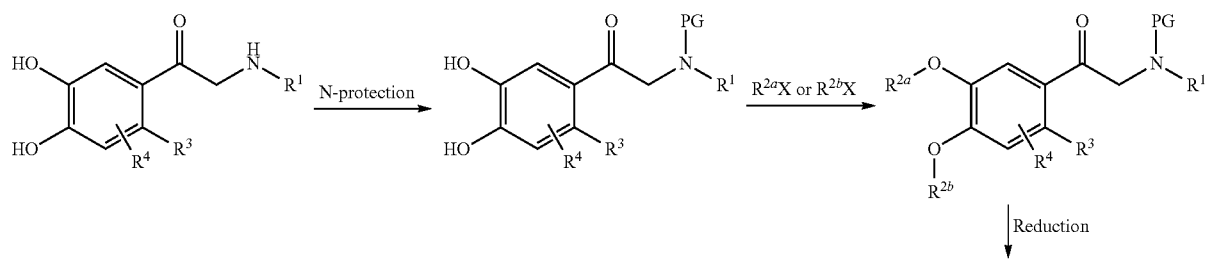
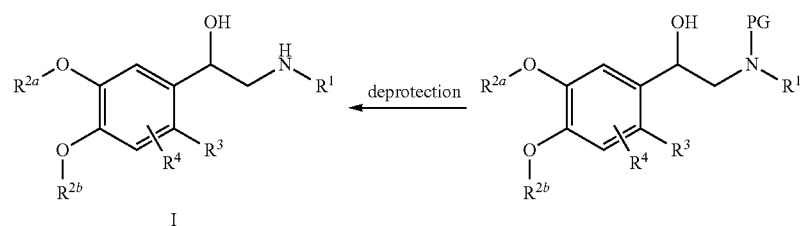
wherein $R^1$, $R^{2a}$, $R^{2b}$, $R^3$, and $R^4$ are as described herein; PG is a N-protecting group and X is a good leaving group. For example, X may be Cl, Br, I, or OTs.
Scheme 2
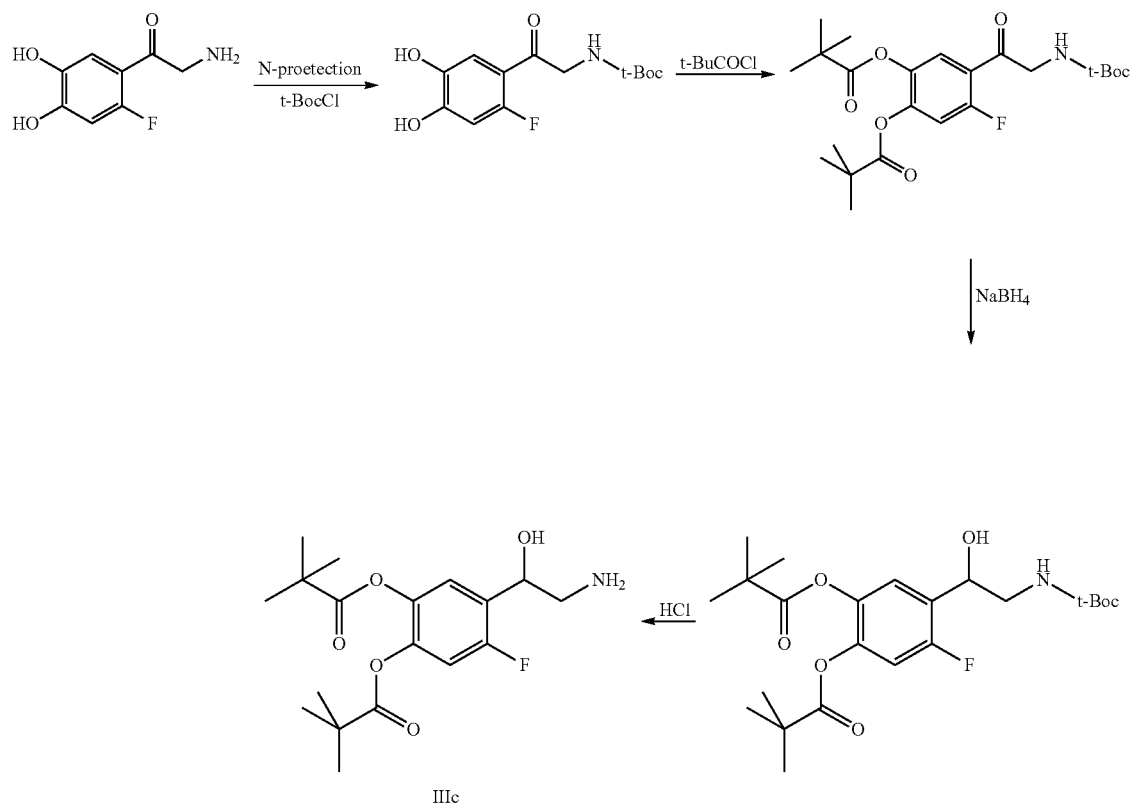

Scheme 3

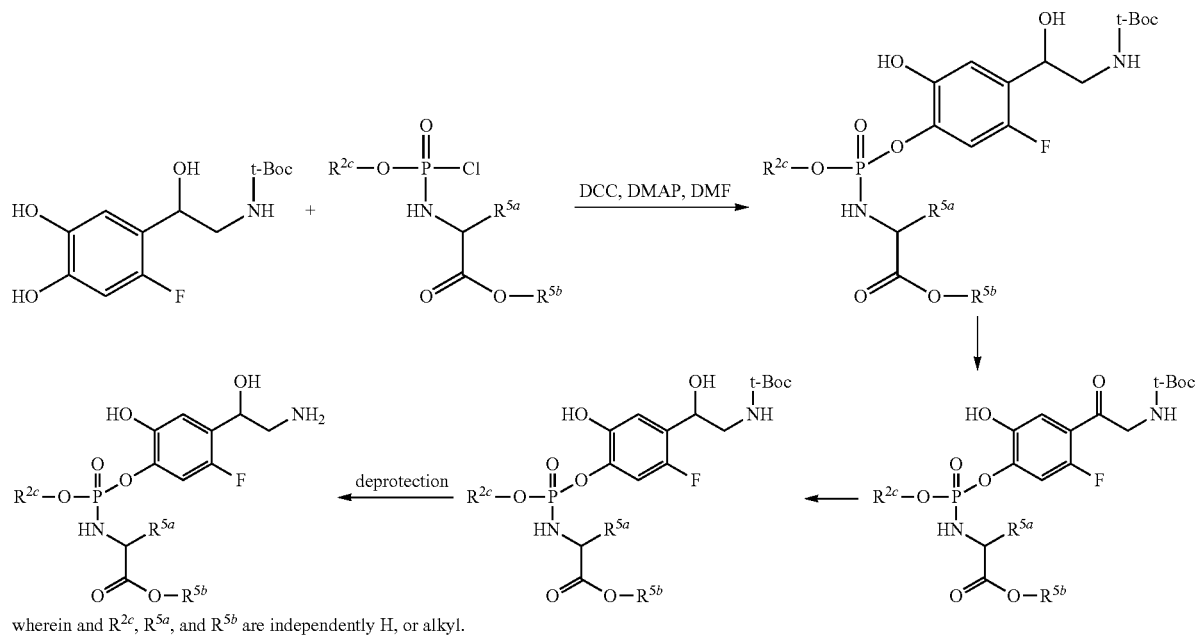

wherein and $R^{2c}$, $R^{5a}$, and $R^{5b}$ are independently H, or alkyl.

Therapeutic Effects

The synthetic catecholamine, 6-fluoronorepinephrine 6FNE, is a new antidepressant that may be capable of overcoming some of the difficulties associated with antidepressant agents, particularly therapeutic lag time. It unexpectedly produces several signs suggestive of rapid antidepressant and anti-stress activity after injection into the ventricular system of the brain. These include an immediate inhibition of brain circuits involved in stress and a disinhibition of circuits involved in motivated behavior leading to enhanced behavioral performance. The inhibited stress-sensitive nuclei include the locus coeruleus (LC), where the drug appears to principally act, and the paraventricular nucleus of the hypothalamus (PVH). The motivational regions that were activated, possibly as a result of the reduced noradrenergic input, include the nucleus accumbens shell, lateral septal nucleus and secondary motor cortex (amongst others). (Arnsten, et al., *Biol Psychiatry* 1999; 45: 26-31) The motivated behaviors that were disinhibited were exploration and escape from the home cage, wheel running, self stimulation of the lateral hypothalamus and water-reinforced operant behavior. The inhibition of the stress nuclei was subsequently found to be caused by primarily by stimulation of $\alpha_1$-adrenoceptors, one of the key receptors for the neurotransmitter, norepinephrine. This was also unexpected since prior research in the field had indicated that these receptors are excitatory rather than inhibitory (Gordon, et al., *J Neurosci* 2003; 23: 6223-6231; Hermann, et al., *J Physiol (Lond)* 2005; 562: 553-568) and it had been thought that norepinephrine stimulates rather than inhibits stress nuclei (Day, et al., *J Neurosci* 1999; 15: 10098-10106).

To test the effects of this compound on depression it was injected in the 4th cerebral ventricle or directly in the LC on 4 models of the disorder in the mouse: forced swim, tail suspension, repeated open-space swim, and lipopolysaccharide-induced anhedonia (reduction of preference for sweet solutions), plus an open field test as a control for motor activity. The LC was chosen on the basis of previous work showing that most antidepressant drugs act on this nucleus (West, et al., *Int J Neuropsychopharmacol* 2009; 12: 627-641). The above tests were chosen because they represent both acute and chronic forms of depression and involve both motoric (immobility) as well as hedonic (LPS-anhedonia) aspects of the disorder. The results were unambiguous; intraventricular or intra-LC 6FNE produced an immediate and marked antidepressant effect in all 4 tests and did so without stimulating motor activity in the open field (Stone, et al., *Int J Neuropsychopharmacol* 14, 319-331, 2011). Within minutes of administration, the drug markedly reduced immobility in the acute and repeated forced swim and tail suspension tests and in the same interval virtually abolished the inhibition of sucrose consumption following LPS treatment. As two of these tests (repeated open-space swim and LPS-anhedonia) had been shown to be resistant to acute antidepressant drug treatment (Stone, et al., *Pharmacol Biochem Behav* 2008; 91: 190-195; Sun, et al., *Neuroscience* 2004; 129: 129-139), these findings suggest that 6FNE has a rapid onset of action.

It was determined that 6FNE did not produce these effect by nonspecifically stimulating motor activity. Its effect on activity in the open field test was tested in which mice dosed with intraventricular 6FNE were measured for their locomotor activity in a large square enclosure (Stone, et al. *Submitted*, 2009). The drug had no effect on motor activity compared to non-injected controls although it did reverse the inhibition of this activity caused by the handling and injection procedure which mice find stressful. The latter effect indicates that the drug has significant anti-stress and anxiolytic actions that may underlie its antidepressant activity.

6FNE is therefore a full agonist at both the $\alpha_1$- and $\alpha_2$-adrenoceptors which are colocalized in a key stress nucleus in the brainstem—the locus coeruleus—and which both inhibit the neural activity of this nucleus and hence of stress reactions. Although $\alpha_2$-adrenoceptors have long been known to inhibit the LC, $\alpha_1$-adrenoceptors have an even more profound inhibitory effect on this brain region, and that 6FNE is the most potent inhibitor yet found for this nucleus (Stone, et al. *Brain Res* 2009; 1291: 21-31). This has not been described previously. Thus the selectivity of this compound for α-adrenoceptors, its full agonist property and the fact that it stimulates both $\alpha_1$- and $\alpha_2$-adrenoceptors that are colocalized to the locus coeruleus give 6FNE greater therapeutic potential in both depression and anxiety than any other known catecholamine or compound yet developed. These properties of 6FNE probably account for the fact that it works significantly faster than other therapeutic agents.

6FNE May be Better than a Pure $\alpha_2$-Agonist for Treatment of Depression.

Intracerebral injection of the $\alpha_2$-adrenergic agonist, clonidine, can produce rapid antidepressant effects in rats in the forced swim or the stress-potentiated forced swim test (Simson, et al., *Neuropharmacology* 1986; 25: 385-389; Weiss, et al., *Neuropharmacology* 1986; 25: 367-384). Thus there is existing preclinical evidence that $\alpha_2$-agonists can produce antidepressant effects although these compounds are not routinely used for the treatment of human depression. This brings up the question as to whether 6FNE has any advantage over simply using an $\alpha_2$-agonist alone to treat the disorder.

However, since 6FNE stimulates both the $\alpha_1$- and $\alpha_2$-adrenoceptors, it should have an advantage over using $\alpha_2$-agonists alone for depression. To further clarify this question we carried out an experiment comparing intracerebral 6FNE with intracerebral administration of a highly selective full $\alpha_2$-agonist, dexmedetomidine, in mice on two tests for antidepressant activity, the tail suspension test and the repeated open-space forced swim test. The first test involves an acute stress-induced model of depression (Steru, et al., *Psychopharmacology* 1985; 85: 367-370) whereas the second, a more prolonged, chronic depression that is more akin to chronic human depression (Stone, et al., *Pharmacol Biochem Behav* 2008; 91: 190-195). Both 6FNE and dexmedetomidine were equally effective on the tail suspension test (FIG. 1) but only 6FNE was effective on the repeated open-space forced swim (FIG. 2). 6FNE therefore has the advantage over $\alpha_2$-agonists in that it is active on more types of depression and on an animal depression that is more similar to human depression.

Another advantage of using 6FNE over $\alpha_2$-agonists is that it has no sedative effect. Sedation has not been observed, only behavioral activation, in a wide range of behavioral tests with intracerebral 6FNE (Stone, et al. *Brain Res* 2009; 1291: 21-31) or with peripheral administration of dipivalyl-6FNE (dp6FNE) whereas α2-agonists produce strong soporific actions and can be used to supplement anesthesia (Hall, et al., *Brit J Anaesth* 2001; 86: 5-11). Sedation interferes with behavioral performance and is therefore a detrimental side effect to the treatment of major depressive illness in humans.

6FNE May be Better at Treating Depression than Other $\alpha_1$-Agonists.

There are reports that other $\alpha_1$-agonists can also reverse depression in rodents. It has been shown previously that direct intracerebal infusion of the partial $\alpha_1$-agonist, phenylephrine (PE), produced antidepressant effects in the forced swim test in rats (Kitada, et al., *Neuropharmacology* 1983; 22: 1055-1060) and that systemic administration of PE also had an anti-immobility effect in this test but only at a near lethal dose (16 mg/kg, i.p.) (Pellow, et al., *J Neurosci Methods* 1985; 14: 149-167). It has also recently been reported that another partial α1-agonist, cirazoline, when given chronically to mice in the drinking water had significant antidepressant effects in the forced swim test (Doze, et al., *Brain Res* 2009; 1285: 148-157) and also stimulated neurogenesis in the cerebral ventricle walls (Gupta, et al., *Mol Pharmacol* 2009; 76: 314-326), a frequent concomitant of successful antidepressant action (Koo, et al. *Neurosci Lett* 2009; 456: 39-43).

6FNE has a more rapid and/or greater antidepressant effect than either of these agonists because 6FNE is the only known selective α-agonist that has full efficacy at all brain α-adrenoceptors and 6FNE works within minutes (Stone, et al. *Submitted*, 2009) whereas cirazoline was given to mice over several months prior to testing in one model (forced swim test) in the above experiment by Doze et al, 2009. The partial agonist PE, given intraventricularly, does not produce the same reversal of behavioral inhibition in the home cage after handling stress that 6FNE does (Stone, et al. *Brain Res* 2009; 1291: 21-31). The partial agonist, cirazoline, which enters the brain given i.p., was incapable of reversing behavioral inhibition in the home cage after handling stress (Stone, EA, Lin Y, Quartermain, D, Unpublished results).

6FNE May be Better than Other $\alpha_1$- and $\alpha_2$-Agonists or Other Anxiolytics for the Treatment of Stress and Anxiety.

The evidence that 6FNE has anti-stress/anti-anxiety properties consists of findings that intraventricular 6FNE markedly suppresses neural activity in two key stress brain nuclei, the locus coeruleus and paraventricular nucleus of the hypothalamus (Stone, et al. *Brain Res* 2009; 1291: 21-31) during handling stress, open-space forced swimming and, to a lesser degree, tail suspension stress. The compound also overcomes the behavioral inhibitory effect of handling stress on exploratory behavior in both the home cage and the open field and rescues the ability of handling-stressed mice to enter the more risky center regions of the field.

It is known however that $\alpha_2$-agonists, such as clonidine, can be used in the treatment of anxiety (Coplan, et al., *Psychopharmacology Bulletin* 1997; 33: 193-204). Furthermore, it has also been found that the intracerebral infusion of the partial $\alpha_1$-agonist, PE, is capable of moderately activating exploration in the home cage in handled rats (Stone, et al., *Synapse* 2004; 54: 164-172) while other investigators have found that infusion of this drug in the hypothalamus can exert an anxiolytic effect (Talalaenko, et al., *Neuroscience & Behavioral Physiology* 2003; 33: 255-261) and that injection of high peripheral doses can counter anxiety in the plus-maze (Zarrindast, et al., *Eur J Pharmacol* 2000; 407: 145-158). Also, peripheral administration of the antidepressant, mirtazepine, counters freezing behavior, a manifestation of anxiety in rats, and this effect appears to be mediated by $\alpha_1$-adrenoceptors. However, some have shown that intracerebral infusion of $\alpha_1$-agonists in the prefrontal cortex can produce behavioral disruption similar to anxiety (Arnsten, et al., *Biol Psychiatry* 1999; 45: 26-31).

The present data, however, indicate that intracerebal 6FNE or peripheral dp6FNE has greater anti-stress and anti-anxiety effects than clonidine or PE, given centrally or peripherally, and more rapid effects than mirtazepine for the following reasons:

Ivt. 6FNE immediately inhibits neural activity in the locus coeruleus and does so much more potently than a full $\alpha_2$-agonist, dexmedetomidine, that is more selective than clonidine (Stone, et al. *Brain Res* 2009; 1291: 21-31; Takano, et al., *J Pharmacol Exp Ther* 1991; 258: 438-446). Furthermore, 6FNE rescues exploratory behavior in the home cage of handling-stressed mice to a much greater extent than does either dexmedetomidine, PE or combined dexmedetomidine and PE (Stone et al., ibid).

Figure 3A:
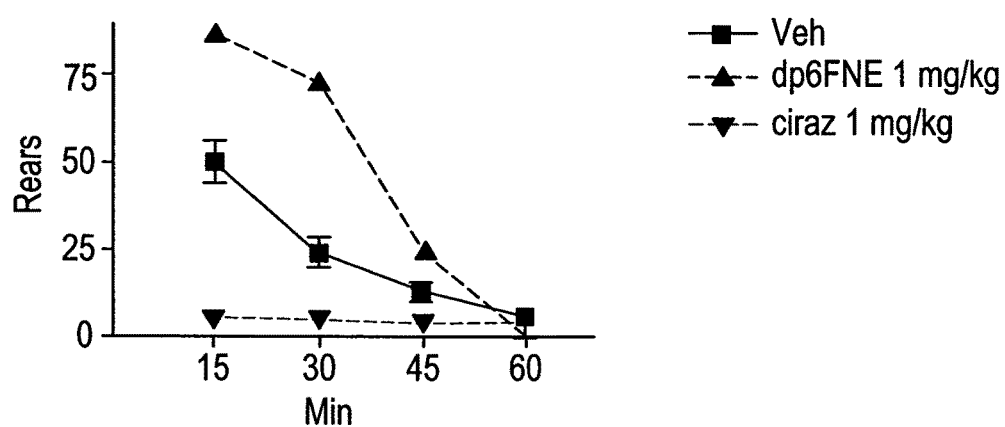
FIG. 3 depicts the effect of acute i.p. dp6FNE (1 mg/kg) or cirazoline (0.1 mg/kg), (both N=1), on home cage activity in terms of rearing and ambulation, Veh (N=12).
Figure 3B:
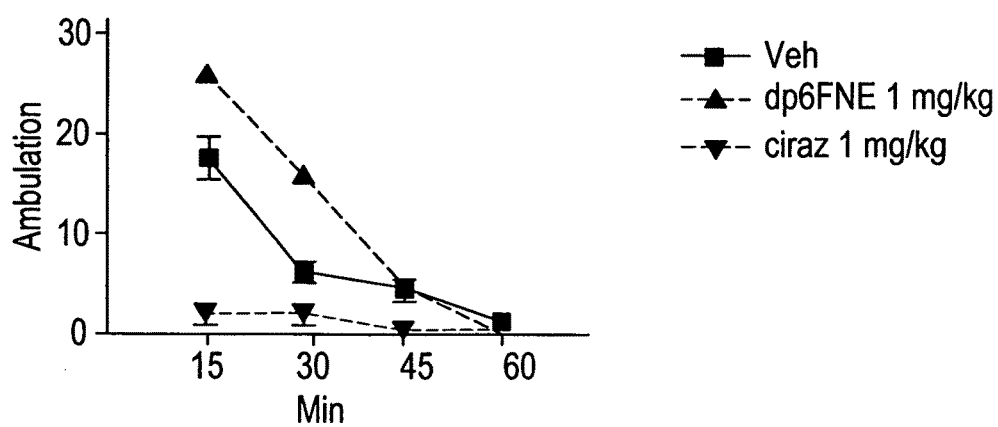

The same rescue of home cage exploration in handling-stressed mice given i.p. injections of dp6FNE in the presence of phentolamine was observed (FIG. 3). It is known that peripheral administration of $\alpha_1$-agonists without phentolamine impairs exploratory behavior in the open field (Yang, et al., *J Pharmacol exp Ther* 1990; 255: 1064-1070). Furthermore the partial $\alpha_1$-agonist, cirazoline, failed to affect anxiety as measured by behavioral inhibition in the light/dark box test or the elevated plus-maze test in mice even after months of chronic treatment (Doze, et al., *Brain Res* 2009; 1285: 148-157). In addition, as noted above, we have found that cirazoline is not effective in reducing behavioral inhibition in the home cage following handling and injection stress (FIG. 3).

An additional advantage of 6FNE over clonidine and other anxiolytics such as the benzodiazepines for the treatment of stress and/or anxiety, is that it is non-sedative and produces no obvious CNS impairment. Thus this agent produces equivalent anti-anxiety effects to these traditional anxiolytics without their sedative and impairing effects.

6FNE is not Another Catecholamine Stimulant

Figure 4A:
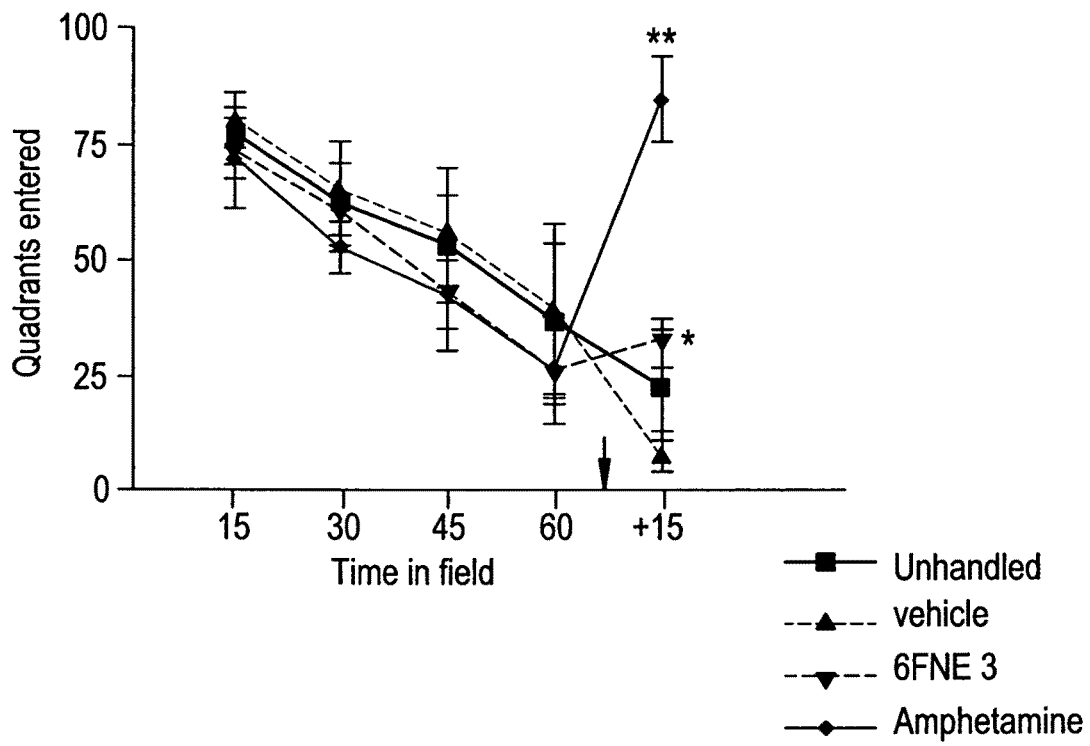
FIG. 4 A. demonstrates the effect of acute ivt. vehicle or 6FNE (3 nmoles), or i.p. amphetamine (5 mg/kg) on open field locomotion compared to unhandled controls. Treated mice received infusions at arrow following 1 h habituation to field and were recorded for following 15 min. *$p<0.05$**$p<0.0001$ versus 6FNE. B. demonstrates the effect of first 3 treatments on log time in center of field during latter 15 min period. *$p<0.05$ versus Vehicle, #$p<0.05$ versus 6FNE, N=6
Figure 4B:
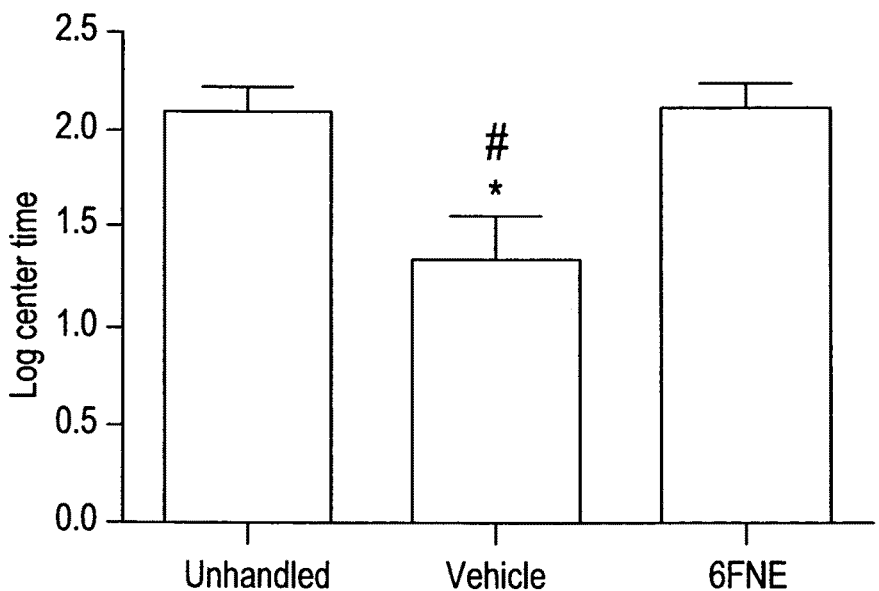
Figure 5A:
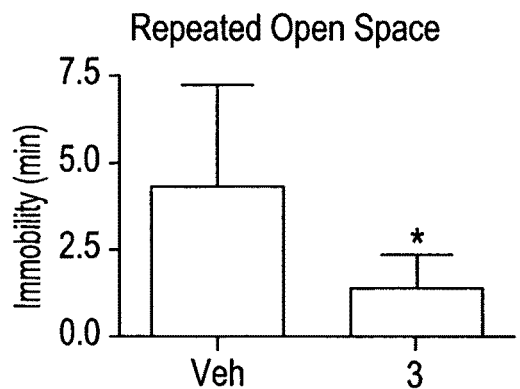
FIG. 5 Upper: demonstrates the effect of various doses of acute dp6FNE injected i.p. together with prazosin (0.2 mg/kg) on open space swim, tail suspension and chronic mild stress depression tests. Lower: demonstrates the results of an acute DMI (10 mg/kg, i.p.) on open space test. Note complete lack of effect of acute DMI but strong effect of acute dp6FNE/prazosin above in this test *$p<0.1$ vs Veh, #$<0.05$ vs Con. N=4-9/gp. * $p\leq0.05$ versus vehicle, planned contrast.
Figure 5B:
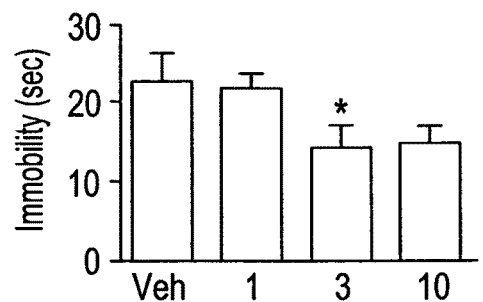
Figure 5C:
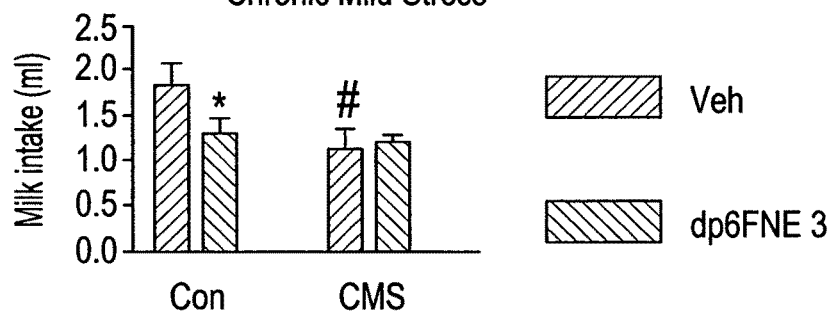
Figure 5D:
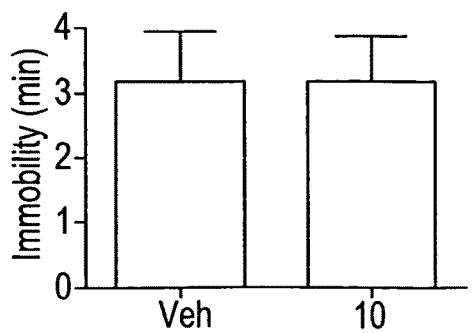

6FNE was tested for its effect on motor activity by measuring locomotor behavior in an open field after its ivt. injection in mice after they had habituated to the field. These mice were compared to animals that were either non handled or received either a vehicle ivt injection or an i.p. injection of the stimulant, amphetamine (5 mg/kg). The results are shown in FIG. 4. 6FNE produced no change in activity compared to the non-handled animals but did produce a small increase compared to the vehicle injected mice. Furthermore, the increase in activity after 6FNE was minor in comparison with the bona fide stimulant, amphetamine which produced a 10 fold increase. The small increase over the vehicle group therefore appears to be the result of a reduction of the stress caused by the handling and restraint for the ivt. injection which is in agreement with the reduced activation of brain stress circuits discussed above. This interpretation was supported by an examination of the time in the center or risky area of the field spent by the various groups. Vehicle injection significantly reduced the time in the center whereas 6FNE restored this behavior back to the level of the non-handled controls.

More information on 6FNE may be found in Stone et al *International Journal of Neuropsychopharmacology* (2011) 14: 319-331.

These findings therefore indicate that 6FNE represents a new class of rapidly-acting, potent antidepressant and anti-stress agents and may serve as a basis for the development of new compounds having these properties. However, there was still the problem that 6FNE is a polar compound which does not pass the blood brain barrier and therefore cannot be administered systemically. To overcome this problem, the antidepressant properties of peripheral administration of a lipid-soluble pro-drug derivative of it, dipivalyl-6FNE (dp6FNE), that does pass the blood brain barrier and is enzymatically cleaved within the brain to yield the active parent catecholamine, 6FNE (Introini-Collison, et al., *Brain Res* 1992; 572: 81-86; Wang; et al., *J Pharmacol Exp Ther* 1977; 203: 442-448) was tested.

The addition of lipophilic pivalyl groups to catecholamines permits these dipivalyl (dp) compounds to gain entry to the brain where they are enzymatically converted to back to the free catecholamines, which can then act upon membrane receptors (Wang et al., *J Pharmacol Exp Ther* 1977; 203: 442-448; Introini-Collison et al., *Brain Research*, 1992; 572: 81-86). We reasoned, therefore, that peripheral administration of dp6FNE should acutely inhibit LC neural activity and produce an immediate antidepressant effect in models that do not respond to acute treatments. A similar action should occur with the closely related pro-drug, dipivalyl-epinephrine (dpEPI), because its parent catecholamine, epinephrine (EPI), is also a full agonist at these two a-receptors (Johnson et al., *European Journal of Pharmacology* 1986; 129: 293-305). However, because EPI also stimulates $\beta$-adrenoceptors which may activate LC neurons (Nestler et al., *Biological Psychiatry* 1999; 46: 1131-1139), it would be necessary to first block $\beta$-receptors prior to its administration.

The new drug, dp6FNE was given along with prazosin (0.2 mg/kg, i.p.) or phentolamine (5 mg/kg, i.p.), a-antagonists that do not enter the brain (Anden, et al., *Psychopharmacology* 1974; 38: 91-103; Stone et al., *Eur. J. Pharmacol* 2001; 420:97-102), because peripheral $\alpha$-adrenoceptors, unlike their central counterparts, have pro-depressive and anxiogenic actions (Harsing, et al, *Pharmacology Biochemistry and Behavior*, 1989; 32: 927-932; Wong, et al., *Proc Natl Acad Sci USA* 2000; 97: 325-330).

The new compound, dp6FNE, has significant antidepressant action in the repeated open-space swim and tail suspension tests following i.p. administration at doses of 1, 3 and 10 mg/kg (FIG. 5). In addition, an initial comparison of the speed of action of i.p. dp6FNE with that of i.p. administration of the tricyclic antidepressant, desipramine (DMI) was performed, in the repeated open-space swim model, which does not respond to acute treatment. Evidence demonstrates that the new drug has a significantly faster onset of action than the latter tricyclic (FIG. 5). A test of the effect of the new drug in the chronic mild stress (CMS)-anhedonia model using the consumption of sweetened milk as the hedonic measure was performed, and evidence demonstrates that dp6FNE eliminates the CMS reduction of intake but also induces significant hypophagia (FIG. 5). The latter property may actually be beneficial as it would counter the weight gain frequently reported with antidepressant treatment (Richelson, *Mayo Clin Proc* 2001; 76: 511-527).

Dipivalyl-6-fluoronorepinephrine (dp6FNE) and prazosin or phentolamine may be combined for the rapid treatment of major depression and anxiety disorders. The structure of dp6FNE (IIIc), is shown below:

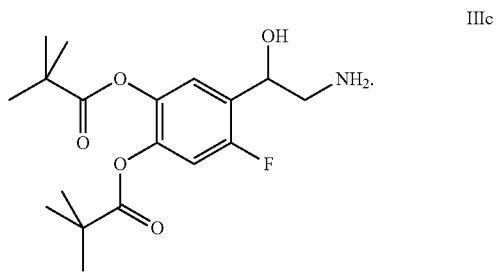

IIIc dp6FNE provides a more rapid and stronger antidepressant and anti-stress or anti-anxiety response, and one without any sedative effect, than that obtained with currently available antidepressant or anxiolytic therapies.

The catecholamine pro-drug, dipivalyl-6-fluoronorepinephrine (dp6FNE) may be used in combination with the peripherally-acting $\alpha$-adrenergic blocking agents, prazosin or phentolamine, for the rapid treatment of depression. It is commonly known that all currently available antidepressant drugs require several weeks administration to achieve their therapeutic effects (Sartorius, et al., *Int J Neuropsychopharmacol* 2007; 10 Suppl 1: S1-207). dp6FNE is a brain permeable pro-drug that is taken up centrally and enzymatically cleaved to form the active parent catecholamine, 6FNE, in all tissues including the brain. As discussed above, 6FNE, when administered in the brain via the 4th cerebral ventricle of the mouse, has immediate antidepressant activity in 4 independent screens (Stone et al, *Int J Neuropsychopharmacol* 14, 319-331, 2011)—the forced swim (Porsolt, et al., *Arch int*

Pharmacodyn Ther 1977; 229: 327-336), tail suspension (Stern, et al., Psychopharmacology 1985; 85: 367-370), repeated open-space forced swim (Sun, et al., J Neurosci Methods 2003; 126: 35-40) and lipopolysaccharide-induced anhedonia test (Frenois, et al., Psychoneuroendocrinology 2007; 32: 516-531. In addition, data shows significant antidepressant activity of its systemically (i.p.) administered pro-drug (dp6FNE) in the tail suspension test, repeated open-space forced swim test and chronic mild stress-anhedonia models (FIG. 5).

Dp6FNE may be used for the immediate control of stress and anxiety. Intraventricular 6FNE inhibits the neural activity of two recognized major stress nuclei in the brain (the locus coeruleus (Valentino, et al., Eur Pharmacol 2008; 583: 194-203) and paraventricular nucleus of the hypothalamus (Muigg, et al. Biol Psychiatry 2007; 61: 782-796)) during various stressful conditions and also reduces anxiety in the open field test (Defries, et al., Behav Biol 1974; 11: 481-495) as evidenced by a greater willingness to explore the center and risky areas of the field (Stone, et al. Journal of Neuropsychopharmacology 2010; In press). Intracerebral administration of 6FNE also reduces behavioral inhibition in mice in their home cages resulting from handling and injection procedures which are stressful for mice (Stone, et al. Brain Res 2009; 1291: 21-31). In addition the pro-drug, administered systemically, provides significant results in these and other tests of anxiety and stress such as the plus-maze (Pellow, et al., J Neurosci Methods 1985; 14: 149-167).

dp6FNE is unique in that the parent catecholamine, 6FNE, is the only known selective α-agonist that has full efficacy at all brain α-adrenoceptors (Johnson, et al. Eur J Pharmacol 1986; 129: 293-305; Johnson; et al., Mol Pharmacol 1987; 31: 239-246). All other $\alpha_1$-agonists, catecholamines or antidepressants that act on depression are either partial agonists (such as phenylephrine (Johnson, et al. Eur J Pharmacol 1986; 129: 293-305; Johnson; et al., Mol Pharmacol 1987; 31: 239-246; Law-Tho, et al., Eur J Neurosci 1993; 5: 1494-1500) and cirazoline (Thonberg; et al., Biochemical Journal 2002; 364: 73-79)), or are direct (norepinephrine and epinephrine) or indirect agonists (tricyclic antidepressants) at β-adrenergic receptors which can exacerbate depression and anxiety (Cole, et al., J Pharmacol exp Ther 1988; 247: 902-910; Kitada, et al., Jpn J Pharmacol 1983; 33: 867-873; Sulser, In: Typical and Atypical Antidepressants: Molecular Mechanisms, edited by Costa E and Racagni G. New York: Raven Press, 1982)), or are $\alpha_1$-receptor antagonists (tricyclic antidepressants (Richelson, Mayo Clin Proc 2001; 76: 511-527)).

dp6FNE may be used in combination with a peripheral α.receptor antagonist that does not enter the brain in order to prevent activation of peripheral α-adrenoceptors which may have opposing effects on depression and anxiety (Wong, et al., Proc Natl Acad Sci $_U$SA 2000; 97: 325-330; Yang, et al., J Pharmacol exp Ther 1990; 255: 1064-1070) and can produce unwanted cardiovascular effects. Phentolamine is unique in this respect in that it blocks both the $\alpha_1$- and $\alpha_2$-adrenoceptors but is not taken up by the brain (Anden, et al., Psychopharmacology 1974; 38: 91-103; Nordling, et al., Scandinavian Journal of Urology & Nephrology 1981; 15: 173-180) thus permitting dp6FNE to achieve a selective sti$_m$ulation of brain α-adrenoceptors. Prazosin, an $\alpha_1$-adrenoceptor antagonist, which is not taken up by the brain (Stone, et al., Eur.J.Pharmacol. (2001) 420, 97-102), may also be used to block the peripheral actions of dp6FNE.

The pro-drugs like dp6FNE have been administered shortly before one or more tests of antidepressant activity including reversal of immobility during tail suspension and forced swimming and attenuation of anhedonia produced by endotoxin administration. To preclude the activation of $\alpha_1$-adrenoceptors in the cardiovascular system, the drugs have been administered with a low dose of the $\alpha_1$-antagonist, prazosin, 0.2 mg/kg, which is below the dose necessary for either penetration of the brain or alterations in behavioral activation in Swiss-Webster mice (Stone et al., European Journal of Pharmacology 2001; 420: 97-102). Because dp6FNE like all other antidepressants has initial an anorexic effect and will acutely reduce the consumption of sweet solutions, in the test for anhedonia it was necessary to employ a non-nutritive hedonic behavior, FUST (sniffing of estrous female urine) (Malkesman et al., Biological Psychiatry 2010; 67: 146-154). The latter behavior like other hedonic activities has recently been shown to be impaired by chronic stressors that induce behavioral depression and to be rescued by chronic antidepressant treatment. To determine whether dp6FNE is more rapidly-acting than currently available drugs, its acute effects were compared with those of a panel of antidepressants on a variant of the forced swim test—the repeated forced swim (RFS) test—which has been shown to respond to repeated but not acute antidepressant administration; (Sun et al., Journal of Neuroscience Methods 2003; 126: 35-40; Sun et al., Behavioral Pharmacology 2008; 19: 334-338). To determine which a-receptor mediates the actions of dp6FNE, the effects of selective antagonists on its effects were also assessed. Finally, to assess any effects on locomotor activity, the drug was also tested on behavior in an open field.

dp6FNE Plus Phentolamine May be Better Than any Other Peripheral Catecholamine Treatment for Either Depression or Stress/Anxiety.

Although catecholamines have long been implicated in the treatment of depression, it has not been possible previously to produce an antidepressant response by administering a catecholamine systemically. Systemic catecholamines generally produce increases in anxiety (Yang, et al., J Pharmacol exp Ther 1990; 255: 1064-1070) and depression (Wong, et al., Proc Natl Acad Sci USA 2000; 97: 325-330; Metzer, et al., Headache 1987; 27: 571-572). dp6FNE plus phentolamine is therefore the first and only existing peripheral catecholamine preparation that works therapeutically in these conditions. Moreover, it is either significantly more rapid (i.e., versus other antidepressants) or more effective (i.e., versus other $\alpha_1$ and $\alpha_2$-agonists) than other treatments. Neither of these properties could be predicted from what was known prior to our researches with this compound.

EXAMPLE 1

Male Sprague Dawley rats (10-12 weeks old) were used. The animals were habituated to the laboratory for 1 week and, following stereotaxic surgery, were housed 1/cage with food and water ad libitum and a lights-on cycle of 0500-1700 h. In experiments with DSP4, the neurotoxin or saline vehicle was administered 7 days postoperatively and 10 days before the behavioral procedures described below. All experiments were conducted in accordance with the National Institutes of Health Guide for the Care and Use of Laboratory Animals (NIH Publications No. 85-23, revised 1985) and were approved by the New York University School of Medicine IUCAC.

Under ketamine/xylazine (100/10 mg/kg, i.p.) anesthesia rats were implanted stereotaxically in or near the dorsolateral border of the LC with 26-G cannula guide tubes bilaterally (flat skull coordinates: 9.7 mm from bregma, lateral 1.4 mm, ventral, 7.2 mm at an angle of 15.2° from the sagittal plane (Paxinos, et al. Sydney: Academic Press, 1986)). The internal cannula projected 1 mm from the tip of the guide tube. The animals were given 7-10 days recovery prior to experimentation.

Procedure

Novel Cage Test

The animal was brought from the animal facility to the laboratory (across the hall), given a bilateral microinjection of artificial cerebrospinal fluid (aCSF) containing either nothing (vehicle), terazosin (3 nmoles/side), or terazosin plus PE (10 nmoles/side), and immediately placed in a novel standard rat cage (22×25 z 45 cm) where it was videotaped from above for 15 min. The infusion (250 nl) was given over a 3-min interval via a 33-G internal cannula which projected 1 mm below the cannula tip and was attached to a syringe pump. We have shown in pilot experiments that bilateral infusions of aCSF of this volume and speed in the LC do not affect behavioral activity in the novel cage test. In order to conserve animals, the rats were given the above infusions and tests 2-3 times at weekly intervals using different drugs in counterbalanced order. For each test, a different novel cage was used and was moved to a different location in the laboratory.

Home Cage Test

The animal was brought into the laboratory in its home cage and habituated in this cage beneath the video camera for 3 h prior to being injected. Infusion of one of five doses of PE (0, 0.03, 0.1, 0.3, and 1 nmole/side) was given as above and the animal immediately returned to its home cage and videotaped for 30 min. Food and water remained on the cage during the test. The longer interval (30 min) was used in the home vs. novel cage test because a low baseline activity was desired, and it was necessary to allow time for the disturbance caused by handling the animal to subside. As in the novel cage test, the home cage tests were repeated for a total of 2-3 tests at weekly intervals with different doses of the agonist. All experiments were carried out between 1100 and 1400 h. Following the last behavioral test, the animals were anesthetized with Nembutal and infused bilaterally with 250 nl of 2% methylene blue. Frozen (unfixed) brain sections were stained with cresyl violet for histological localization of cannula placement.

Scoring of Exploratory Behavior

Videotapes were rated blind for gross movements (GMs), crosses of the cage midline (cage Xs), rearing responses, and time immobile (TI) by a trained observer. As in previous studies (Stone et al., 2003a), GMs were defined as any large investigative movement involving at least the head and forelimbs that was terminated by a momentary pause before the next movement ensued. This included walks to a wall, rears, turns in place, and stretch and attend responses. Grooming movements and consummatory responses (eating and drinking, which were rarely seen) were not included.

Autoradiography

The radioligand [$^{125}$I]HEAT was synthesized as described previously (Engel and Hoyer, 1981). Frozen LOCUS COERULEUS α1-ADRENOCEPTORS AND ACTIVITY 165 brain sections (15μ) were cut on a cryostat, mounted, and desiccated overnight at −15° C. Sections were fixed in 2% paraformaldehyde for 10 min, washed in 10 mM Tris buffer, pH 7.4, containing 1 mM EDTA and 154 mM NaCl, and incubated in this buffer with 15,000 cpm/ml of [125I]HEAT for 2 h in the presence or absence of $10^{-5}$ M phentolamine to define nonspecific binding. After washing in buffer and distilled water, the slides were apposed to Biomax MR2 film for 2-4 days and developed.

Statistics

On the basis of their histology, the animals were divided into two groups, "within" and "outside" the LC. The within group had at least one cannula within 0.2 mm of the LC. Pilot experiments had indicated that unilateral LC injection was sufficient for the above drugs to alter gross behavioral activity in either the novel or home cage test. The 0.2 mm distance was based on other pilot experiments in our laboratory that indicated a diffusion distance of approximately 0.3-0.4 mm for 250 nl infusion of the soluble radiolabeled α1-antagonist, [125I]HEAT, which is structurally similar to terazosin.

Animals showing significant dye penetration of the 4th ventricle were excluded from the study. Comparisons between two drug conditions in the novel cage experiment were evaluated by Bonferronicorrected dependent t-tests. The PE dose-response study in the home cages was analyzed by a one-way ANOVA using each observation as a case and testing for linear and quadratic trends of behavioral activity as a function of the dose of PE. (Since it was not possible to give all animals all five doses of PE, a repeated measures ANOVA could not be employed.) The effect of DSP4 on behavioral responses to terazosin and PE were evaluated by 2×2 factorial ANOVAs followed by Bonferroni-corrected planned comparisons.

Results

Autoradiography

A high density of α1-adrenoceptors can be seen localized to the LC in the autoradiogram in confirmation of the localization of these adrenoceptors (Jones et al., *J. Comp. Neurol.*, 1985; 231:190-208).

Terazosin—Novel Cage Test

Twentyfive rats had injection sites within (200μ) at least one LC and 23 had sites outside both nuclei. Of the 25 within rats, 16 had bilateral and 9 unilateral placements. The effect of terazosin injection (3 nmoles/side) on gross behavioral activity in these animals is shown in Table I.

TABLE I

Effect of terazosin (3 nmoles/side) in LC on behavioral activation in novel cage test

| | Within LC (n = 25) | | Outside LC (n = 23) | |
|---|---|---|---|---|
| | Veh | Teraz | Veh | Teraz |
| Gross movements | 156.0 ± 4.0 | 71.7 ± 11.7[a,d] | 164.0 ± 4.7 | 123.5 ± 7.9[e] |
| Cage midline crosses | 20.5 ± 1.0 | 9.2 ± 2.0[b,e] | 22.4 ± 1.4 | 16.4 ± 1.5[c] |
| Time immobile (min) | 0.09 ± 0.04 | 7.2 ± 1.6[b,d] | 0.09 ± 0.02 | 2.2 ± 0.5[c] |

Rats were microinjected with vehicle and with terazosin (3 nmoles/side) at an interval of 1 week in counterbalanced order. Teraz vs. corresponding vehicle group [a] P < 10−4, [e] P, 0.001 (dependent t-test). Teraz-within vs. teraz outside, [d] P, 0.01, [e] P < 0.001 (independent t-test).

As can be seen, for the entire within group, the drug significantly reduced GMs by 54% (t(24)=7.16, P<$10^{-6}$) and cage Xs by 55% (t(24)=5.44, P<$10^{-4}$), while it significantly increased TI by 77-fold(t(24)=6.66, P<$10^{-5}$). The outside group showed significant changes that were in the same direction but were significantly smaller than the within group. The depressing effect of the drug on GMs became progressively greater the closer the injection was to the LC: percent depression compared to mean of the vehicle group: 45.6±7.0 for within 500μ; 54.0±7.5 for within 200μ; and 63.5±7.2 for direct hits. Bilaterally injected animals did not show a significantly greater inhibition of activity than unilaterally injected animals (percent decreases with respect to vehicle, GMs: unilateral, 50.5±11.1, bilateral, 54.6±9.1, t(23)=0.28 NS;

cage Xs: unilateral, 52.1±16.5; bilateral, 53.7±12.1, t(23)= 0.08 NS; TI-(min): unilateral, 6.1±1.7, bilateral, 7.4±1.4, t(23)=0.58 NS).

PE Reversal of Terazosin Inactivity—Novel Cage

Coinjection of the α1-agonist PE (10 nmoles/side) was found to completely reverse the terazosin-induced inactivity. The effect of terazosin alone in this subset was similar to the effect present in the whole group. Addition of PE produced highly significant increases in GMs (t(4)=16.53, P<0.0001) and cage Xs (t(4)=5.96, P<0.005) and a significant decrease of TI (t(4)=4.46, P<0.002) compared to the terazosin-alone condition. The PE terazosin values were not significantly different than the vehicle values. Although the number of rats used in this comparison is small (5), the changes were highly consistent across all the animals.

PE—Home Cage Test

An independent group of 15 within LC animals, 9 unilateral, and 6 bilateral was used for this experiment. PE produced small dose-dependent increases in GMs (linear trend, F(1,26)=12.38, P<0.002) and cage Xs (linear trend, F(1,26)= 5.94, P<0.03).

To compare the similarity of the behavioral response to PE injection in the home cage with that of exposure to the novel cage (vehicle injection), the cage crosses and rearing responses were calculated as proportions of the GM scores for the rats given 1 nmole PE (home cage) in the above experiment and for those given vehicle injection in the novel cage in the first experiment (a random subgroup of five rats were chosen from the 24 rats) and compared with t-tests. The results are shown in Table II. There were no differences in these proportions between the two groups. The TI measure was also not found to differ between the two groups.

TABLE II

Comparison of the behavioral responses to LC-PE in the home cage with those given vehicle in the novel cage.

|  | GMS | % Xs | % Rears | TI (min) |
|---|---|---|---|---|
| PE in LC (home cage) | 195.2 ± 25.3 | 12.3 ± 2.0 | 33.5 ± 8.0 | 0.98 ± 0.98 |
| Veh in LC (novel cage) | 156.0 ± 4.0 | 14.7 ± 2.3 | 39.6 ± 7.2 | 0.78 ± 0.38 |

Both measures were taken during 0-15 min after placement in cage. PE was given at 1.0 nmole/side. Xs and Rears expressed as % of GM. Values are means and SEM of five rate.

Effects of Pretreatment with DSP4 on Behavioral Effects of Terazosin and PE

DSP4, a noradrenergic neurotoxin, pretreatment by itself had no effect on exploratory activity in either the novel or home cages, but it markedly attenuated the behavioral effects of LC injections of both terazosin in the novel cage and PE in the home cage. For terazosin (novel cage), separate 2×2 (DSP4_terazosin) ANOVAs revealed significant interactions between DSP4 pretreatment and terazosin challenge for GMs (F(1,27)=19.94, P<0.001), Xs (F(1,27)=7.73, P<0.01), and TI (F(1,27)=8.43, P<0.01). Bonferroni-corrected planned comparisons showed that terazosin significantly reduced GMs (F(1,27)=19.59, P<0.001), Xs (F(1,27)=8.49, P<0.05), and increased TI scores (F(1,27)=6.76, P<0.05) in the saline pretreated animals but not in the DSP4 pretreated rats. Although there was a tendency for DSP4 to reduce GMs and Xs in the vehicle (but not terazosin) injected rats in the novel cage, these effects were not statistically significant.

For PE (home cage), there was also a significant DSP4_PE interaction for GMs (F(1,17)=5.69, P<0.03) but not for Xs (F(1,17)=2.10, NS). Planned comparisons indicated that PE challenge significantly increased GMs (F(1,17)=13.71, P<0.004) and Xs (F(1,17)=9.84, P<0.02) in the saline pretreated but not the DSP4 pretreated animals.

Discussion

The present results in rats confirm that the LC participates in the control of exploratory activity, and that this function is regulated, in part, by its α1-adrenoceptors. Microinjection of terazosin, an α1-selective blocking agent, produced marked decreases of GMs and cage Xs and a prolonged immobility in novel surroundings which normally produce high levels of behavioral activation. Although only a single dose of terazosin was used in the present study, a previous study had shown that terazosin injected in the 4th ventricle of the rat produces a dosedependent reduction of behavioral activity in the novel cage test (Stone et al., *Neurosci. Lett.*, 2003; 353: 231-233). That the effect of the drug was exerted on the LC is supported by the findings that the closer the injections were to the LC, the greater their behavioral effects and that the inhibitory effect of terazosin was abolished in animals pretreated with DSP4 to lesion the DNB. These findings are consistent with the fact that the great majority of α1-adrenoceptors of the dorsal pons at this level is localized to the LC, which we confirmed in these animals.

That the effect of terazosin was, in fact, due to its action on α1-adrenoceptors and not to some nonspecific inhibitory or toxic effect was shown by the finding that coinjection of the selective α1-agonist, PE, completely reversed the behavioral inactivity. Moreover, PE injected by itself, with the animals in a low activity environment—the home cage during the light phase—produced a small though significant dose-dependent increase in both gross movements and ambulation (cage crosses), which was also blocked by pretreatment with DSP4. However, since terazosin has some, albeit lower, affinity for α2-adrenoceptors (Hancock et al., *J. Recept. Signal Transduct Res.*, 1995; 15:863-885), we cannot yet exclude the possibility that blockade of the latter adrenoceptors contributed to the effect of the antagonist, specially in view of the fact that α2-adrenoceptors of the LC have been implicated in the control of active behavioral responses (Simson et al., *Neuropharmacology*, 1986; 25:385-389).

The results with DSP4 help to resolve the controversy regarding the role of the LC in exploratory motor activity. Thus, while DSP4 lesion completely prevented the behavioral effects of LC injections of both terazosin and PE, the neurotoxin alone did not significantly impair exploratory behavior in response to sensory stimulation (novel surroundings) at this time period (10 days). This finding demonstrates that the intact LC regulates motor activity, but when lesioned other brain regions compensate for its loss. The most likely source(s) of the compensation are the remaining six brain regions with motoric α1-adrenoceptors and/or DAergic pathways.

Unexpectedly, unilateral blockade of LC α1-adrenoceptors was found to produce the same depressing effect on activity as bilateral blockade. This, however, is in agreement with a previous study in unanesthetized rats in which it was shown that unilateral injection of the α2-agonist, clonidine, in the LC was as effective as bilateral injection in inducing behavioral and EEG sedation (De Sarro et al., *Br J, Pharmacol.*, 1987; 90:675-685). However, other authors, using anesthetized rats, found that clonidine inactivation of one LC was not sufficient to induce EEG slowing (Berridge et al., *Neuroscience*, 1993; 55:381-393). These findings demonstrate that, in the unanesthetized rat, both LCs are necessary for gross behavioral activity in novel surroundings. This view is also consistent with the finding that unilateral LC lesions produce a marked increase in the motor activity response to apomorphine plus high-dose clonidine (De Carvalho, et al., *J. neural*

Transm., 1982; 53:23-37), which is known to involve stimulation of brain α1-adrenoceptors (Anden et al., *Psychopharmacology*, 1973; 29:289-298).

Although α1-adrenoceptors and the LC are involved in arousal and wakefulness (Crochet, et al., *Eur. J. Neurosci.*, 1999; 11:3738-3752; Crochet, et al., *Sleep*, 2003; 26:801-806), their effect on gross behavioral activation appears to be separable from their actions on arousal. Thus, terazosin, given ivt. to mice at a maximally effective behavioral dose, did not impair righting or pain reflexes and did not interfere with muscular tension necessary for the animals to support themselves on a horizontally suspended wire (Stone et al., *Neuroscience*, 1999; 94:1245-1252). Furthermore, stimulation of α1-adrenoceptors in the rat basal forebrain in unanesthetized rats produces EEG and behavioral arousal but no increase in motor activity (Berridge et al., *Behav. Neurosci.*, 2003; 117: 350-259), whereas the present results indicate that stimulation of α1-adrenoceptors in the LC produces increases of motor activity. Therefore, while wakefulness is necessary, of course, for gross behavioral activity, it does not appear to be a sufficient condition for activity to occur in this species.

The neuronal mechanism by which α1-adrenoceptors in the LC control behavioral activity is not yet clearly defined. This is due to the fact that the relationship between LC neurons and LC α1-adrenoceptors is not clear from two key standpoints. First, although previous studies indicate that LC α1-receptor binding sites and α1-mRNA are located in the nucleus proper and in individual LC neurons (Osborne et al., *Br. J. Pharmacol.*, 2002; 135:226-232), it is not known whether these receptors are only or primarily located on LC neurons because they have a different spatial distribution (Chamba et al., *Brain Res Bull.*; 1991; 26:185-193) and cellular localization (Hou et al., *Neuroscience*, 2002; 114:517-521) than α2-adrenoceptors, which are known to exist on LC neurons. Since α1-adrenoceptors may be located on glutamatergic nerve endings in several other brain regions (Marek, et al., *Eur. J. Pharmacol.*, 1999; 367:197-206; Daftary et al., *J. Neurosci.*, 1998; 18:10619-10628), and since the LC receives prominent glutamatergic afferents from the nucleus paragigantocellularis (Ennis et al., *Brain Res.*, 1992; 598:185-195), it is possible that a substantial portion of these receptors is located on glutamatergic nerve endings in the LC.

Second, although α1-adrenoceptors in many other brain regions mediate excitatory electrophysiological effects in their host neurons, either as a result of a direct decrease of potassium conductance (Nicoll et al., *Physiol. Rev.*, 1990; 70:513-565; Osborne et al., *Br. J. Pharmacol*, 2002; 135:226-232) or a facilitation of glutamate neurotransmission (Gordon et al., *J. Neurosci.*, 2003; 23:6223-6231; Marek et al., *Eur. J. Pharmacol.*, 1999; 367:197-206; Boudaba et al., *J. Neuroendocrinol*, 2003; 15:803-810; Ivanov et al., *J. Neurophysiol*, 1995; 74:2427-2436), it is not yet clear that they do this in the LC. Electrophysiological studies with PE have shown that this agonist can enhance LC unit firing rate only in neonatal and not in adult rat brain slices or adult intact brain (of anesthetized rats) (Williams et al., *J. Neurosci*, 1987; 7:3687-2694; Nakamura et al., *Neuroscience*, 1988; 27:921-929). On the other hand, studies with α1-antagonists have shown that blockade of these receptors either in adult rat brain slices (Ivanov et al., *J. Neurophysiol*, 1995; 74:2427-2436) or in the awake dog (Wu et al., *Neuroscience*, 1999; 91:1389-1399) produces a significant decrease in resting firing rate of about 50%, which indicates a tonic excitatory effect of these receptors in the LC. The above failures to find LC excitation in adult brain slices and anesthetized animals may be due to reduced glutamatergic neurotransmission in these preparations, if, in fact, α1-receptors are located on glutamatergic nerve endings. However, our more recent experiments indicate that $α_1$-receptors of the LC are profoundly inhibitory to the neural activity of these neurons as measured from expression of c-Fos and that blockade of these receptors leads to hyperactivity in virtually all LC cells (Stone, et al., *Brain Res.* (2009) 1291, 21-31; Stone, et al., *International Journal of Neuropsychopharmacology* 2011; 14:319-331)

The relationship between LC activity and gross behavioral activity is also controversial. On the one hand, LC activity has long been associated with positive reinforcement in that the nucleus supports self-stimulation which is accompanied by marked increases in behavioral activation (Koob et al., *Brain Res.*, 1978; 146:123-140; Anlezark et al., *J. Neurochem.*, 1975; 24:677-681). Furthermore, some investigators have reported that treatments that increase LC unit firing, such as microinjection of α2-adrenoceptor antagonists and corticotrophin releasing factor, can produce increases in motor activity (De Sarro et al., *Br. J. Pharmacol.*, 1987; 90:675-685; DeSarro et al., *Funct. Neurol.*, 1992; 7:407-412; Butler et al., *J. Neurosci.*, 1990; 10:176-183) which may occur via LC connections with midbrain DAergic neurons (Grenhoff et al., *J. Neural Transm.*, 1993; 93:11-25), the pedunculopontine nucleus (Garcia-Rill, *Brain Res Rev*, 1986; 11:47-63), or spinal interneurons and motoneurons (Clark et al., *Brain Res.*, 1991; 538:231-245; Ono, et al., *Pharmacol Ther*, 1995; 68:105-112; Sqalli-Houssaini, et al., *Brain Res*, 2000; 853: 100-109). However, our more recent studies in which we have assessed the activity of this nucleus after local infusion of 6FNE or terazosin have conclusively shown that LC activity is inversely related to behavioral activation under a variety of conditions (Stone, et al., *Brain Res.* (2009b) 1291, 21-31)

The above findings are in agreement with other results showing that another potent LC-activating treatment, chronic stress, reduces behavioral activation (Simson, et al., *Neuropsychopharmacology*, 1988; 1:287-295; Moore et al., *Neuropsychopharmacology*, 2001; 24:410-419), and that LC activity may be upregulated in major depressive illness (Gold et al., *N Engl J Med*, 1988; 319:348-353; Jedema et al., *Neuropsychopharmacology*, 2003; 28:63-72; Weiss et al., *Depression*, 1996; 3:225-245).

EXAMPLE 2

Methods

Subjects: All experiments were conducted in accordance with the National Research Council Guide for the Care and Use of Laboratory Animals (NIH Publications No. 80-23) and were approved by the New York University Langone School of Medicine IUCAC. A total of 420 Swiss Webster male mice (Taconic), 8-10 weeks old, were subjects. The animals were housed singly with nesting material for 5 d prior to surgery in standard size polycarbonate mouse cages (12.5×17×28 cm) at a room temperature of 22±1° C. under a 12 hr light/dark cycle (lights on 0500 hr). Food and water were available ad libitum.

Surgery: Mice, anesthetized with pentobarbital (70 mg/kg), were implanted stereotaxically with 26 ga cannula guides in the fourth cerebral ventricle (−5.9 mm to Bregma, 1 mm lateral, 3.9 mm ventral to skull surface) as described previously (Stone, et al., *Brain Research* (2009) 1291:21-31). All animals were given 10 days for recovery prior to infusions and behavioral testing.

Drugs used: Dp6FNE was synthesized for the project by the NIMH under the Chemical Synthesis and Drug Supply Program. The following agents were obtained from the following sources: dipivalyl-epinephrine (dipivefrin or dpEPI) (Allergan), propranolol (Sigma), atipamezole (Farmos), prazosin (Pfizer), amphetamine (Sigma), desmethylimipramine (Merrell Dow), fluoxetine (Lilly), clonidine (RBI), buproprion (Burroughs Welcome), ketamine (Fort Dodge), In acute experiments, dp6FNE was administered i.p. 0.1-3 mg/kg, in distilled water (10 ml/kg) containing prazosin (0.2 mg/kg). This dose of prazosin has been shown not to penetrate the blood brain barrier of Swiss Webster mice (Stone et al., 2001; *Eur J. Pharmacol.* 420:97-102) and was used to block peripheral $\alpha_1$-adrenoceptors in the cardiovascular system. Some animals received distilled water vehicle without prazosin for purposes of comparison. In experiment on chronic administration, a daily dose of 0.5 mg/kg in the same vehicle was administered for 11 d. For dpEPI, the vehicle contained both prazosin (0.2 mg/kg) and propranolol (0.5 mg/kg), the latter to block both peripheral and central $\beta$-adrenoceptors. In the receptor identification experiment, prazosin was given at higher dose (5 mg/kg) which has been shown to penetrate the mouse brain and block 30% of cortical $\alpha_1$-adrenoceptors by ex vivo binding (Stone et al., 2001; *Eur J. Pharmacol.* 420: 97-102). Atipamezole was given at a dose (0.5 mg/kg) that produces approximately 70% blockade of sedative and hypothermic effects of a low dose of the selective $\alpha_2$-agonist, dexmedetomidine. (Stone et al., 2001; *Eur J. Pharmacol.* 420:97-102.

Infusion procedure. All experiments were performed between 1000 and 1400 hr. Mice were gently restrained under a layer of gauze and a 33 ga cannula connected by PE 20 tubing to a syringe pump was inserted into the cannula protruding 0.5 mm below the bottom of the guide. A total of 350 nl of solution was infused at 100 nl/min over a 3.5 min period with the cannula remaining in place for 30 seconds after infusion. The animal was then subjected to the behavioral tests described below making the interval between the start of infusion and start of behavioral test 4.5-5 min. This interval has proven sufficient in previous research for the initiation of behavioral changes to the 4th ventricular drugs used in the present study. The animals received either vehicle (saline), 6FNE (Sigma-RBI), the $\alpha_1$-antagonist, terazosin (TER, Sigma-RBI), the $\alpha_2$-antagonist, atipamezole (ATI, Farmos) or the $\alpha_2$-agonist, dexmedetomidine (DEX, Farmos), singly or in combination, in doses ranging from 0.04-10 nmoles per mouse. Doses were determined from pilot and previous experiments (Lin, et al., *Synapse* (2008) 62:516-523; Stone, et al., *Psychopharmacology* (2005) 183:127-132; Stone, et al., *Brain Res.* (2009b) 1291:21-31). TER (Hancock, et al., *J.Recept.Signal Transduct. Res.* (1995) 15:863-885), ATI (Haapalinna, et al., *Naunyn-Schmied.Arch.Pharmacol.* (1997) 356:570-582), and DEX (Takano, et al., *J.Pharmacol.Exp.Ther.* (1991) 258:438-446) all have low nanomolar affinities for their respective receptors and were used at doses of ≤1 nmole which we have shown maintain receptor specificity in this brain region (Stone, et al., *Psychopharmacology* (2005) 183:127-132). All drugs were prepared freshly each day in saline.

At 70 min after drug infusion all animals were deeply anesthetized with a combination of isoflurane and urethane (2.2 g/kg, i.p.) and perfused intracardially with 4% paraformaldehyde for subsequent immunohistochemistry and histological examination of the cannula tip with respect to the 4th ventricle.

I.P. Injections: Independent groups of naive non-implanted animals were injected i.p. with vehicle (saline) or desmethylimipramine (DMI, Merrell Dow), 10 mg/kg, 3×(24, 12 and 0.5 h) prior to the following antidepressant tests.

Forced swim test: Separate groups of animals were used for each of the following behavioral tests. A modification of the Porsolt procedure for mice was used for the forced swim test (Porsolt, et al., *Arch.int.Pharmacodyn.Ther.* (1977) 229:327-336). The animals were given 2 videorecorded swims 24 hr apart in a 20 cm dia cylinder of 13 cm deep 25° C. water. The first swim was 15 min and the second 5 min. Prior to the second swim, the mice were matched on immobility times of the first swim and randomly assigned to ivt. vehicle or drug groups. Ivt. drugs were infused immediately before the second swim. Groups given vehicle or DMI i.p. were injected initially 5 min after the first swim and finally 30 min before the second swim. Alternately, the drugs were administered ip 15 min prior to the test. Videodisks were rated blind by two observers for times immobile and climbing in the second swim as described previously (Stone, et al., *Brain Research* (2009) 1291:21-31); (Lucki, et al., *J.Clin.Psychiatry* (2004) 65 (Suppl 4):11-24; Stem, et al., *Psychopharmacology* (1985) 85:367-370).

Tail suspension test: The procedure of Stem, et al., *Psychopharmacology* 1985; 85: 367-370 was used. Immediately following intraventricular infusion or 30 min after the third i.p. injection, the animals were taped by the tail 72 cm above a padded platform for 6 min during which time they were videorecorded. Disks were subsequently rated blind as above for times immobile during the last 4 min of the test. This period also gives results comparable to the full 6 min period (Cryan, et al., *Neurosci. Biobehav. Revs*. (2005) 29:571-625).

Repeated open space forced swim procedure: This test is a modification of the acute forced swim paradigm that responds to chronic and not acute administration of a variety of antidepressants including tricyclics, serotonin selective reuptake inhibitors and monoamine oxidase inhibitors but not anxiolytics or antipsychotics (Stone, et al., *Progress in Neuropsychopharmacology and Biological Psychiatry* (2007) 31:1196-1207; Stone, et al., *Pharmacol. Biochem. Behav.* (2008) 91:190-195; Sun, et al., *J.Neurosci.Methods* (2003) 126: 35-40; Sun, et al., *J.Pharmacol.exp.Ther*. (2006) 316: 926-932). In this procedure, mice are swum for 15-20 min/d for 4 d in rat tub cages (24×43×23 cm, w×h×l) filled with 13 cm high luke-warm water (32-34° C.) and thereafter once or twice a week. This schedule produces a progressive reduction of active swimming along with a concomitant increase in immobility (floating) which persist unaltered for weeks after the last test and generalize to increased immobility in the tail suspension test (Stone, et al., *Pharmacol. Biochem. Behav.* (2008) 91:190-195). These behaviors have been found to be accompanied by activation with minimal adaptation of Fos expression in the PVH (Stone, et al., *Progress in Neuropsychopharmacology and Biological Psychiatry* (2007) 31:1196-1207) and by a significant reduction in cell proliferation rate in the subventricular zone (Stone, et al., *Pharmacol. Biochem. Behav.* (2008) 91:190-195). In the present experiment, the animals were matched on immobility level of the $4^{th}$ swim into vehicle and drug groups and infused ivt. just prior to the $5^{th}$ swim. Groups given i.p. injections were dosed initially 5 min after the 4th swim and finally 30 min prior to the 5th swim. Discs were rated as above on immobility and distance swum (number of quadrants entered).

Endotoxin Induce Anhedonia (FUST):

To determine if dp6FNE is also active in an anhedonia-based model of depression, the compound was tested for its ability to reverse an endotoxin-induced inhibition of the female urine sniffing test (FUST), a non-nutritive hedonic behavior which is unaffected by the acute anorexic effects of antidepressants (Malkesman et al., *Biological Psychiatry* 2010; 67: 864-871). Endotoxin was used as the depression-inducing agent because it has been established that cytokine release is a key factor in mediating the depressive effects of stress (Koo et al., *Proceedings of the National Academy of Sciences, USA* 2010; 107: 2669-2674) and because the endotoxin model is significantly briefer but yields largely the same information on hedonic behavior as the chronic mild stress model (Frenois et al., *Psychoneuroendocrinology* 2007; 32: 516-531). The RFS model was not used for this purpose because it is not severe enough to reliably produce anhedonia in this species (Stone et al., *Current Protocols in Neuroscience*, In press).

For the FUST, naive mice were trained to sniff estrous urine (verified by vaginal smears) from a cotton swab inserted in the home cage for 3 min/d over 3 d by a modification of above procedure. Briefly, on each day a swab containing 50 μl of saline was first inserted 5 in into and approximately 2.5 in above the floor of the home cage and left there for 45 min to habituate the animal. The mouse was then given an i.p. needle puncture for habituation to the handling and injection procedures and 15 min later presented with the swab containing 50 μl of estrous urine for 3 min. A positive response was defined as observable sniffing with the nares within approximately 1 mm of the swab. Using a 2×2 Endotoxin×dp6FNE experimental design, the animals were first matched on total time sniffing in the 3rd test into a control and an endotoxin group and administered distilled water or lipopolysaccharide, 400 μg/kg, i.p., respectively. 24 h later, these 2 groups were each subdivided into matched prazosin-vehicle and dp6FNE/prazosin groups which were tested for FUST behavior 15 min after receiving i.p. injections of these respective solutions.

Open Field Motor Activity and Anxiety:

To determine if dp6FNE/prazosin had any motor stimulating, sedative or anxiolytic actions, naive mice injected 15 min earlier with the pro-drug at 0.1-3 mg/kg were exposed to an open field for 1 h. For purposes of comparison, some animals received instead d-amphetamine, 2 mg/kg, i.p. Total quadrants entered and time in the center area of the field as a ratio to the total distance traveled were rated from videorecordings.

1LPS model of depression (anhedonia): A modification of the Frenois et al (2007) model of LPS-induced anhedonia in the mouse was used to obtain a non-motoric index of depressed behavior. In this model, trained mice show a marked decrease in preference for a sweet solution 24-48 h after a systemic dose of LPS (830 μg/kg, i.p.), a time when they have recovered from the sickness behavior and anorexia caused by the acute effects of the toxin.

For the model, the animals were first implanted with 4th ventricular cannulas as above and, during the recovery period, trained to drink diluted sweetened condensed milk solution (Magnolia 1:3 v:v milk:tap water) by 15 min presentations every other day for 7-10 d. Once the animals showed reliable drinking (above 1.75 ml), they were then matched on intakes into two groups which received LPS (830 μg/kg, i.p.) or vehicle (saline) at 10-1100 h and then, 48 later, subdivided again into groups that received ivt. vehicle or 3 nmoles of 6FNE just prior to the final milk intake test. Animals given i.p. injections were dosed 14, 12 and 0.5 h prior to the last test.

Because LPS has potent anorexic effects which might influence the above experiment, a control experiment was run to determine if there was still significant anorexia remaining at 48 h post LPS infusion. For this experiment, implanted animals were trained to eat in a 1 h period by presenting food in the home cage for 1 h following a 12 h period of food deprivation and preceding a second 12 h period of deprivation. Once the animals' hourly intakes had asymptoted (2 weeks of biweekly training sessions), they were matched on preceding intake levels and randomly assigned to the vehicle and LPS groups which were injected i.p. with their respective solutions 48 h prior to a subsequent 1 h intake test.

Open field motor activity: Implanted mice were placed singly in an open field (46×46×33 cm clear Plexiglas) and permitted to explore freely and habituate for 60 min. The animals were then either left undisturbed in the field or removed and infused with either vehicle or 6FNE (3 nmoles) and replaced in the field for a further 15 min. For comparative purposes a further group of implanted animals, similarly habituated to the field, was given an i.p. injection of d-amphetamine (5 mg/kg) prior to the final 15 min exposure. Movement in the field was videorecorded and was subsequently rated blind for the number of quadrants entered as well as the amount of time spent not touching the walls ("time in the center of the field").

Immunohistochemistry: Methods used for single and double-label Fos and Fos+tyrosine hydroxylase immunohistochemistry have been described in detail elsewhere (Stone, et al., *Brain Research* (2009) 1291:21-31). In brief, at 70 min after drug infusion deeply anesthetized (isoflurane plus urethane, 2.2 g/kg) mice were perfused intracardially with saline (25 ml) and 4% paraformaldehyde (45 ml), and the sucrose-treated brains were sectioned at 35 p and stained either singly for Fos (PVH, lateral septal nucleus, shell of nucleus accumbens (NAC)) or doubly for Fos and tyrosine hydroxylase (LC). Rabbit anti-fos (Oncogene Science 1:20,000) and chicken anti-tyrosine hydroxylase (Novus Biologicals, 1:5, 000) were primary antibodies. Single-label staining involved nickel intensified-diaminobenzidine localization of the secondary biotinylated antibody and avidin-biotin-peroxidase complex. Double-label staining involved the use of Alexa-488 labeled secondary anti-rabbit and Alexa-594 labeled secondary anti-chicken antibodies. The PVH and LC were counted in all sections throughout the extent of each nucleus whereas the lateral septal nucleus (+0.98, +0.5 mm Bregma) and NAC (+1.5, 0.98 mm Bregma) were counted by a profile method at two levels, which not being significantly different, were averaged. In all sections, to preclude biasing in the placement of counting frames, large frames comprising the total two dimensional extent of the target structures were counted for every Fos-positive cell by ImageJ. Double-labeled LC cells were defined as those having a fluorescently labeled cytoplasm (TH) and nucleus (Fos) greater than twice background fluorescence.

Histology

Only those animals showing accurate placement of the cannulas in the 4th ventricle are included in the study which constituted 82% of the total number. Cannula position was assessed from sections through the ventricle that were processed for Fos/TH double-labeling. Penetration of the roof of the ventricle together with obvious distension of the lumen was taken as evidence of accurate placement.

Statistics

All analyses involved one- or two-way ANOVAs followed by a small number of planned comparisons that were evaluated at a per comparison error rate of $\alpha=0.05$ (Keppel, *Design and Analysis. A Researcher's Handbook. In.* Prentice-Hall, Inc., Englewood Cliffs, N.J. (1991) 165-167) Since the ivt. 6FNE-behavior dose-response curves were uniformly U-shaped, the quadratic trend components were computed followed by a single contrast between the peak-dose group and vehicle. The i.p. DMI group and its vehicle control were compared with independent t-test. To compare the effects of the peak ivt. 6FNE effect with i.p. DMI, behavioral scores were calculated as percentages of their respective mean vehicle levels and compared by t-test. To reduce variability and equate variances, open field scores (quadrants entered and time in center of field) were first converted to logs prior to ANOVAs.

Figure 6A:
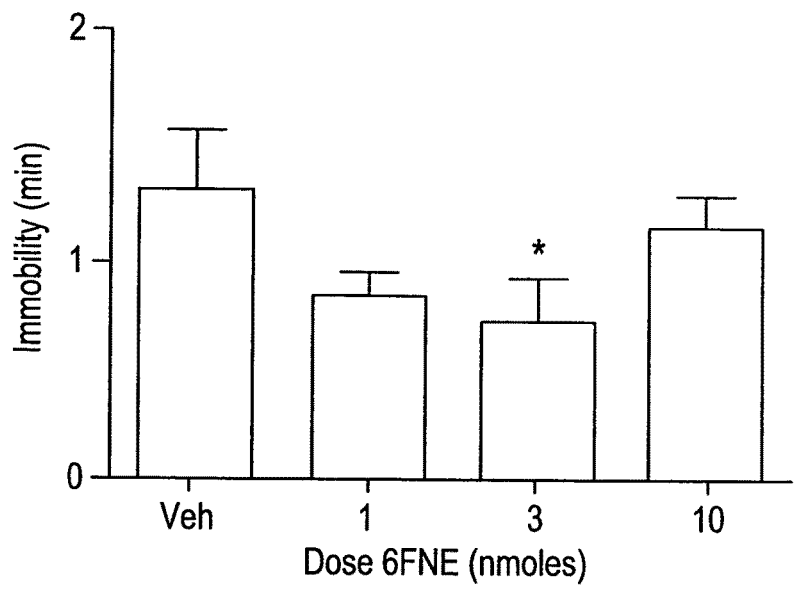
FIG. 6 demonstrates the effect of acute ivt. 6FNE on Porsolt forced swim test. Mice were swum twice, for 15 min on day 1 and 5 min on day 2. Shown are results of second day test for immobility (top) and climbing durations (bottom). N=7-9. *$p<0.05$ versus vehicle, planned contrast.
Figure 6B:
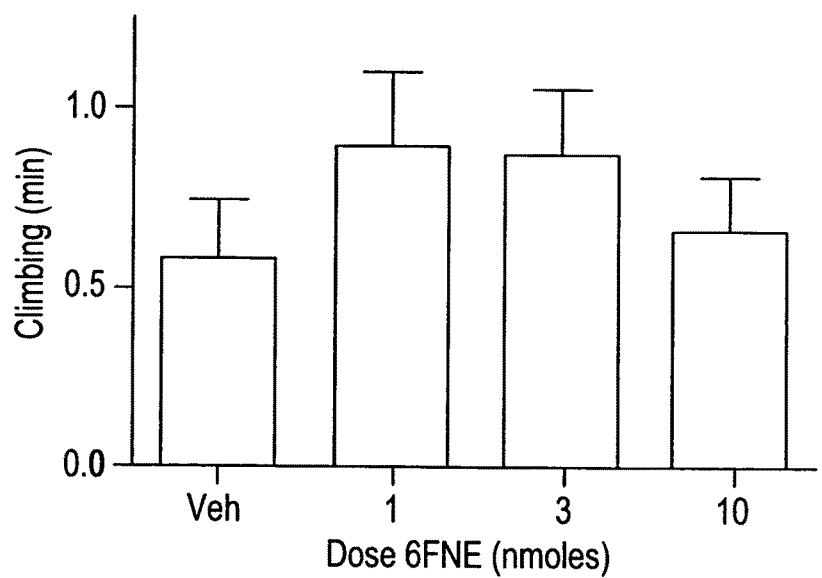

Results
1. Acute Forced Swim (Porsolt Test) (FIG. 6)

Ivt. 6FNE: One-way ANOVAs failed to show statistical significance for an overall 6FNE effect on either immobility ($F_{3,30}=2.02$, p>0.1) or climbing duration ($F_{3,30}=1.15$, NS). However, the dose-response curves for both behaviors were found to be U-shaped and therefore quadratic trends as a function of drug dose were computed. A significant trend was found for immobility ($F_{1,30}=5.32$, p<0.05) but not for climbing ($F_{1,30}=2.13$, p>0.1). The peak reduction of immobility occurred at 3 nmoles and differed significantly from vehicle ($F_{1,30}=4.87$, p<0.05).

I.P. DMI: Subacute administration of 10 mg/kg of the tricyclic produced a significant reduction in immobility ($t_{16}=2.51$, p<0.05). Expressed as percentages of their respective vehicle control means, the reductions produced by i.p. DMI and ivt. 6FNE at 3 nmoles were not significantly different (6FNE, 55.8±0.14.1%; DMI, 58.0±0.11.9%; t).

Figure 1A:
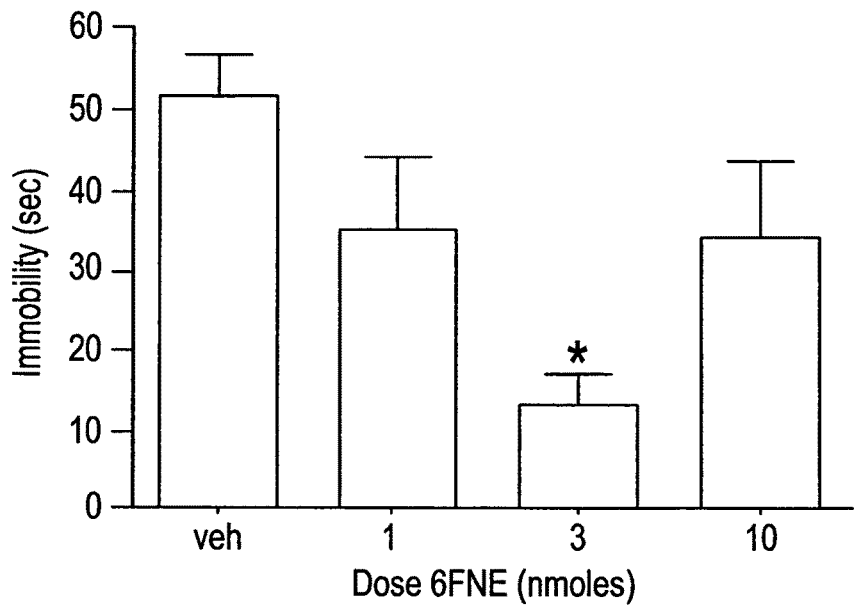
FIG. 1 provides a comparison of ivt. 6FNE and ivt. dexmedetomidine on the tail suspension test. *$p<0.05$, **$p<0.001$ versus Vehicle. N=8-10 mice/gp.
Figure 1B:
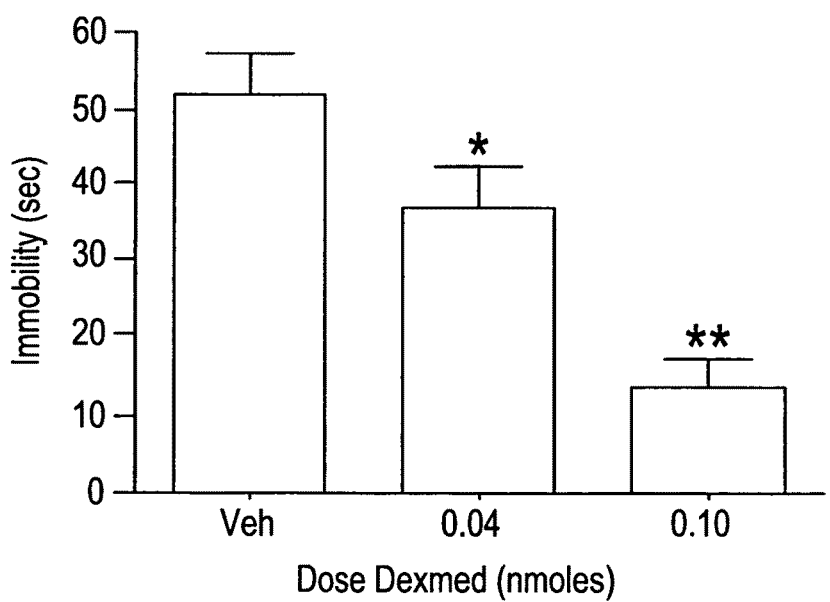
Figure 2A:
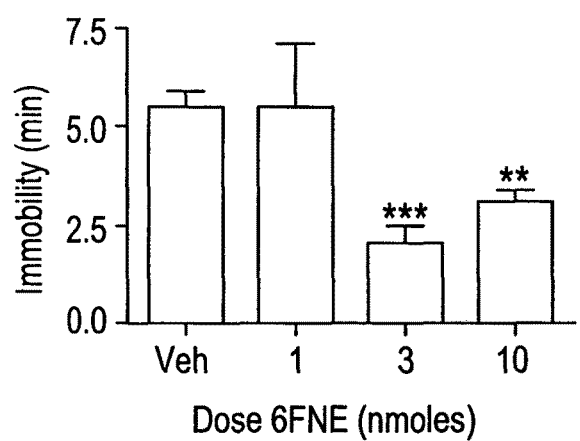
FIG. 2 demonstrates a comparison of ivt. 6FNE and ivt. dexmedetomidine on the repeated open-space forced swim (RFS) test. *$p<0.05$, $p<0.01$, *$p<0.001$ versus Vehicle. N=7-10 mice/gp.
Figure 2B:
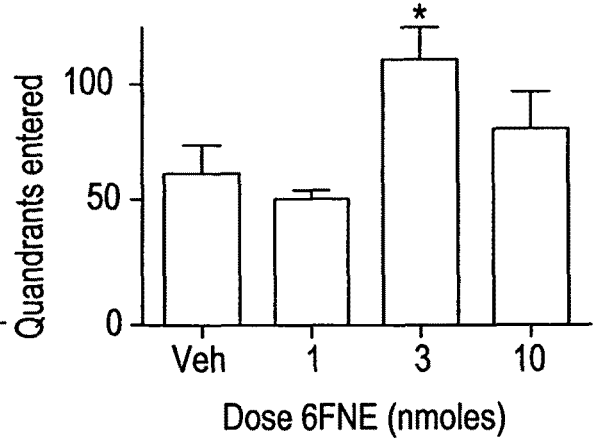
Figure 2C:
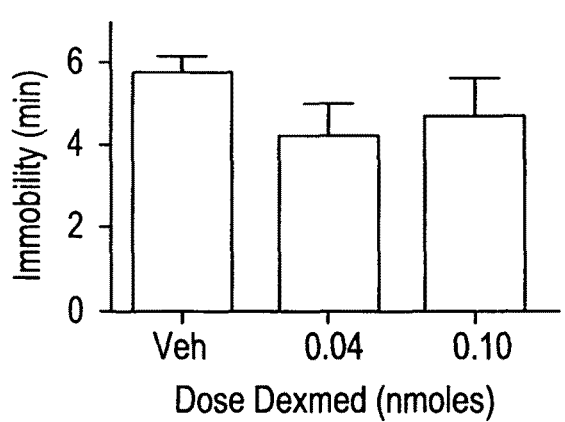
Figure 2D:
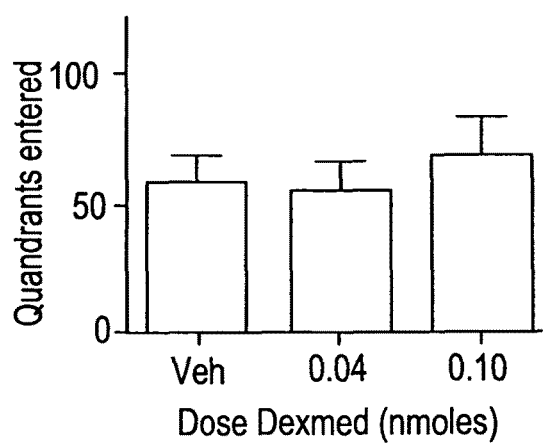

2. Tail Suspension Test (FIG. 1, Upper)

Ivt. 6FNE: 6FNE produced a significant overall reduction in immobility by one way ANOVA ($F_{3,45}=5.38$, p<0.005). As with the above Porsolt test, a U-shaped dose-response curve was obtained which yielded a significant quadratic trend ($F_{1,45}=6.65$, p<0.05). The 3 nmoles dose produced the greatest reduction from vehicle level ($F_{1,45}=16.10$, p<0.001).

I.P. DMI: The subacute i.p. tricyclic significantly reduced immobility ($t_{13}=2.12$, p=0.05) but was significantly less effective than ivt. 6FNE at 3 nmoles (6FNE, 24.7±7.8% vehicle control, DMI, 64.7±20.7%, $t_{16}=2.60$, p<0.02).

3. Repeated Open-Space Forced Swimming Test (FIG. 2, Upper)

Ivt. 6FNE: One-way ANOVAs revealed that 6FNE dose-dependently reduced immobility ($F_{3,24}=8.69$, p<0.001) and produced a borderline increase in distance swum ($F_{3,24}=2.47$, p<0.1). Once again the dose-response curves were U-shaped and the quadratic trend component was of borderline significance for immobility ($F_{1,24}=2.84$, p<0.1) but significant for distance swum ($F_{1,24}=4.18$, p<0.05). The peak effect for immobility reduction occurred at 3 nmoles ($F_{1,24}=24.6$, p<0.0001) whereas for distance swum was at 10 nmoles ($F_{1,24}=6.82$, p<0.05).

I.P. DMI: Subacute administration of the tricyclic at 10 mg/kg failed to affect immobility or distance swum and was significantly less effective than ivt. 6FNE on both behaviors (immobility, 6FNE, 36.7±9.2% vehicle control; DMI, 94.8±7.1%; $t_{22}=4.02$, p<0.001; distance swum, 6FNE, 193.4±22.8%; DMI, 102.0±20.7, $t_{22}=2.12$, p<0.05).

4. LPS Anhedonia (FIG. 7)

This model was restricted to ivt. 6FNE treatment because the subacute i.p.DMI was found to result in anorexia and markedly reduced sucrose intakes. The effects of 6FNE and LPS on mean sucrose preferences, and intakes of sucrose and water are shown in the figure. Each of the variables was analyzed with a 2×4 (LPS×6FNE) ANOVA. Sucrose preference was markedly reduced by LPS pretreatment ($F_{1,48}=15.21$, p<0.001) and was rescued by 6FNE ($F_{1,48}=4.06$, p<0.05). Although the linear interaction between LPS and 6FNE was not significant, there was a significant LPS×quadratic trend interaction ($F_{1,48}=4.37$, p<0.05) with the LPS—but not vehicle-pretreated mice showing an inverted U-shaped dose-response curve of preference to 6FNE. The changes in sucrose preference were due to alterations in both sucrose and water intake. For sucrose intakes, there was a significant interaction between LPS pretreatment and acute 6FNE ($F_{3,48}=5.55$, p<0.005). LPS in the absence of 6FNE produced a borderline reduction in intake ($F_{1,48}=2.90$, p=0.09) while 6FNE produced an inverted-U-shaped increase in the LPS—but not vehicle (i.p.)—pretreated animals (interaction of LPS×quadratic trend of 6FNE, $F_{1,48}=15.01$, p<0.001). For water intake, the only significant effect was an overall increase in the LPS-pretreated animals ($F_{1,41}=17.39$, p<0.001).

LPS failed to significantly alter 1 h food intake at 48 h post injection (−13%, $t_9=0.81$, NS).

Figure 8:
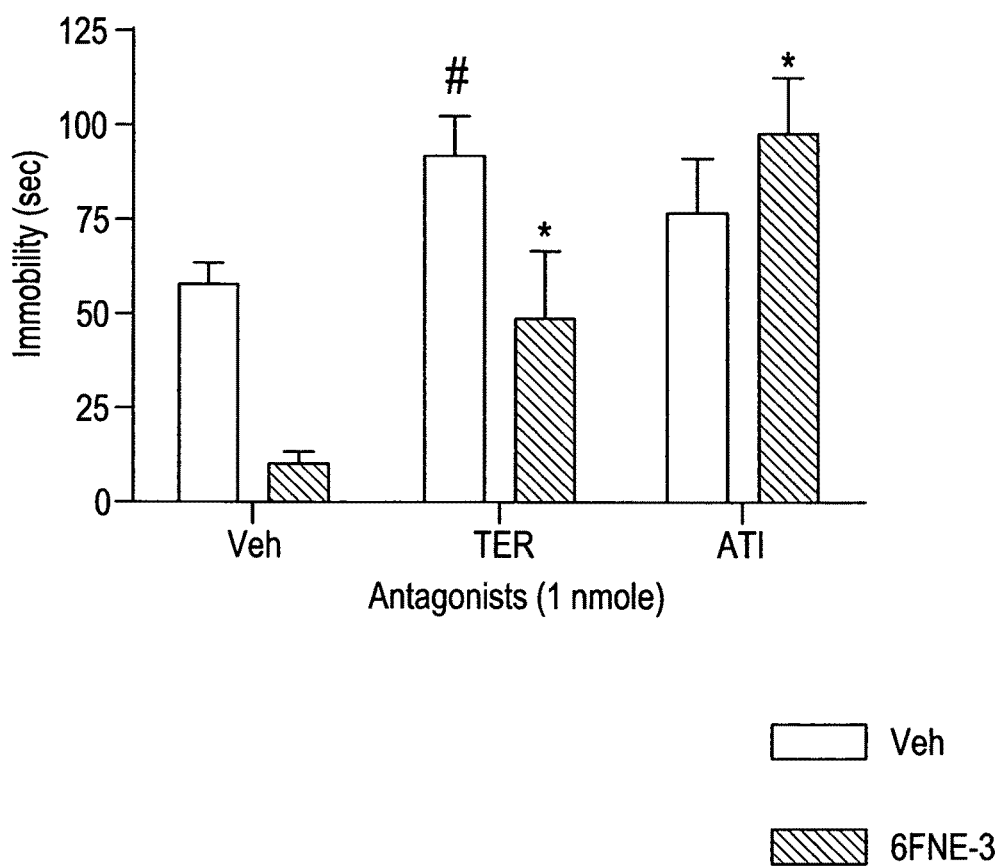
FIG. 8 demonstrates the effect of blockade of α1-(TER) and α2-(ATI) adrenoceptors on anti-immobility effect of 6FNE in tail suspension test. 6FNE was administered at 3 nmoles in the presence or absence of either antagonist (1 nmole) immediately prior to the test. N=7-9. *$p<0.0001$ versus 6FNE-alone, #$<0.05$ versus Vehicle-alone, Bonferroni test.

5. Effect of $\alpha_1$- and $\alpha_2$-Receptor Antagonists on 6FNE Effect in Tail Suspension Test (FIG. 8)

The figure shows the effect of blockade of $\alpha_1$- and $\alpha_2$-receptors with TER and ATI, respectively, on the antidepressant effect of 6FNE in the tail suspension test. A 2×3 (6FNE× Antagonist) ANOVA revealed significant main effects of 6FNE ($F_{1,49}=6.63$, p<0.05) and Antagonist ($F_{2,49}=19.87$, p, <0.0001) with a significant interaction between the two ($F_{2,49}=5.71$, p<0.01). Both TER ($F_{1,49}=18.47$, p<0.0001) and ATI ($F_{1,49}=32.55$, p<0.0001) significantly increased immobility when coinfused with 6FNE (compared to 6FNE+vehicle) however ATI totally abolished the effect of 6FNE (i.e., there was no longer a significant difference between the vehicle-only group and the 6FNE+ATI group) whereas TER did not (i.e, there was still a significant difference between vehicle-only and 6FNE+TER groups, $F_{1,49}=8.99$, p<0.05). On the other hand TER significantly increased immobility in the vehicle-treated animals (TER+vehicle versus vehicle-only groups, $F_{1,49}=9.13$, p<0.05) whereas ATI had no effect in this group (ATI+vehicle versus vehicle-only, $F_{1,49}=3.38$, NS).

Figure 9A:
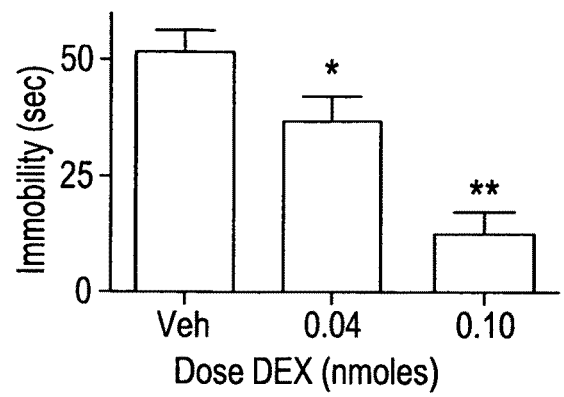
FIG. 9 demonstrates the effect of an acute ivt. α2-agonist (dexmedetomidine, DEX) on the tail suspension and repeated openspace forced swim tests. N=7-9. *$p<0.05$, **$<0.001$ versus Vehicle, planned contrast.
Figure 9B:
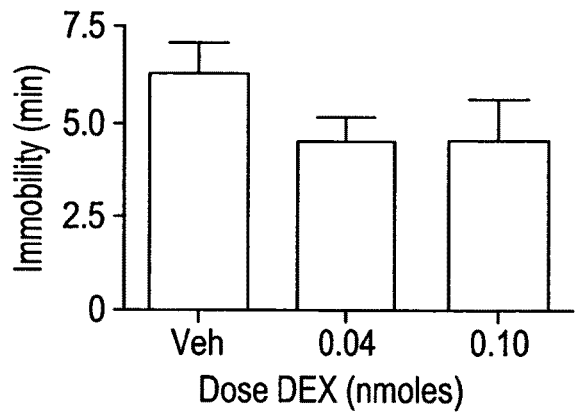
Figure 9C:
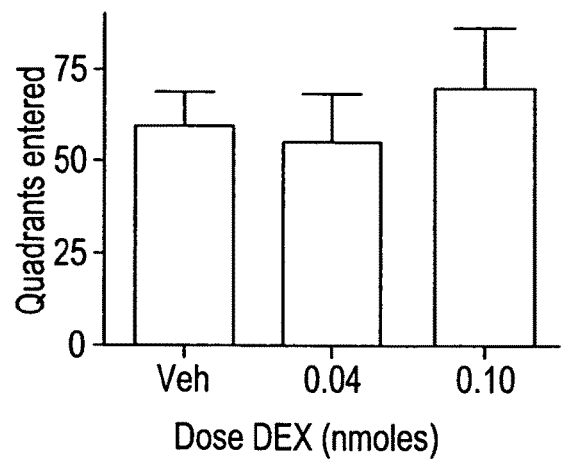
Figure 10A:
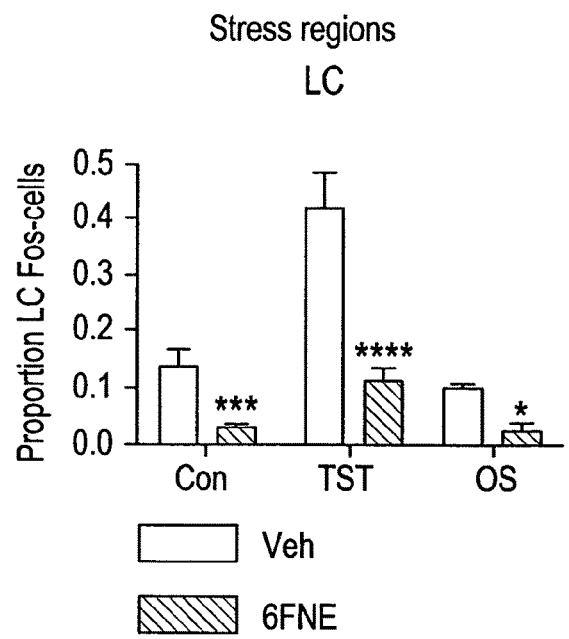
FIG. 10 demonstrates the effect of acute ivt. 6FNE (3 nmoles) on fos expression in two stress regions (LC and PVH) and two motivational areas (septal region and nucleus accumbens, NAC). Fos level in LC is expressed as proportion of total tyrosine hydroxylase cells expressing the gene and in PVH is number of fos positive cells per total nucleus. In nucleus accumbens and septal region fos expression is number of fos positive cells per 0.1 mm2. N=5-6/gp. *$p<0.05$, $<0.01$, *$<0.001$, ****$<0.0001$ versus vehicle, planned contrast.
Figure 10B:
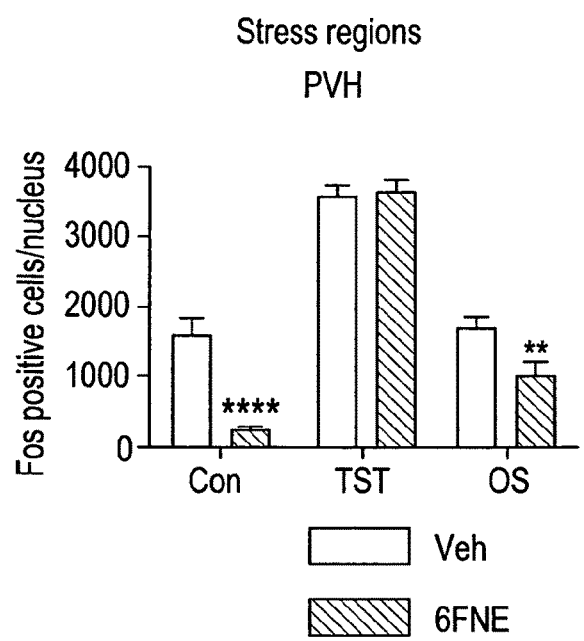
Figure 10C:
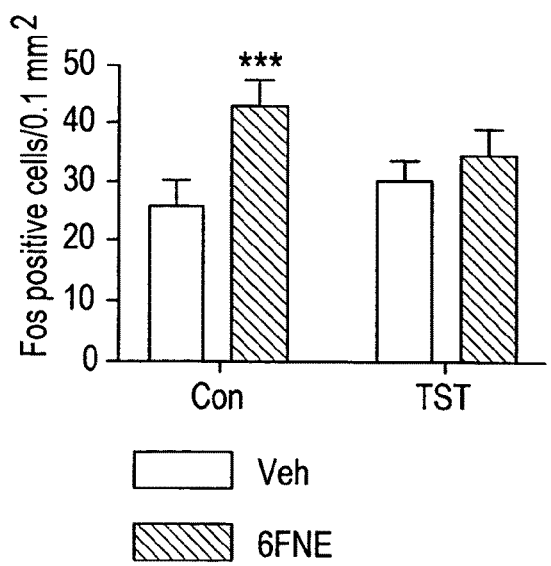
Figure 10D:
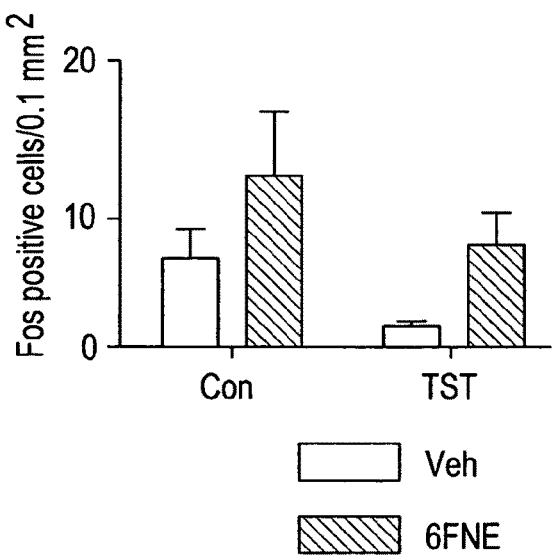

6. Effect of a Selective $\alpha_2$-Agonist, DEX, on Depression Tests (FIG. 9

The figure shows the effects of DEX on behavior in the tail suspension and repeated open-space forced swim tests. As can be seen, the $\alpha_2$-agonist produced a significant dose-dependent decrease in immobility in the tail suspension test that was similar in magnitude to that produced above by 6FNE ($F_{2,21}=14.52$, p<0.001). However, the compound was less effective in the repeated open-space swim test where it failed to have an overall significant effect on immobility ($F_{2,21}=1.52$, NS) or distance swum ($F_{2,21}=0.24$, N/S) although it did produce a borderline significant reduction in immobility at the 0.04 nmoles dose ($F_{1,21}=2.96$, p<0.1).

7. Open Field Motor Activity (FIG. 4)

Total quadrants entered in the 15 min post infusion test period was significantly different between the unhandled, vehicle-, and 6FNE-infused groups ($F_{2,26}=7.47$, p<0.005). Planned comparisons showed that vehicle infusion significantly reduced activity in this interval compared to the non-infused group ($F_{1,26}=6.48$, p<0.02) and that 6FNE infusion completely rescued the activity as shown by the lack of difference between the 6FNE and the non-infused group ($F_{1,26}=0.91$, NS) and the significant increase in the 6FNE over the vehicle group ($F_{1,26}=14.26$, p<0.001). I.P. amphetamine, which was analyzed separately, produced a ten-fold increase in locomotion during this period which was far greater than the increase seen after 6FNE ($t_{10}=5.33$, p<0.001).

Time in the center of the field was affected similarly to total quadrants with a significant overall difference between the 3 groups ($F_{2,26}=5.72$, p<0.01), a significant reduction in the vehicle compared to the non-infused group ($F_{2,26}=7.01$, p<0.02) and a complete rescue by 6FNE infusion (6FNE versus vehicle, $F_{2,26}=9.75$, p<0.005; 6FNE versus non-infused, ($F_{2,26}=0.05$, NS).

8. Effects of 6FNE and Depression Test on c-Fos Expression in Stress- and Motivational-Responsive Brain Regions (FIG. 10)

Fos levels in the stress- and motivation-related regions in response to Depression test and 6FNE were analyzed with separate two-way (Depression test×6FNE) ANOVAs. In the stress responsive areas, the Depression test produced a significant overall increase of Fos expression (LC, $F_{2,27}$=21.45, p<0.0001; PVH, $F_{2,27}$=136.98, p<0.0001) whereas 6FNE produced a significant overall reduction (LC, $F_{1,27}$=35.19, p<0.0001; PVH, $F_{1,27}$=27.77, p<0.0001). In addition to these main effects there were significant interactions between Depression test×6FNE in the LC ($F_{1,27}$=47.52, p<0.0001) and PVH ($F_{2,27}$=9.25, p<0.001). These resulted from the facts that (a) an overall increase in Fos after Depression test was observed for the tail suspension but not for the repeated open-space swim test and (b) in the PVH, 6FNE significantly reduced expression in the controls ($F_{1,27}$=38.93, p<0.0001) and open-space ($F_{1,27}$=6.84, p<0.05) but not in the tail suspension group.

In the motivation-related areas, the Depression test failed to alter Fos expression whereas 6FNE produced an overall increase rather than a decrease (NAC, $F_{1,17}$=3.59, p<0.1; lateral septal nucleus, $F_{1,17}$=6.07, p<0.05) with no interaction between the two variables. (The assay of NAC and septal regions in the open-space swim group was precluded by a shortage of the batch of the antibody used).

Figure 11:
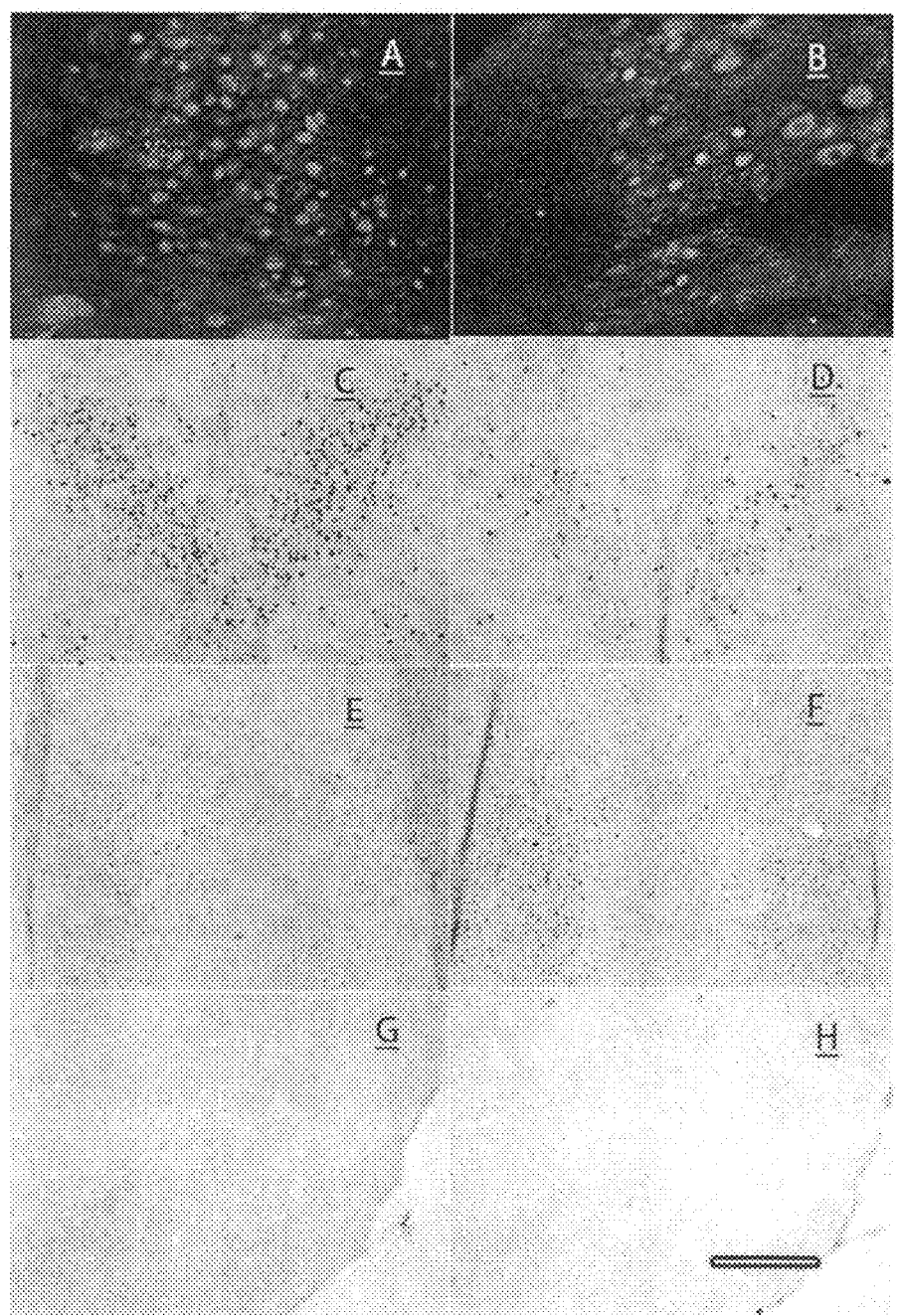
FIG. 11 provides stained sections of representative animals from results in FIG. 3 infused with either vehicle (A, C, E, G) or 3 nmoles of 6FNE (B, D, F, H). A & B—LC of mice subjected to tail suspension stained for both Fos (green nuclei) and tyrosine hydroxylase (red cytoplasm). C & D—PVH of mice subjected to repeated open space swim stress. E & F, —Lateral septal nucleus of mice under control conditions. G & H—NAC under control conditions. Bar=200μ (E-H), 500μ (A-D).

Representative single- or double-label stained sections of the above significant effects in the LC, PVH, lateral septal nucleus and NAC are shown in FIG. 11.

EXAMPLE 3

Experiments with dp6FNE

9. Acute Forced Swim (Porsolt Test)

Figure 12A:
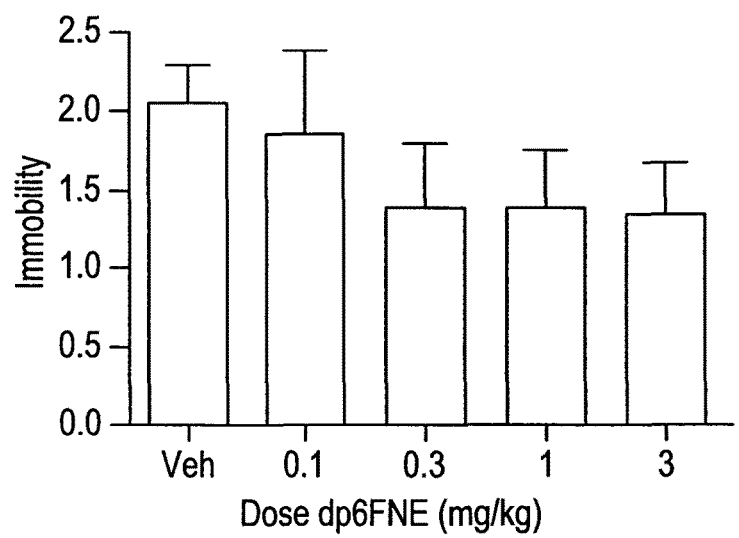
FIG. 12 demonstrates the effect of acute i.p. dp6FNE/prazosin given 15 min prior to the acute (Porsolt) forced swim (upper panel) or tail suspension test (lower panel). N=7-10 . . . *$p<0.05$ versus vehicle, by planned contrast.
Figure 12B:
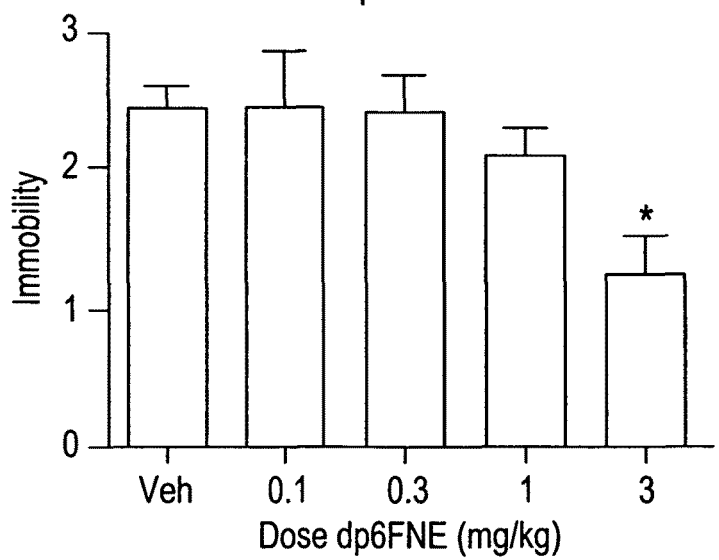

Effects of dp6FNE on the acute forced swim test are shown in FIG. 12 (Upper panel). A one-way ANOVA failed to show a significant reduction of immobility after dp6FNE/prazosin ($F_{4,36}$=1.88, NS) in the forced swim test, however, the drug produced a significant linear trend of reduction of floating with increasing dosage ($F_{1,36}$=6.38, p<0.02).

10. Tail Suspension Test (TST)

Effects of the pro-drug are shown in FIG. 12 (Lower panel). The compound produced a highly significant reduction in immobility ($F_{4,36}$=11.67, p<0.0001) which was dose-dependent (linear trend component, $F_{1,36}$=29.53, p<0.0001).

11. Repeated Forced Swim (RFS)

Figure 13A:
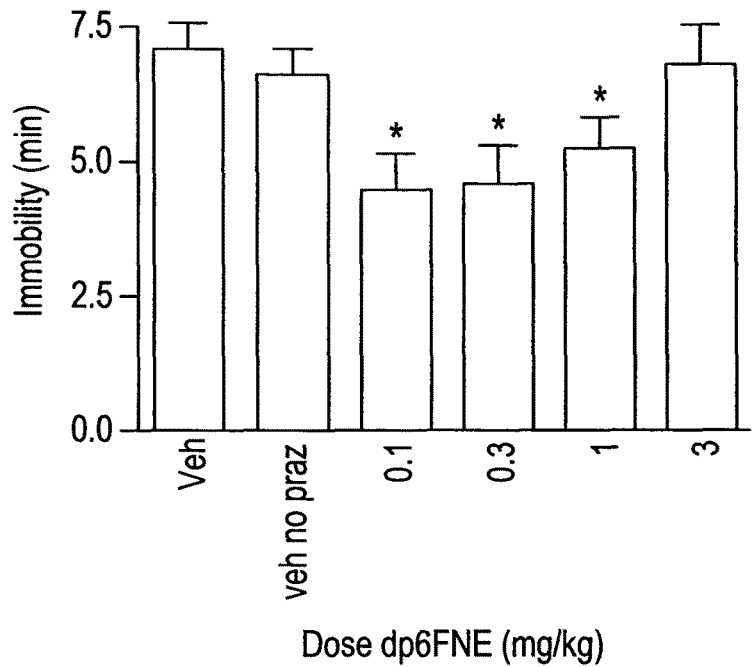
FIG. 13 demonstrates the effect of acute dp6FNE/prazosin to the repeated forced swim test. Immobility duration (upper panel) and distance swum (lower panel) are shown for the $5^{th}$ swim in a series of 5 daily swims 15 min after administration. Figures show the groups given vehicle with and without prazosin (0.2 mg/kg). N=10-13. *$p<0.05$, ***$<0.001$ versus combined vehicle groups, planned contrast.
Figure 13B:
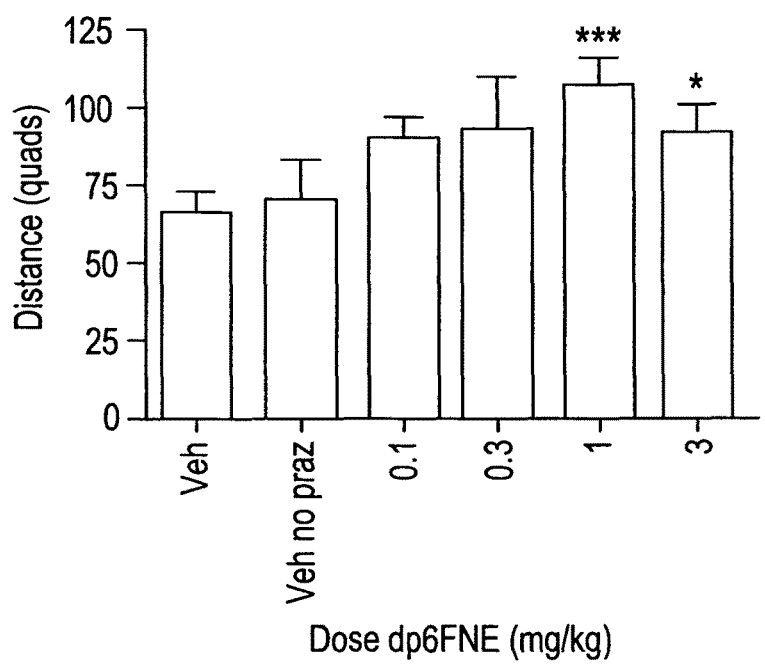

In the RFS, dp6FNE/prazosin produced a significant overall reduction of immobility ($F_{4,61}$=3.67, p<0.01) and a significant overall increase in distance swum ($F_{4,61}$=3.84, p<0.01) (FIG. 13). The reduction of immobility was better fit to a quadratic trend ($F_{1,61}$=8.36, p=0.005) with the lowest dose (0.1 mg/mg) showing the greatest effect whereas the increase of distance swum was linearly related to dosage ($F_{1,61}$=8.03, p<0.01) with the higher doses (1 and 3 mg/kg) having the greatest actions.

12. Comparison with Other Antidepressants (RFS)

Figure 14A:
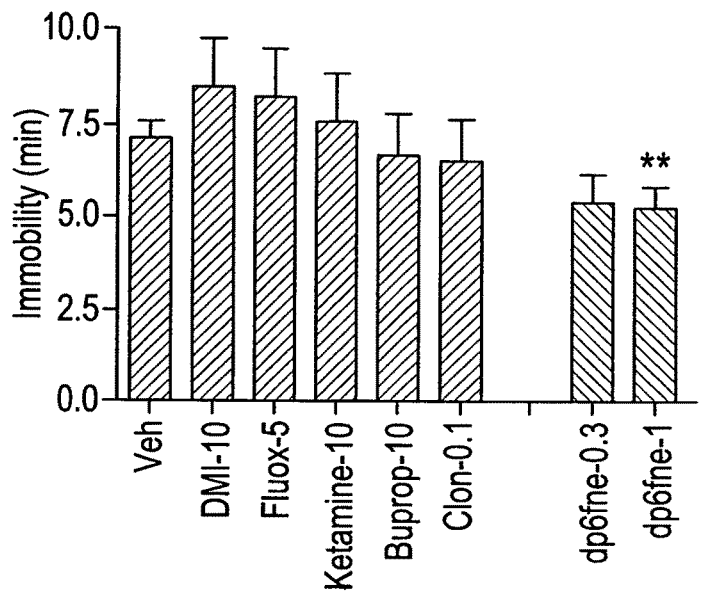
FIG. 14 demonstrates the comparison of acute administration of dp6FNE/prazosin at 0.3 and 1 mg/kg with various currently available antidepressants all given i.p. acutely 15 min prior to the repeated forced swim (RFS) test. Current antidepressant drugs included desmethylimipramine (DMI), fluoxetine (fluox), ketamine, bupropion, (buprop) and clonidine. Doses are in parentheses in mg//kg. N=10-12. *$p<0.05$, $<0.01$, *$<0.001$ versus Vehicle.
Figure 14B:
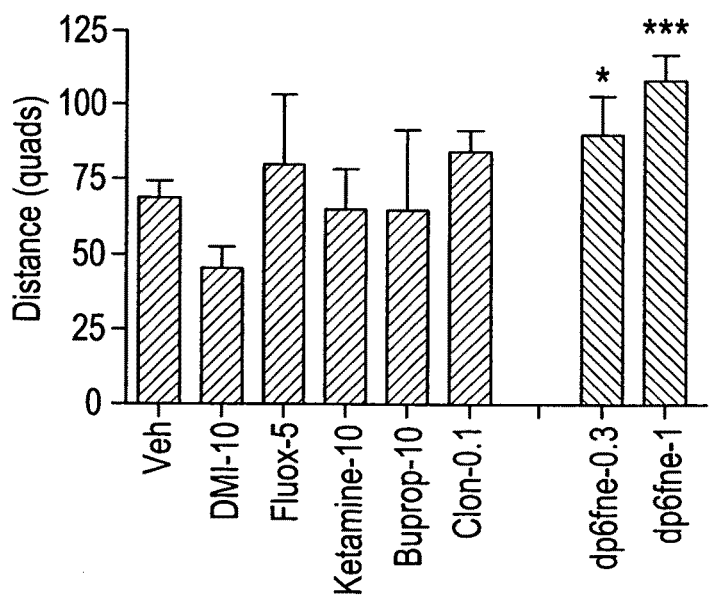

Comparison of effect of acute dp6FNE/prazosin with a panel of currently available acutely administered antidepressants including DMI, fluoxetine, ketamine, bupropion and the $\alpha_2$-agonist, clonidine on the RFS is shown in FIG. 14. One way ANOVAs across all groups yielded significant overall treatment effects for both immobility, $F_{7,70}$=3.12, p<0.01 and distance swum, $F_{7,70}$=4.26, p<0.001. Planned comparisons between each antidepressant and the vehicle group indicated that dp6FNE/prazosin (1 mg/kg) was the only agent that either significantly reduced immobility ($F_{1,70}$=7.31, P<0.01) or increased distance swum ($F_{1,70}$=12.93, p<0.001).

13. Effect of Repeated Treatment with Dp6FNE (RFS)

Figure 15A:
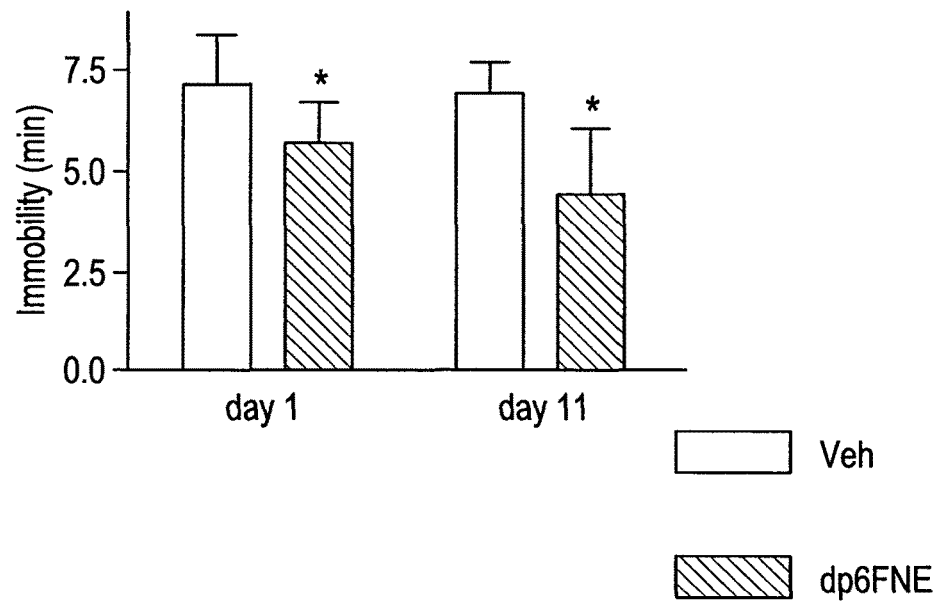
FIG. 15 demonstrates the effect of repeated administration of dp6FNE (0.5 mg/kg)/prazosin (0.2 mg/kg) for 11 d on RFS test. Results are shown for the first and 11th daily injections. N=9-11.
Figure 15B:
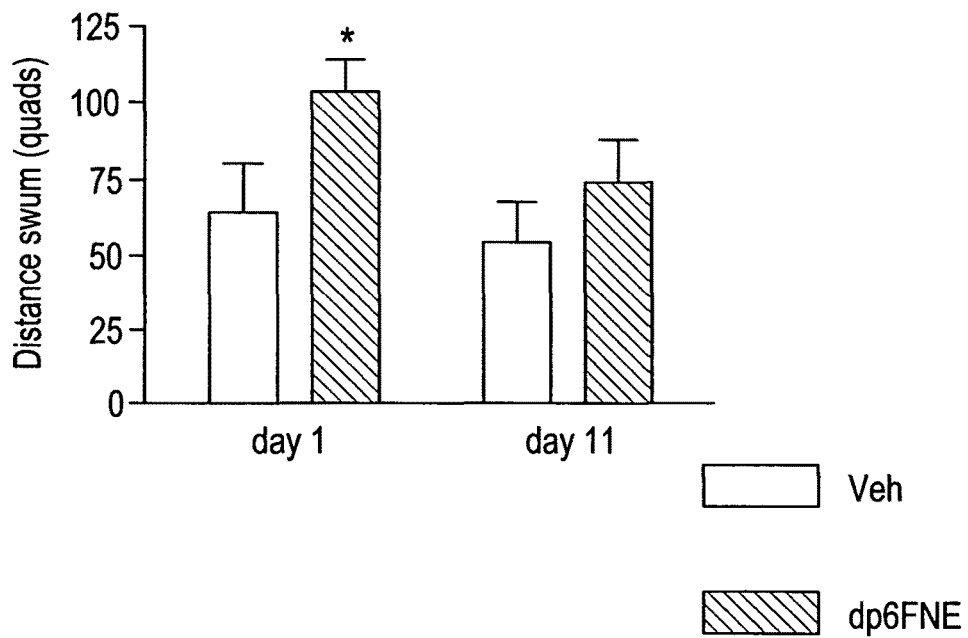

The ability of dp6FNE (0.5 mg/kg)/prazosin to maintain an antidepressant effect in the RFS test when given repeatedly for 11 days is shown in FIG. 15 which presents the data for the first and 11th daily injections. Separate 2×2 (dp6FNE×Day) factorial ANOVAs were computed for the immobility and distance scores. For the former there was a significant main reducing effect of dp6FNE/prazosin ($F_{1,36}$=6.76, p<0.05) with no interaction between dp6FNE and Day of injection. Planned comparisons revealed significant reductions at both Day 1 ($F_{1,36}$=10.84, p<0.005) and Day 11 ($F_{1,35}$=4.18, p<0.05). For distance swum there was a significant increasing main effect of the pro-drug ($F_{1,36}$=4.01, p<0.05) again with no significant drug×Day interaction. Planned comparisons revealed that while dp6FNE/prazosin significantly increased this behavior after the first injection ($F_{1,36}$=10.72, p<0.005) it no longer had a significant effect on it after the eleventh ($F_{1,36}$=2.49, NS).

14. Role of $\alpha_1$- and $\alpha_2$-Adrenoceptors in Effect of dp6FNE in RFS

Figure 16A:
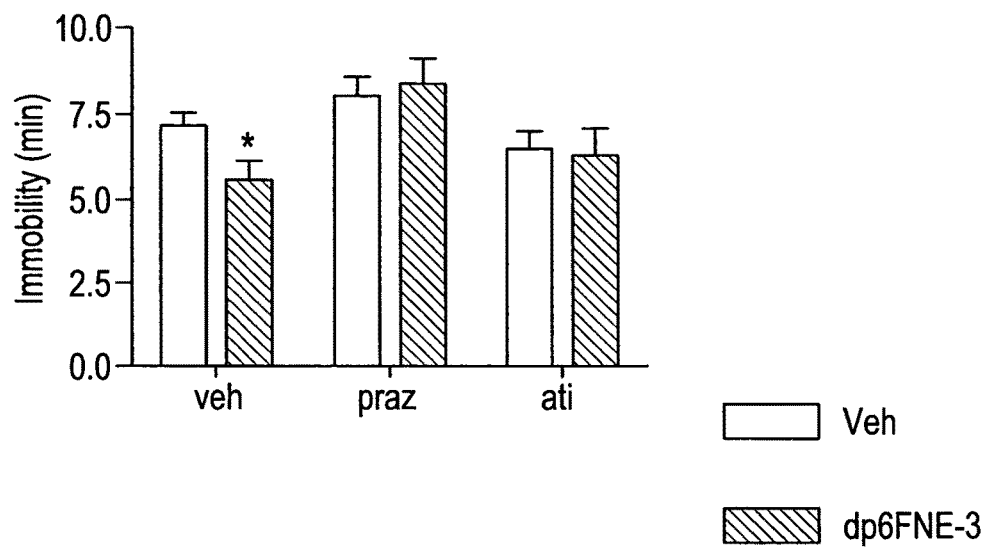
FIG. 16 demonstrates the effect of pretreatment with high dose prazosin (5 mg/kg) or atipamezole (0.5 mg/kg) i.p. 30 min prior to 0.3 mg/kg dp6FNE/prazosin in RFS. N=10-12.
Figure 16B:
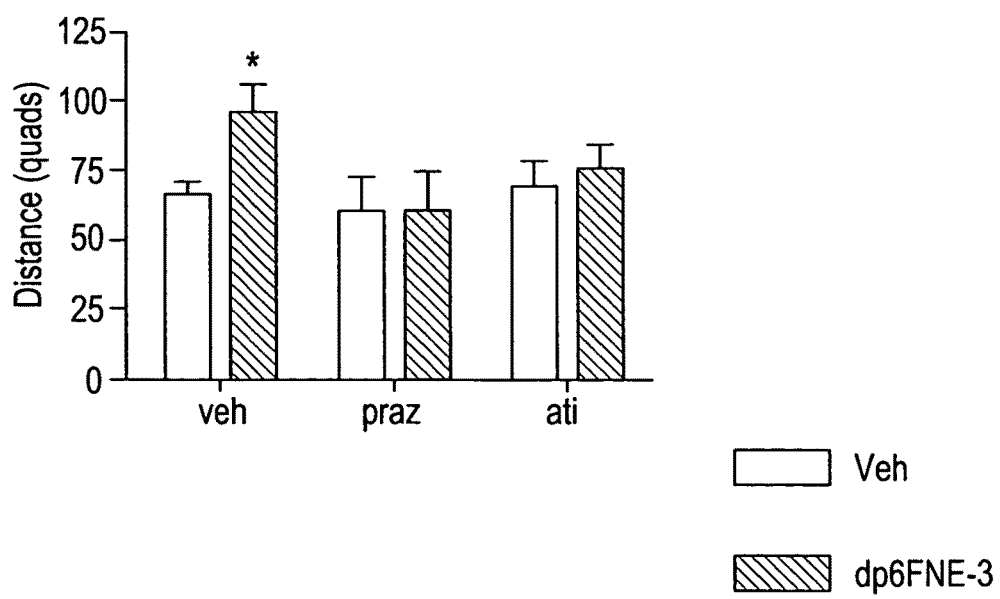

The effects of blocking $\alpha_1$- and $\alpha_2$-adrenoceptors with prazosin (5 mg/kg) and atipamezole (0.5 mg/kg), respectively, on the effects of dp6FNE (0.3 mg/kg)/prazosin (0.2 mg/kg) in the RFS test are shown in FIG. 16. Separate 2×2 dp6FNE×Antagonist factorial ANOVAs were conducted on the immobility and distance swum scores. For immobility, the analysis revealed a significant effect of Antagonist ($F_{2,41}$=4.59, p<0.02) but no significant interaction between Antagonist and dp6FNE ($F_{2,41}$=2.14, NS). Planned comparisons, however, showed that dp6FNE significantly reduced immobility versus vehicle in animals not pretreated with either antagonist ($F_{1,41}$=6.96, p<0.02) but not in those given either high dose prazosin ($F_{1,41}$=0.18, NS) or atipamezole ($F_{1,41}$=0.11, NS). In addition, high dose prazosin pretreatment produced a significant overall increase of immobility ($F_{1,41}$=8.79, p=0.005) whereas atipamezole had no significant overall effect on this behavior ($F_{1,41}$=0.02, NS).

For distance swum, the ANOVA revealed a borderline reducing effect of Antagonist ($F_{1,41}$=2.76, p<0.08) with no significant dp6FNE×Antagonist interaction ($F_{1,41}$=1.67, NS). Planned comparisons showed that dp6FNE versus vehicle significantly increased distances swum in animals not treated with either antagonist ($F_{1,41}$=10.36, p<0.002) but not in those pretreated with either high dose prazosin ($F_{1,41}$=0.002, NS) or atipamezole ($F_{1,41}$=0.18, NS). High dose prazosin pretreatment produced a significant overall decrease of distance swum ($F_{1,41}$=6.97, p=0.02) whereas atipamezole had no significant overall action on this behavior ($F_{1,41}$=2.09, NS).

15. Effect of Dipivalyl-Epinephrine (dpEPI) on RFS

The related pivalyl-substituted catecholamine, DpEPI, given in a vehicle containing prazosin+propranolol also produced a significant reduction in immobility ($t_{16}$=2.27, p<0.05) and an increase in distance swum ($t_{16}$=2.26, p<0.05) versus vehicle in the RFS test (FIG. 17). The prazosin+propranolol vehicle did not differ significantly from distilled water on either behavior (not shown).

16. Effect of dp6FNE on Endotoxin Induced Anhedonia

Figure 18:
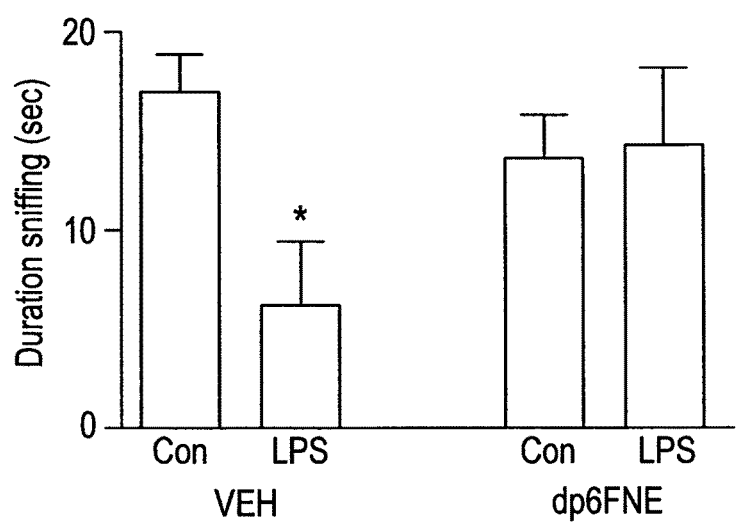

The effects of the pro-drug on endotoxin-induced inhibition of an hedonic behavior, FUST, is shown in FIG. 18. A 2×2 (endotoxin×dp6FNE) factorial ANOVA revealed a borderline reducing effect of endotoxin pretreatment ($F_{1,23}$=3.86, p<0.07) and a significant interaction between endotoxin× dp6FNE/prazosin ($F_{1,23}$=4.57, p<0.05). Planned comparisons showed that endotoxin pretreatment significantly reduced FUST behavior compared to distilled water pretreatment in the animals given prazosin-vehicle ($F_{1,23}$=11.31, P<0.003) but not in those receiving dp6FNE/prazosin on the second day ($F_{1,23}$=0.01, NS). The mice given endotoxin+dp6FNE/prazosin were no longer significantly different from those receiving distilled water+prazosin-vehicle ($F_{1,23}$=2.69, NS) indicating substantial and significant rescue of the behavior. Dp6FNE/prazosin in the absence of endotoxin, produced a small nonsignificant inhibitory effect compared to no treatment ($F_{1,23}$=1.98, NS).

17. Motor Activity and Anxiety in Open Field Test

The effects of dp6FNE/prazosin and amphetamine on locomotor activity and relative time in the center of the open field (ratio of time to total locomotor activity) are shown in FIG. 19. The pro-drug had no significant action on motor activity (quadrants entered) in the 1 h period ($F_{4,26}$=1.28, NS) although a borderline trend of a reduction with increasing dosage was found ($F_{1,26}$=3.83, p=0.06). Amphetamine (2 mg/kg), which was run for purposes of comparison, produced a highly significant increase on locomotion ($F_{1,9}$=115.57, p<0.0001) versus the vehicle group.

Relative time in the center of the field was significantly increased by dp6FNE/prazosin ($F_{4,25}$=3.82, p<0.02) in a linear dose-related fashion (linear trend, $F_{1,25}$=9.77, p<0.005) whereas amphetamine treatment significantly tended to reduce it ($F_{1,9}$=3.96, p<0.08).

Discussion

The present results show that dp6FNE/prazosin possesses antidepressant activity after systemic administration using a variety of tests. The drug combination given i.p. reduced immobility in the TST and RFS tests, and also rescued a hedonic behavior, FUST, that was impaired by pretreatment with endotoxin. The only test in which the pro-drug failed to have a significant effect was the acute forced swim, although a significant trend towards immobility reduction was found for this test. There was, however, a difference in the sensitivity of the RFS and TST to dp6FNE with the former responding to a much lower dose. This is likely due to a greater level of stress caused by the TST than the RFS judging from the abilities of the two to activate Fos expression in the paraventricular hypothalamus (Stone et al., *International Journal of Neuropsychopharmacology* 2011;, 14:319-332). In addition, the lower doses were more effective on immobility than the higher ones, which showed loss of effect. This loss may have resulted from entry of the drug into and inhibition of non-stress brain regions at the higher doses, which would suggest greater stress-selectivity of the lower doses.

In the RFS, the anti-immobility action of dp6FNE was accompanied by an increased distance swum but only at the higher doses. This difference, however, might be the result of the greater effort necessary for swimming distances compared to that for the smaller limb movements that terminate immobility. In support of this view, the effect of the drug on distance swum but not immobility was found to fade significantly with chronic administration. The effect of the drug combination on the TST or RFS was not found to be due to prazosin since the antagonist, when tested alone at the dose of 0.2 mg/kg, did not affect these measures, although an interactive effect cannot be excluded. Furthermore, the its antidepressant effect was not the result of a generalized increase in motor activity since no stimulant action was observed in the open field test which readily detected the activating effect of amphetamine.

Of primary interest to this study is the finding that dp6FNE/prazosin had a significantly faster onset of action in the RFS than a panel of currently available antidepressants including DMI, fluoxetine, bupropion, ketamine and clonidine. The pro-drug was the only agent of this group that either significantly reduced immobility or increased distance swum within minutes of a single administration. As discussed above, the RFS test has been shown to respond to chronic but not acute administration of established antidepressants. There is also evidence that the endotoxin-anhedonia model, which was also reversed by acute dp6FNE/prazosin, also requires chronic antidepressant treatment (Yirmiya, *Brain Research* 1996, 711, 163-174). These findings support the hypothesis that depressive behavior is maintained by ongoing hyperactivity or hyperresponsivity of central stress regions and can be immediately reduced by acute pharmacological inhibition of these. Although most antidepressant agents have been shown to produce long lasting changes in gene and protein expression, neurogenesis and synaptic morphology (Stone, *Behavior and Brain Sciences* 1983, 6, 535-578; Schmidt and Duman, *Behavioral Pharmacology* 2007, 18, 391-418; Marchetti et al., *Biological Psychiatry* 2010, 67, 146-154), these alterations may not be obligatory for the acute pharmacological inhibition of depressive behaviors but rather may be more involved in establishing persistent biases in reactivity.

As discussed above, dp6FNE was designed to stimulate inhibitory $\alpha_1$- and $\alpha_2$-adrenoceptors in or near the LC after systemic administration. The present study provided indirect support for this action by showing that blockade of these receptors with either a high dose systemic prazosin or atipamezole significantly reversed the antidepressant actions of pro-drug in the RFS. These findings await direct confirmation with studies of Fos expression in the LC and other brain regions of the treated animals. Although both antagonists reversed the antidepressant effect, blockade of $\alpha_1$-receptors appeared to affect baseline RFS behaviors to a greater extent since immobility and distance swum were affected more by high dose prazosin than atipamezole. This is consistent with the earlier finding that stimulation of $\alpha_1$-receptors in or near the mouse LC produces greater inhibitory actions on its neural activity as measured by Fos expression than of $\alpha_2$-receptors (Stone et al., *Brain Research* 2009, 1291; 21-31). In further support of this action, a second dipivalyl substituted catecholamine, dpEPI, which also has full agonist actions at $\alpha_1$- and $\alpha_2$-adrenoceptors, was also found to produce a similar acute antidepressant action in the RFS.

Although dp6FNE was designed to be a temporary treatment, it was of interest to determine how long it would remain effective if given repeatedly. The present results indicate that its anti-immobility effect at 0.5 mg/kg, i.p., persists for at least 11 daily treatments whereas its ability to increase swimming distance fades and becomes insignificant at this time, suggesting a possible desensitization of the responsible adrenoceptor(s). Although no formal measures were employed, no obvious signs of toxicity in terms of reduced arousal or disheveled fur coat were observed after repeated treatment.

In summary, the present results indicate that dp6FNE/prazosin has antidepressant activity in a variety of mouse depression tests, involving both motoric and hedonic behavioral endpoints, and is significantly faster acting than a panel of currently available antidepressants including ketamine. The compound also appears to possess anxiolytic activity supporting the view in that it acts by acute suppression of central stress circuits that underlie both depression and anxiety. The new drug appears to act by full agonist stimulation of central $\alpha_1$- and $\alpha_2$-adrenoceptors as may its related and equally effective pro-drug, dpEPI, whose parent catecholamine is also a full agonist at these receptors. Its anti-immobility effect is maintained for as long as 11 days with repeated treatment and is not due to the stimulation of motor activity. dp6FNE may therefore represent a new class of rapidly acting antidepressants which may prove useful for the temporary treatment of highly agitated or suicidal patients who require rapid pharmacological relief of depression and anxiety until longer acting medications take effect.

EXAMPLE 4

To compare the speed and efficacy of ivt PE with ivt 6FNE, both compounds are injected into the 4th ventricle of mice, previously implanted with intraventricular cannulas (4th ventricle), and the animals are tested immediately in the open-space forced swim test. For this test the mice are swum in large tanks of warm water for 15 min/day for 4 days and tested in a last swim on the 5th day. The animals received a single ventricular infusion of each drug at 4 different doses (0, 1, 3 and 10 nmoles) to establish dose response curves. The behavioral endpoints are time immobile (floating, which is a measure of depression in rodents) and distance swum. The open-space repeated forced swim test is known to respond only to chronic and not acute administration of antidepressants (Sun, et al., *J Neurosci Methods* 2003; 126: 35-40). 6FNE is expected to elicit a more rapid or greater antidepressant response than PE and expected to produce a significantly greater reduction of immobility or greater increase in distance swum in this test in response to this single infusion. (Our previous data have already shown that 6FNE is active in this test after a single intraventricular infusion (Stone, et al. *Submitted*, 2009)).

EXAMPLE 5

To compare the speed and efficacy of peripheral cirazoline with peripheral dp6FNE the same experiment is performed as above except that instead of intraventricular injections the animals received i.p. injections of the latter two drugs. Four doses of each agent (0, 1, 3, and 10 mg/kg) are given in the presence of i.p. phentolamine, 1 mg/kg, 30 min before the final test swim. (We have already shown that dp6FNE is active in this test after a single i.p. injection.) These experiments are expected to show dp6FNE is more rapid or efficacious than the partial $\alpha_1$-agonists, PE and cirazoline, respectively, in the preclinical treatment of depression.

EXAMPLE 6

To verify that dp6FNE has anxiolytic effects this agent is tested in both the light/dark box (Shimada, et al., *Gen Pharmac* 1995; 26: 205-210) and elevated plus-maze (Pellow, et al., *J Neurosci Methods* 1985; 14: 149-167). Mice are given one of 4 doses of dp6FNE (0, 1, 3 and 10 mg/kg, i.p.) plus phentolamine (1 mg/kg, i.p.) 30 min prior to each 5 min test. For the plus-maze, the animal is placed in the center section of the maze and videotaped to determine both number of entries and time spent in the open and closed arms of the maze. In the light/dark test, the animal is placed in the light section and videotaped to determine the amount of time spent in the light and dark sides of the chamber. dp6FNE is expected to show the increased time spent in the open arms of the plus maze and in the lighted side of the dark/light box.

At least some of the chemical names of compounds of the invention provided herein, may have been generated on an automated basis by use of a commercially available chemical naming software program, and have not been independently verified. Representative programs performing this function include the Lexichem naming tool sold by Open Eye Software, Inc. and the Autonom Software tool sold by MDL, Inc. In the instance where the indicated chemical name and the depicted structure differ, the depicted structure will control.

Chemical structures shown herein were prepared using ISIS®/DRAW. Any open valency appearing on a carbon, oxygen or nitrogen atom in the structures herein indicates the presence of a hydrogen atom. Where a chiral center exists in a structure but no specific stereochemistry is shown for the chiral center, both enantiomers associated with the chiral structure are encompassed by the structure.

All publications referenced herein are incorporated by reference in their entirety, including all figures and tables, to the extent they are not inconsistent with the explicit teachings of this specification.

What is claimed is:

1. A pharmaceutical composition comprising:
   a) a prodrug or compound according to formula IIIc:

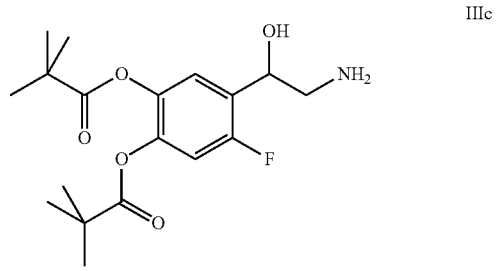 [SMILES: CC(C)(C)C(=O)Oc1cc(F)c(C(O)CN)cc1OC(=O)C(C)(C)C]

or a pharmaceutically acceptable salt, or solvate thereof; and stereoisomers, isotopic variants and tautomers thereof;
   b) an additional α-adrenergic modulator; and
   c) a carrier or adjuvant.

2. The pharmaceutical composition according to claim 1, wherein the prodrug or the compound does pass the blood-brain barrier.

3. The pharmaceutical composition according to claim 1, wherein the prodrug or the compound does pass the blood-brain barrier and is enzymatically cleaved within the brain to yield the active parent catecholamine.

4. The pharmaceutical composition according to claim 1, wherein the additional α-adrenergic modulator is selected from the group consisting of doxazosin, terazosin, labetalol, indoramin, phenoxybenzamine, tolazoline, and dihydroergotamine.

5. The pharmaceutical composition according to claim 1, wherein the additional α-adrenergic modulator is a modulator incapable of crossing the blood-brain barrier.

6. The pharmaceutical composition according to claim 1, wherein the additional α-adrenergic modulator is a modulator which does not enter the brain.

7. The pharmaceutical composition according to any claim 1, wherein the additional α-adrenergic modulator is an α-adrenergic antagonist.

8. The pharmaceutical composition according to claim 1, wherein the additional α-adrenergic modulator is prazosin.

9. The pharmaceutical composition according to claim 1, wherein the additional α-adrenergic modulator is present at dosage levels equivalent to 10 to 100% of the dosage normally administered in a monotherapy regimen.

10. The pharmaceutical composition according to claim 1, wherein the additional α-adrenergic modulator is present at dosage levels equivalent to about 0.5 to about 2 mg of the dose.

11. The pharmaceutical composition according to claim 1, wherein the additional α-adrenergic modulator is present at dosage levels equivalent to about 0.5 to about 2 mg of the dose and is administered twice daily.

12. The pharmaceutical composition according to claim 1, wherein the carrier is a parenteral carrier.

13. The pharmaceutical composition according to claim 1, wherein the carrier is an oral carrier.

14. The pharmaceutical composition according to claim 1, wherein the carrier is a topical carrier.

15. A method for treating α-adrenergic mediated disease or condition in a mammal comprising the step of administering to said mammal a pharmaceutical composition according to claim 1.

16. The method according to claim 15, wherein the disease or condition is an anxiety disorder or a mood disorder.

17. A method for treating a disease selected from the group consisting of an anxiety disorder or a mood disorder in a mammal comprising the step of administering to said mammal a pharmaceutical composition according to claim 1.

18. The method according to claim 17 wherein the disease is an anxiety disorder.

19. The method according to claim 17 wherein the disease is a mood disorder.

20. The method according to claim 19 wherein the mood disorder is selected from the group consisting of dysthymia and major depression.

21. The method according to claim 17 wherein the administering results in a reduction in at least one clinical symptom of depression within one day.

22. The method according to claim 17 wherein the administering results in a reduction in at least one clinical symptom of depression within one week.

23. The method according to claim 17 wherein the administering results in a reduction in at least one clinical symptom of depression within one month.

24. The method according to claim 17 wherein the administering results in reducing a neural response in a stress response.

25. The method according to claim 17 wherein the administering results in increasing neural activity in one or more areas of the brain involved in motivated behavior.

* * * * *